(12) United States Patent
Walsh et al.

(10) Patent No.: US 10,864,100 B2
(45) Date of Patent: Dec. 15, 2020

(54) ORTHOPEDIC DEVICE INCLUDING PROTRUDING MEMBERS

(71) Applicant: President and Fellows of Harvard College, Cambridge, MA (US)

(72) Inventors: Conor James Walsh, Cambridge, MA (US); Alan T. Asbeck, Cambridge, MA (US); Matthew W. Yarri, Cambridge, MA (US); Jillian Christine Cochran, Cambridge, MA (US); Stefano Marco Maria De Rossi, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1025 days.

(21) Appl. No.: 15/302,347

(22) PCT Filed: Apr. 10, 2015

(86) PCT No.: PCT/US2015/025472
§ 371 (c)(1),
(2) Date: Oct. 6, 2016

(87) PCT Pub. No.: WO2015/157731
PCT Pub. Date: Oct. 15, 2015

(65) Prior Publication Data
US 2017/0027735 A1    Feb. 2, 2017

Related U.S. Application Data

(60) Provisional application No. 62/138,848, filed on Mar. 26, 2015, provisional application No. 61/980,961, (Continued)

(51) Int. Cl.
*A61F 5/00*    (2006.01)
*A61F 5/01*    (2006.01)
(Continued)

(52) U.S. Cl.
CPC .......... *A61F 5/0123* (2013.01); *A61F 5/0102* (2013.01); *A61F 5/0125* (2013.01);
(Continued)

(58) Field of Classification Search
CPC .... A61F 5/0123; A61F 5/0102; A61F 5/0125; A61F 2005/0179; A61F 2005/0197;
(Continued)

(56) References Cited

U.S. PATENT DOCUMENTS 3,387,305 A    6/1968    Shafer
3,411,511 A    11/1968   Marino
(Continued)

FOREIGN PATENT DOCUMENTS

CN    1431084 A    7/2003
CN    1868434      11/2006
(Continued)

OTHER PUBLICATIONS

International Search Report and Written Opinion for International Application No. PCT/US2019/033143, dated Oct. 9, 2019.
(Continued)

*Primary Examiner* — Quang D Thanh
(74) *Attorney, Agent, or Firm* — Wolf, Greenfield & Sacks, P.C.

(57) ABSTRACT

Orthopedic devices may include rigid members for coupling to portions of a limb that includes a joint, and a cable that couples to the rigid members and extends up to a powered element. The orthopedic devices are configured to produce beneficial forces using the rigid member and the cable, which beneficial forces are translated to the wearer. The orthopedic devices include control systems that generate control signals for controlling the powered element.

46 Claims, 32 Drawing Sheets

Related U.S. Application Data filed on Apr. 17, 2014, provisional application No. 61/977,880, filed on Apr. 10, 2014.

(51) Int. Cl.
  *A61H 1/02* (2006.01)
  *A61H 3/00* (2006.01)

(52) U.S. Cl.
  CPC ...... *A61H 1/024* (2013.01); *A61F 2005/0137* (2013.01); *A61F 2005/0155* (2013.01); *A61F 2005/0165* (2013.01); *A61F 2005/0179* (2013.01); *A61F 2005/0188* (2013.01); *A61F 2005/0197* (2013.01); *A61H 1/0244* (2013.01); *A61H 1/0266* (2013.01); *A61H 2003/001* (2013.01); *A61H 2201/0165* (2013.01); *A61H 2201/1215* (2013.01); *A61H 2201/1238* (2013.01); *A61H 2201/149* (2013.01); *A61H 2201/164* (2013.01); *A61H 2201/165* (2013.01); *A61H 2201/1642* (2013.01); *A61H 2201/1673* (2013.01); *A61H 2201/501* (2013.01); *A61H 2201/5015* (2013.01); *A61H 2201/5061* (2013.01); *A61H 2201/5064* (2013.01); *A61H 2201/5069* (2013.01); *A61H 2201/5082* (2013.01); *A61H 2201/5084* (2013.01); *A61H 2230/505* (2013.01); *A61H 2230/605* (2013.01)

(58) Field of Classification Search
  CPC ...... A61F 2005/0188; A61F 2005/0165; A61F 2005/0155; A61F 2005/0137; A61H 1/024; A61H 2201/1673; A61H 2201/0165; A61H 2201/5015; A61H 2230/605; A61H 2201/5082; A61H 2201/149; A61H 2201/5084; A61H 2201/1642; A61H 2201/5069; A61H 2201/164; A61H 1/0244; A61H 2201/1238; A61H 2201/5064; A61H 2230/505; A61H 2201/5061; A61H 2201/1215; A61H 1/0266; A61H 2201/165; A61H 2003/001; A61H 2201/501

See application file for complete search history.

(56) References Cited

U.S. PATENT DOCUMENTS

| | | |
|---|---|---|
| 3,831,467 A | 8/1974 | Moore |
| 4,023,215 A | 5/1977 | Moore |
| 4,252,112 A | 2/1981 | Joyce |
| 4,370,977 A * | 2/1983 | Mauldin ............... A61F 5/0125 602/16 |
| 4,682,776 A | 7/1987 | Mitchell et al. |
| 4,697,808 A | 10/1987 | Larson et al. |
| 4,724,827 A | 2/1988 | Schenck |
| 4,760,850 A | 8/1988 | Phillips et al. |
| 5,020,790 A | 6/1991 | Beard et al. |
| 5,282,460 A | 2/1994 | Boldt |
| 5,485,402 A | 1/1996 | Smith et al. |
| 5,584,799 A | 12/1996 | Gray |
| 5,599,283 A | 2/1997 | Lindenmeyer et al. |
| 5,667,461 A | 9/1997 | Hall |
| 5,826,578 A | 10/1998 | Curchod |
| 5,865,714 A | 2/1999 | Marlowe |
| 5,865,770 A | 2/1999 | Schectman |
| 5,955,667 A | 9/1999 | Fyfe |
| 6,123,649 A | 9/2000 | Lee et al. |
| 6,129,691 A | 10/2000 | Ruppert |
| 6,168,634 B1 | 1/2001 | Schmitz |
| 6,213,922 B1 | 4/2001 | Afanasenko et al. |
| 6,500,138 B1 | 12/2002 | Irby et al. |
| 6,517,503 B1 | 2/2003 | Naft et al. |
| 6,633,783 B1 | 10/2003 | Dariush et al. |
| 6,635,024 B2 | 10/2003 | Hatton et al. |
| 6,666,796 B1 * | 12/2003 | MacCready, Jr. ..... A61F 5/0102 135/65 |
| 6,666,831 B1 | 12/2003 | Edgerton et al. |
| 6,689,075 B2 | 2/2004 | West |
| 6,741,911 B2 | 5/2004 | Simmons |
| 6,783,555 B2 | 8/2004 | Kuhn et al. |
| 6,790,165 B2 | 9/2004 | Huang |
| 6,796,926 B2 | 9/2004 | Reinkensmeyer et al. |
| 6,812,624 B1 | 11/2004 | Pei et al. |
| 6,872,187 B1 * | 3/2005 | Stark ................. A61F 5/0102 602/16 |
| 6,955,692 B2 | 10/2005 | Grundei |
| 6,989,669 B2 | 1/2006 | Low et al. |
| 7,034,432 B1 | 4/2006 | Pelrine et al. |
| 7,034,527 B2 | 4/2006 | Low et al. |
| 7,049,732 B2 | 5/2006 | Pei et al. |
| 7,056,297 B2 | 6/2006 | Dohnu et al. |
| 7,064,472 B2 | 6/2006 | Pelrine et al. |
| 7,090,650 B2 | 8/2006 | Ou et al. |
| 7,153,242 B2 | 12/2006 | Goffer |
| 7,153,246 B2 | 12/2006 | Koscielny et al. |
| 7,166,953 B2 | 1/2007 | Heim et al. |
| 7,190,141 B1 | 3/2007 | Ashrafiuon et al. |
| 7,199,501 B2 | 4/2007 | Pei et al. |
| 7,211,937 B2 | 5/2007 | Kornbluh et al. |
| 7,224,106 B2 | 5/2007 | Pei et al. |
| 7,229,390 B2 | 6/2007 | Fujii et al. |
| 7,233,097 B2 | 6/2007 | Rosenthal et al. |
| 7,252,644 B2 | 8/2007 | Dewald et al. |
| 7,259,503 B2 | 8/2007 | Pei et al. |
| 7,259,553 B2 | 8/2007 | Arns, Jr. et al. |
| 7,307,418 B2 | 12/2007 | Low et al. |
| 7,331,906 B2 | 2/2008 | He et al. |
| 7,341,295 B1 | 3/2008 | Veatch et al. |
| 7,355,519 B2 | 4/2008 | Grold et al. |
| 7,367,958 B2 | 5/2008 | McBean et al. |
| 7,368,862 B2 | 5/2008 | Pelrine et al. |
| 7,378,878 B2 | 5/2008 | Pelrine et al. |
| 7,390,309 B2 | 6/2008 | Dariush |
| 7,410,471 B1 | 8/2008 | Campbell et al. |
| 7,411,332 B2 | 8/2008 | Kornbluh et al. |
| 7,429,253 B2 | 9/2008 | Shimada et al. |
| 7,436,099 B2 | 10/2008 | Pei et al. |
| 7,445,606 B2 | 11/2008 | Rastegar et al. |
| 7,456,549 B2 | 11/2008 | Heim et al. |
| 7,476,185 B2 | 1/2009 | Drennan |
| 7,494,450 B2 | 2/2009 | Solomon |
| 7,521,840 B2 | 4/2009 | Heim |
| 7,521,847 B2 | 4/2009 | Heim |
| 7,537,573 B2 | 5/2009 | Horst |
| 7,549,969 B2 | 6/2009 | van den Bogert |
| 7,567,681 B2 | 7/2009 | Pelrine et al. |
| 7,578,799 B2 | 8/2009 | Thorsteinsson et al. |
| 7,595,580 B2 | 9/2009 | Heim |
| 7,598,651 B2 | 10/2009 | Kornbluh et al. |
| 7,598,652 B2 | 10/2009 | Kornbluh et al. |
| 7,626,319 B2 | 12/2009 | Heim |
| 7,650,204 B2 | 1/2010 | Dariush |
| 7,652,386 B2 | 1/2010 | Donelan et al. |
| 7,654,973 B2 | 2/2010 | Firsov |
| 7,679,267 B2 | 3/2010 | Heim |
| 7,684,896 B2 | 3/2010 | Dariush |
| 7,705,521 B2 | 4/2010 | Pelrine et al. |
| 7,737,685 B2 | 6/2010 | Low et al. |
| 7,750,532 B2 | 7/2010 | Heim |
| 7,758,481 B2 | 7/2010 | Drennan |
| 7,774,177 B2 | 8/2010 | Dariush |
| 7,775,999 B2 | 8/2010 | Brown |
| 7,785,279 B2 | 8/2010 | Sankai |
| 7,785,656 B2 | 8/2010 | Pei |
| 7,787,646 B2 | 8/2010 | Pelrine et al. |
| 7,804,227 B2 | 9/2010 | Pelrine et al. |
| 7,857,774 B2 | 12/2010 | Sankai |
| 7,860,562 B2 | 12/2010 | Endo et al. |
| 7,883,546 B2 | 2/2011 | Kazerooni et al. |

(56) References Cited

U.S. PATENT DOCUMENTS

| | | | |
|---|---|---|---|
| 7,887,471 B2 | 2/2011 | McSorley |
| 7,897,168 B2 | 3/2011 | Chen et al. |
| 7,911,761 B2 | 3/2011 | Biggs et al. |
| 7,915,790 B2 | 3/2011 | Heim et al. |
| 7,918,808 B2 | 4/2011 | Simmons |
| 7,921,541 B2 | 4/2011 | Pei et al. |
| 7,923,064 B2 | 4/2011 | Pelrien et al. |
| 7,923,902 B2 | 4/2011 | Heim |
| 7,947,004 B2 | 5/2011 | Kazerooni et al. |
| 7,952,261 B2 | 5/2011 | Lipton et al. |
| 7,985,193 B2 | 6/2011 | Thorsteinsson et al. |
| 7,977,923 B2 | 7/2011 | Pelrine et al. |
| 7,981,508 B1 | 7/2011 | Sharma et al. |
| 7,990,022 B2 | 8/2011 | Heim |
| 7,998,040 B2 | 8/2011 | Kram et al. |
| 8,048,007 B2 | 11/2011 | Roy |
| 8,057,410 B2 | 11/2011 | Angold et al. |
| 8,058,861 B2 | 11/2011 | Pelrine et al. |
| 8,060,337 B2 | 11/2011 | Kulach et al. |
| 8,075,633 B2 | 12/2011 | Herr et al. |
| 8,083,644 B2 | 12/2011 | Purdy et al. |
| 8,096,965 B2 | 1/2012 | Goffer et al. |
| 8,114,034 B2 | 2/2012 | Ikeuchi et al. |
| 8,125,755 B2 | 2/2012 | Garcia et al. |
| 8,127,437 B2 | 3/2012 | Lipton et al. |
| 8,142,370 B2 | 3/2012 | Weinberg et al. |
| 8,147,436 B2 | 4/2012 | Agrawal et al. |
| 8,164,232 B2 | 4/2012 | Kornbluh et al. |
| 8,183,739 B2 | 5/2012 | Heim |
| 8,222,799 B2 | 7/2012 | Polyakov et al. |
| 8,231,687 B2 | 7/2012 | Bedard et al. |
| 8,235,869 B2 | 8/2012 | Rastegar et al. |
| 8,246,559 B2 | 8/2012 | Hoffman et al. |
| 8,248,750 B2 | 8/2012 | Biggs et al. |
| 8,274,244 B2 | 9/2012 | Bhugm et al. |
| 8,283,839 B2 | 10/2012 | Heim |
| 8,287,477 B1 | 10/2012 | Herr et al. |
| 8,292,836 B2 | 10/2012 | Matsuoka et al. |
| 8,299,634 B2 | 10/2012 | Donelan et al. |
| 8,311,623 B2 | 11/2012 | Sanger |
| 8,316,526 B2 | 11/2012 | Pei et al. |
| 8,316,719 B2 | 11/2012 | Majidi et al. |
| 8,323,355 B2 | 12/2012 | Latour |
| 8,325,458 B2 | 12/2012 | Prahlad et al. |
| 8,348,875 B2 | 1/2013 | Goffer et al. |
| 8,376,971 B1 | 2/2013 | Herr et al. |
| 8,409,117 B2 | 4/2013 | Cheng et al. |
| 8,436,508 B2 | 5/2013 | Kornbluh et al. |
| 8,438,757 B2 | 5/2013 | Roser |
| 8,460,001 B1 | 6/2013 | Chuang |
| 8,467,904 B2 | 6/2013 | Dariush |
| 8,488,295 B2 | 7/2013 | Garcia et al. |
| 8,508,109 B2 | 8/2013 | Pelrine et al. |
| 8,551,029 B1 | 10/2013 | Herr et al. |
| 8,551,184 B1 | 10/2013 | Herr |
| 8,562,691 B2 | 10/2013 | Endo et al. |
| 8,564,926 B2 | 10/2013 | Prahlad et al. |
| 8,573,982 B1 | 11/2013 | Chuang |
| 8,585,620 B2 | 11/2013 | McBean et al. |
| 8,597,369 B2 | 12/2013 | Hansen et al. |
| 8,608,479 B2 | 12/2013 | Liu |
| 8,608,674 B2 | 12/2013 | Krebs et al. |
| 8,622,938 B2 | 1/2014 | Sankai |
| 8,663,133 B2 | 3/2014 | Johnson et al. |
| 8,665,578 B2 | 3/2014 | Pelrine et al. |
| 8,679,575 B2 | 3/2014 | Biggs et al. |
| 8,715,208 B2 | 5/2014 | Hodgins et al. |
| 8,766,925 B2 | 6/2014 | Perlin et al. |
| 8,764,850 B2 | 7/2014 | Hansen et al. |
| 8,773,148 B2 | 7/2014 | Sankai et al. |
| 8,847,611 B2 | 9/2014 | Ulmen et al. |
| 8,905,955 B2 | 12/2014 | Goffer et al. |
| 8,920,517 B2 | 12/2014 | Smith et al. |
| 8,926,534 B2 | 1/2015 | McBean et al. |
| 8,938,289 B2 | 1/2015 | Einav et al. |
| 8,961,439 B2 | 2/2015 | Yang et al. |
| 8,975,888 B2 | 3/2015 | Pelrine et al. |
| 8,981,621 B2 | 3/2015 | Pelrine et al. |
| 8,986,233 B2 | 3/2015 | Aoki et al. |
| 9,044,346 B2 | 6/2015 | Langlois et al. |
| 9,072,941 B2 | 7/2015 | Duda et al. |
| 9,101,323 B2 | 8/2015 | Einarsson et al. |
| 9,144,528 B2 | 9/2015 | Agrawal et al. |
| 9,149,370 B2 | 10/2015 | Herr et al. |
| 9,195,794 B2 | 11/2015 | Dariush |
| 9,198,821 B2 | 12/2015 | Unluhisarcikli et al. |
| 9,221,177 B2 | 12/2015 | Herr et al. |
| 9,227,108 B1 | 1/2016 | Chuang |
| 9,228,822 B2 | 1/2016 | Majidi et al. |
| 9,231,186 B2 | 1/2016 | Busgen et al. |
| 9,266,233 B2 | 2/2016 | Kornbluh et al. |
| 9,333,097 B2 | 5/2016 | Herr et al. |
| 9,351,900 B2 | 5/2016 | Walsh et al. |
| 9,387,096 B2 | 6/2016 | Sverrisson et al. |
| 9,403,272 B2 | 8/2016 | Kornbluh et al. |
| 9,427,864 B2 | 8/2016 | Kornbluh et al. |
| 10,028,881 B2 | 7/2018 | Yamamoto et al. |
| 10,115,319 B2 | 10/2018 | Asbeck et al. |
| 10,278,883 B2 | 5/2019 | Walsh et al. |
| 10,427,293 B2 | 10/2019 | Asbeck et al. |
| 10,434,030 B2 | 10/2019 | Asbeck et al. |
| 2001/0007845 A1 | 7/2001 | Afanasenko et al. |
| 2002/0169402 A1* | 11/2002 | Hatton ............... A61F 5/0125 602/26 |
| 2003/0009120 A1 | 1/2003 | MacAllister |
| 2003/0030397 A1 | 2/2003 | Simmons |
| 2003/0064869 A1 | 4/2003 | Reinkensmeyer et al. |
| 2003/0092545 A1 | 5/2003 | Koscielny et al. |
| 2003/0096310 A1 | 5/2003 | Hansen et al. |
| 2003/0120183 A1 | 6/2003 | Simmons |
| 2003/0125781 A1 | 7/2003 | Dohno et al. |
| 2004/0043879 A1 | 3/2004 | Huang |
| 2004/0064195 A1 | 4/2004 | Herr |
| 2004/0087418 A1 | 5/2004 | Eldridge |
| 2004/0106881 A1 | 6/2004 | McBean et al. |
| 2004/0116260 A1 | 7/2004 | Drennan |
| 2004/0147378 A1 | 7/2004 | Conklin et al. |
| 2004/0191321 A1 | 9/2004 | Guan et al. |
| 2004/0204294 A2 | 10/2004 | Wilkinson et al. |
| 2005/0010150 A1 | 1/2005 | Firsov |
| 2005/0049865 A1 | 3/2005 | Yaxin et al. |
| 2005/0070834 A1 | 3/2005 | Herr et al. |
| 2005/0101448 A1 | 5/2005 | He et al. |
| 2005/0107725 A1 | 5/2005 | Wild |
| 2005/0157893 A1 | 7/2005 | Pelrine et al. |
| 2005/0184878 A1 | 8/2005 | Grold et al. |
| 2005/0251079 A1* | 11/2005 | Carvey ............... A61F 5/0102 602/26 |
| 2005/0288157 A1 | 12/2005 | Santos-Munne et al. |
| 2006/0079817 A1 | 4/2006 | Dewald et al. |
| 2006/0108755 A1 | 5/2006 | Smyler et al. |
| 2006/0136206 A1 | 6/2006 | Ariu et al. |
| 2006/0192465 A1 | 8/2006 | Kornbluh et al. |
| 2006/0249315 A1 | 11/2006 | Herr et al. |
| 2007/0004570 A1 | 1/2007 | Afanasenko et al. |
| 2007/0004571 A1 | 1/2007 | Gonzalez |
| 2007/0066918 A1 | 3/2007 | Dewald et al. |
| 2007/0111868 A1 | 5/2007 | Fujii et al. |
| 2007/0123997 A1 | 5/2007 | Herr et al. |
| 2007/0135279 A1 | 6/2007 | Purdy et al. |
| 2007/0276270 A1 | 11/2007 | Tran |
| 2008/0000317 A1 | 1/2008 | Patton et al. |
| 2008/0039756 A1* | 2/2008 | Thorsteinsson ...... A61B 5/1038 602/23 |
| 2008/0062589 A1 | 3/2008 | Drabing |
| 2008/0071386 A1 | 3/2008 | McBean et al. |
| 2008/0075930 A1 | 3/2008 | Kornbluh et al. |
| 2008/0097269 A1 | 4/2008 | Weinberg et al. |
| 2008/0156363 A1 | 7/2008 | Ikeuchi et al. |
| 2008/0173365 A1 | 7/2008 | Unger et al. |
| 2008/0218132 A1 | 9/2008 | Pelrine et al. |
| 2008/0224564 A1 | 9/2008 | Pelrine et al. |
| 2008/0255488 A1 | 10/2008 | Agrawal et al. |
| 2008/0289952 A1 | 11/2008 | Pelrine et al. |

(56) References Cited

U.S. PATENT DOCUMENTS

| | | |
|---|---|---|
| 2008/0294019 A1 | 11/2008 | Tran |
| 2008/0300118 A1 | 12/2008 | Wehrell |
| 2009/0042702 A1 | 2/2009 | Toronto et al. |
| 2009/0221928 A1 | 9/2009 | Einav et al. |
| 2009/0255531 A1 | 10/2009 | Johnson et al. |
| 2009/0256817 A1 | 10/2009 | Perlin et al. |
| 2009/0306548 A1* | 12/2009 | Bhugra ............. A61H 1/024 600/587 |
| 2009/0319054 A1 | 12/2009 | Sankai |
| 2010/0000547 A1 | 1/2010 | Johnson et al. |
| 2010/0007240 A1 | 1/2010 | Kornbluh et al. |
| 2010/0024180 A1 | 2/2010 | Pei et al. |
| 2010/0026143 A1 | 2/2010 | Pelrine et al. |
| 2010/0030343 A1 | 2/2010 | Hansen et al. |
| 2010/0038983 A1 | 2/2010 | Bhugm et al. |
| 2010/0056966 A1 | 3/2010 | Toth |
| 2010/0144490 A1 | 6/2010 | Purdy et al. |
| 2010/0152630 A1 | 6/2010 | Matsuoka et al. |
| 2010/0185259 A1 | 7/2010 | Shiba et al. |
| 2010/0185301 A1 | 7/2010 | Hansen et al. |
| 2010/0204804 A1 | 8/2010 | Garrec |
| 2010/0271051 A1 | 10/2010 | Sankai et al. |
| 2010/0274364 A1 | 10/2010 | Pacanowsky |
| 2010/0280628 A1 | 11/2010 | Sankai |
| 2010/0286796 A1 | 11/2010 | Clausen |
| 2010/0298834 A1 | 11/2010 | Hildebrandt |
| 2010/0319215 A1 | 12/2010 | Roser |
| 2010/0324698 A1 | 12/2010 | Sverrisson et al. |
| 2011/0004322 A1 | 1/2011 | Sankai |
| 2011/0009793 A1 | 1/2011 | Lucero |
| 2011/0022349 A1 | 1/2011 | Kulach et al. |
| 2011/0033835 A1 | 1/2011 | Endo et al. |
| 2011/0025170 A1 | 2/2011 | Rosenthal et al. |
| 2011/0040216 A1 | 2/2011 | Herr et al. |
| 2011/0062948 A1 | 3/2011 | Arns, Jr. et al. |
| 2011/0071647 A1 | 3/2011 | Mahon |
| 2011/0093089 A1 | 4/2011 | Martin |
| 2011/0105966 A1 | 5/2011 | Kazerooni et al. |
| 2011/0150966 A1 | 5/2011 | Kazerooni et al. |
| 2011/0152696 A1 | 6/2011 | Ryan |
| 2011/0154641 A1 | 6/2011 | Pelrine et al. |
| 2011/0155307 A1 | 6/2011 | Pelrine et al. |
| 2011/0174524 A1 | 7/2011 | Sharma et al. |
| 2011/0193362 A1 | 8/2011 | Prahlad et al. |
| 2011/0201978 A1 | 8/2011 | Jeon et al. |
| 2011/0209337 A1 | 9/2011 | Pei et al. |
| 2011/0245738 A1 | 10/2011 | Agrawal et al. |
| 2011/0282255 A1 | 11/2011 | Nace |
| 2011/0295384 A1 | 12/2011 | Herr et al. |
| 2011/0295385 A1 | 12/2011 | Herr et al. |
| 2011/0313331 A1 | 12/2011 | Dehez et al. |
| 2012/0019223 A1 | 1/2012 | Pelrine et al. |
| 2012/0023638 A1 | 2/2012 | Leicester |
| 2012/0056903 A1 | 3/2012 | Shinohara et al. |
| 2012/0071797 A1 | 3/2012 | Aoki et al. |
| 2012/0100286 A1 | 4/2012 | Sharma et al. |
| 2012/0109031 A1 | 5/2012 | Vollbrecht |
| 2012/0120544 A1 | 5/2012 | Pelrine et al. |
| 2012/0128960 A1 | 5/2012 | Busgen et al. |
| 2012/0165709 A1 | 6/2012 | Goffer et al. |
| 2012/0169184 A1 | 7/2012 | Pelrine et al. |
| 2012/0177934 A1 | 7/2012 | Vogel et al. |
| 2012/0179075 A1 | 7/2012 | Perry et al. |
| 2012/0181896 A1 | 7/2012 | Kronbluh et al. |
| 2012/0185052 A1 | 7/2012 | Lefeber |
| 2012/0209152 A1 | 8/2012 | Cordo |
| 2012/0238914 A1 | 9/2012 | Goldfield et al. |
| 2012/0248942 A1 | 10/2012 | Biggs et al. |
| 2012/0253234 A1 | 10/2012 | Yang et al. |
| 2012/0271207 A1 | 10/2012 | Schoen et al. |
| 2012/0279175 A1 | 11/2012 | Biggs et al. |
| 2012/0289870 A1 | 11/2012 | Hsiao-Wecksler et al. |
| 2012/0330198 A1 | 12/2012 | Patoglu |
| 2013/0013085 A1 | 1/2013 | Smith et al. |
| 2013/0019749 A1 | 1/2013 | Hufton et al. |
| 2013/0040783 A1 | 2/2013 | Duda et al. |
| 2013/0041617 A1 | 2/2013 | Pease et al. |
| 2013/0045530 A1 | 2/2013 | Gracias et al. |
| 2013/0058001 A1 | 3/2013 | Prahlad et al. |
| 2013/0079686 A1 | 3/2013 | Sessions |
| 2013/0093439 A1 | 4/2013 | Ulmen et al. |
| 2013/0102935 A1 | 4/2013 | Kazerooni et al. |
| 2013/0123672 A1 | 5/2013 | Goffer et al. |
| 2013/0130866 A1 | 5/2013 | Wehrell |
| 2013/0131555 A1 | 5/2013 | Hook |
| 2013/0158444 A1 | 6/2013 | Herr et al. |
| 2013/0165817 A1 | 6/2013 | Horst et al. |
| 2013/0179154 A1 | 7/2013 | Okuno |
| 2013/0186699 A1 | 7/2013 | Prahald et al. |
| 2013/0211295 A1 | 8/2013 | Johnson et al. |
| 2013/0225371 A1 | 8/2013 | Harrer et al. |
| 2013/0226048 A1 | 8/2013 | Unluhisarcikli et al. |
| 2013/0230667 A1 | 9/2013 | Sharma et al. |
| 2013/0237884 A1 | 9/2013 | Kazerooni et al. |
| 2013/0245512 A1 | 9/2013 | Goffer et al. |
| 2013/0253385 A1 | 9/2013 | Goffer et al. |
| 2013/0261513 A1 | 10/2013 | Goffer et al. |
| 2013/0261766 A1 | 10/2013 | Langlois et al. |
| 2013/0268256 A1 | 10/2013 | Dariush |
| 2013/0274640 A1 | 10/2013 | Butters et al. |
| 2013/0288863 A1 | 10/2013 | Yamamoto et al. |
| 2013/0289452 A1 | 10/2013 | Smith et al. |
| 2013/0296746 A1 | 11/2013 | Herr et al. |
| 2013/0307370 A1 | 11/2013 | Jenninger et al. |
| 2013/0310979 A1 | 11/2013 | Herr et al. |
| 2013/0312541 A1 | 11/2013 | Majidi et al. |
| 2013/0328440 A1 | 12/2013 | Kornbluh et al. |
| 2014/0046455 A1 | 2/2014 | Herr et al. |
| 2014/0194781 A1 | 7/2014 | Einarsson et al. |
| 2014/0213951 A1 | 7/2014 | Pietrusisnki et al. |
| 2014/0276304 A1* | 9/2014 | Dollar ............. A61F 5/0102 602/16 |
| 2014/0277739 A1 | 9/2014 | Kornbluh et al. |
| 2014/0358040 A1 | 12/2014 | Kim et al. |
| 2015/0005685 A1* | 1/2015 | Chetlapalli ......... A61F 5/0125 602/16 |
| 2015/0099945 A1 | 4/2015 | Hawkins, III et al. |
| 2015/0142130 A1 | 5/2015 | Goldfarb et al. |
| 2015/0173993 A1 | 6/2015 | Walsh et al. |
| 2015/0266180 A1 | 9/2015 | Kornbluh et al. |
| 2015/0266181 A1 | 9/2015 | Kornbluh et al. |
| 2015/0297934 A1 | 10/2015 | Agrawal et al. |
| 2015/0298765 A1 | 10/2015 | Golden, Jr. |
| 2015/0321339 A1 | 11/2015 | Asbeck et al. |
| 2015/0321399 A1 | 11/2015 | Hong et al. |
| 2016/0101516 A1 | 4/2016 | Kornbluh et al. |
| 2016/0101517 A1 | 4/2016 | Kornbluh et al. |
| 2016/0107309 A1 | 4/2016 | Walsh et al. |
| 2016/0220438 A1 | 8/2016 | Walsh et al. |
| 2016/0278948 A1 | 9/2016 | Piercy et al. |
| 2016/0284231 A1 | 9/2016 | Walsh et al. |
| 2016/0346156 A1 | 12/2016 | Walsh et al. |
| 2017/0163435 A1 | 6/2017 | Ehsani et al. |
| 2017/0176167 A1 | 6/2017 | Keller et al. |
| 2017/0202724 A1 | 7/2017 | Walsh et al. |
| 2018/0008502 A1 | 1/2018 | Asbeck et al. |
| 2018/0056104 A1 | 3/2018 | Cromie et al. |
| 2018/0370020 A1 | 12/2018 | Murakami et al. |
| 2019/0008714 A1 | 1/2019 | Murakami et al. |
| 2019/0021933 A1 | 1/2019 | Murakami et al. |
| 2019/0029912 A1 | 1/2019 | Murakami et al. |
| 2019/0060156 A1 | 2/2019 | Swift et al. |
| 2019/0060157 A1 | 2/2019 | Lamb et al. |
| 2019/0070062 A1 | 3/2019 | O'Donnell et al. |

FOREIGN PATENT DOCUMENTS

| | | |
|---|---|---|
| CN | 202342034 | 7/2012 |
| CN | 101175456 | 3/2013 |
| CN | 102327173 | 5/2013 |
| DE | 19944139 | 4/2001 |
| EP | 0016268 | 10/1980 |
| EP | 0141640 | 10/1984 |
| EP | 0302148 | 2/1989 |

(56) References Cited

FOREIGN PATENT DOCUMENTS

| | | |
|---|---|---|
| EP | 0509723 A1 | 10/1992 |
| EP | 1306792 | 5/2003 |
| EP | 1324403 | 7/2003 |
| EP | 1260201 | 12/2008 |
| EP | 2226053 | 9/2010 |
| EP | 1842518 | 9/2011 |
| EP | 1589059 | 6/2012 |
| EP | 2497610 | 9/2012 |
| EP | 2548543 | 1/2013 |
| EP | 1550689 | 4/2013 |
| EP | 2649976 | 10/2013 |
| JP | H107163607 A | 6/1995 |
| JP | 2002301124 A | 10/2002 |
| JP | 2005000500 A | 1/2005 |
| JP | 2007000391 A | 1/2007 |
| JP | 2008/067762 | 3/2008 |
| JP | 4345025 | 10/2009 |
| JP | 2010042069 A | 2/2010 |
| JP | 2010/051416 | 3/2010 |
| JP | 4424269 | 3/2010 |
| JP | 2010075656 A | 4/2010 |
| JP | 4582523 | 11/2010 |
| JP | 2011/036375 | 2/2011 |
| JP | 4848260 | 12/2011 |
| JP | 2012/192013 | 10/2012 |
| JP | 2013146328 A | 8/2013 |
| JP | 2013-208397 A | 10/2013 |
| JP | 2014018536 A | 2/2014 |
| JP | 2014034145 A1 | 3/2014 |
| WO | WO 00/12041 A2 | 3/2000 |
| WO | WO2004/017890 | 3/2004 |
| WO | WO2004/039292 | 5/2004 |
| WO | WO2004/047928 | 6/2004 |
| WO | WO2005/102208 | 11/2005 |
| WO | WO2011/008934 | 1/2011 |
| WO | WO2011/026086 | 3/2011 |
| WO | WO2011/030641 | 3/2011 |
| WO | 2011126985 A2 | 10/2011 |
| WO | 2012014164 A2 | 2/2012 |
| WO | WO2012/050938 | 4/2012 |
| WO | WO2012/103073 | 8/2012 |
| WO | WO2012/124328 | 9/2012 |
| WO | WO2012/178171 | 12/2012 |
| WO | WO2013/019749 | 2/2013 |
| WO | 2013033669 A2 | 3/2013 |
| WO | WO2013/033669 | 3/2013 |
| WO | WO2013/044226 | 3/2013 |
| WO | 2013049658 A1 | 4/2013 |
| WO | WO 2013/146231 A1 | 10/2013 |
| WO | WO2014/109799 | 7/2014 |
| WO | WO2014/194257 | 12/2014 |
| WO | WO 2015/074070 A1 | 5/2015 |
| WO | WO2015/120186 | 8/2015 |
| WO | WO2015/157731 | 10/2015 |
| WO | WO2015/088863 | 12/2015 |
| WO | WO 2016/044251 A1 | 3/2016 |
| WO | WO2016/089466 | 6/2016 |
| WO | WO2017/040669 | 3/2017 |
| WO | 2017160751 A1 | 9/2017 |
| WO | 2018017436 A1 | 1/2018 |

OTHER PUBLICATIONS

International Search Report and Written Opinion for International Application No. PCT/US2018/022494, dated Jun. 8, 2018.

Bae et al, A Soft Exosuit for Patients with Stroke: Feasibility study with a mobile off-board actuation unit. 2015 IEEE International Conference on Rehabilitation Robotics (ICORR). Aug. 11, 2015; 131-8.

Laughton et al., Effect of Strike Pattern and Orthotic Intervention on Tibial Shock During Running. Journal of Applied Biomechanics. May 1, 2003; 19(2): 153-68.

Lenhart et al., Increasing Running Step Rate Reduces Patellofemoral Joint Forces. Medicine & Science in Sports & Exercise. Mar. 2014; 46(3): 557-64.

Lieberman et al., Effects of stride frequency and foot position in landing on braking force, hip torque, impact peak force and the metabolic cost of running in humans. Journal of Experimental Biology. Nov. 1, 2015; 218(21):3406-14.

Sinclair et al., Determination of Gait Events Using an Externally Mounted Accelerometer. Journal of Applied Biomechanics. Feb. 1, 2013; 29(1): 118-22.

Extended European Search Report issued in European Application No. 15746146.8 dated Feb. 27, 2018.

U.S. Appl. No. 15/097,744, filed Apr. 13, 2016, Asbeck et al.
U.S. Appl. No. 15/102,694, filed Mar. 31, 2017, De Rossi et al.
U.S. Appl. No. 14/893,934, filed Nov. 24, 2015, Walsh et al.
U.S. Appl. No. 16/538,746, filed Aug. 12, 2019, Asbeck et al.
U.S. Appl. No. 16/317,845, filed Jan. 15, 2019, Ding et al.
U.S. Appl. No. 16/493,746, filed Sep. 12, 2019, Bartlett et al.
U.S. Appl. No. 16/084,377, filed Sep. 12, 2018, O'Donnell et al.

PCT/US2019/033143, dated Oct. 9, 2019, International Search Report and Written Opinion.

PCT/US2018/022494, dated Jun. 8, 2018, International Search Report and Written Opinion.

USPTO Office Action in U.S. Appl. No. 14/660,704 dated Jun. 28, 2018.

USPTO Office Action in U.S. Appl. No. 15/117,034 dated Oct. 5, 2018.

USPTO Office Action in U.S. Appl. No. 14/660,704 dated Nov. 8, 2018.

PCT International Search Report and Written Opinion, issued in International Application No. PCT/US2017/042286, dated Sep. 28, 2017.

Supplementary European Search Report issued in European Application No. 15 77 6544 dated Oct. 20, 2017.

USPTO Office Action in U.S. Appl. No. 14/660,704 dated Feb. 7, 2018.

Banala, S. K. et al., "Active leg exoskeleton (alex) for gait rehabilitation of motor-impaired patients," in Proc. 2007 IEEE 10th Int. Conf. Rehabil Robotics, pp. 401-407, Jun. 2007.

Browning, R. C. et al., "The effects of adding mass to the legs on the energetics and biomechanics of walking," Medicine and Science in Sports and Exercise, col. 39, p. 515, Apr. 2007.

Chu, A. et al, "On the biomimetric design of the Berkeley lower extremity exoskeleton (BLEEX)", Proc. 2005 in IEEE Int. Conf. Robotics and Automation (IEEE Press, Barcelona, Spain, pp. 4356-4363 Apr. 2006).

Clevertex: Development of Strategic Master Plan for the transformation of the traditional textile and clothing into a knowledge driven industrial sector by 2015, 160 pages, dated prior to Jul. 2014.

Collins, S., et al., "Efficient Bipedal Robots Based on Passive-Dynamic Walkers," Science, vol. 307, Issue 5712, pp. 1082-1085, Feb. 18, 2005.

Cool, J.C., "Biomechanics of orthoses for the subluxed shoulder," Prosthetics & Orthotics International; vol. 13, Issue 2, pp. 90-96, 1989.

Da Silva, A. F. et al., "FBG Sensing Glove for Monitoring Hand Posture," IEEE Sensors Journal, vol. 11, Issue 10, pp. 2442-2448, Oct. 2011.

De Rossi, D. et al., "Wearable technology for biomechanics: e-textile or micromechanical sensors?" IEEE engineering in medicine and biology magazine, vol. 29, No. 3, pp. 37-43, May/Jun. 2010. [Online]. Available: http://www.ncbi.nlm.nih.gov/pubmed/20659856.

Delp, S. L. et al., "OpenSim: open-source software to create and analyze dynamic simulations of movement." IEEE transactions on bio-medical engineering, vol. 54, No. 11, pp. 1940-1950, Nov. 2007. [Online]. Available: http://www.ncbi.nlm.nih.gov/pubmed/18018689.

Dollar, A. M. et al., "Lower extremity exoskeletons and active orthoses: Challenges and state-of-the-art,", IEEE Transactions on Robotics, vol. 24, No. 1, pp. 144-158, Feb 2008.

(56) References Cited

OTHER PUBLICATIONS

Erk, K. A. et al., "Strain stiffening in synthetic and biopolymer networks," Biomacromolecules, vol. 11, No. 5, pp. 1358-1363, May 2010.
Farris D.J., et al., Human medial gastrocnemius force-velocity behavior shifts with locomotion speed and gait. Proc Natl Acad Sci USA. Jan. 2012; 109:977-982.
Ferris, D. P. et al., "Robotic lower limb exoskeletons using proportional myoelectric control," in EMBC 2009, Annual International Conference of the IEEE Engineering in Medicine and Biology Society, 2009.
Ferris, D.P. et al., A Physiologist's Perspective on Robotic Exoskeletons for Human Locomotion. Int J HR, 4(3): p. 507-528, 2007.
Ghodsi et al., De novo Likelihood-based measures for comparing genome assemblies. In: BMC Research Notes 2013, Aug. 22, 2013—online retrieved on Oct. 25, 2016.
Gibbs, P. et al.: Wearable Conductive Fiber Sensors for Multi-Axis Human Joint Angle Measurements. Journal of NeuroEngineering and Rehabilitation, Mar. 2, 2005.
Goodvin, C.I.: Development of a Real-time Spinal Motion Inertial Measurement System for Vestibular Disorder Application, University of Victoria, 155 pages, date 2003.
Gregorczyk, K. N., et al., The effects of a lower body exoskeleton load carriage assistive device on oxygen consumption and kinematics during walking with loads, in 25th Army Sci. Conf., Florida, USA, 2006.
Hallemans, A. et al.: 3D joint dynamics of walking in toddlers. A cross-sectional study spanning the first development phase of walking. Gait & Posture, 22:107-118, 2005.
Kadaba, M. P., et al., "Measurement of lower extremity kinematics during level walking." Journal of orthopaedic research: official publication of the Orthopaedic Research Society, vol. 8, No. 3, pp. 383-392, May 1990. [Online]. Available: http://www.ncbi.nlm.nih.gov/pubmed/2324857.
Kawamoto, H., et al., Power assist method for HAL-3 using EMG-based feedback controller. in Systems, Man and Cybernetics, 2003. IEEE International Conference on. 2003.
Kim, D.-H. et al., "Epidermal electronics." Science, vol. 333, No. 6044, pp. 838-843, Aug. 2011. [Online] Available: http://www.sciencemag.org/cgi/doi/10.1126/science.1206157.
Kramer, R. K. et al., "Soft curvature sensors for joint angle proprioception," in 2011 IEEE/RSJ International Conference on Intelligent Robots and Systems. IEEE, pp. 1919-1926, Sep. 2011. [Online]. Available: http://ieeexplore.ieee.org/lpdocs/epic03/wrapper.htm?arnumber=6094701.
Kramer, R. K. et al., "Wearable tactile keypad with stretchable artificial skin," 2011 IEEE International Conference on Robotics and Automation, pp. 1103-1107, May 2011. [Online]. Available: http://ieeexplore.ieee.org/lpdocs/epic03/wrapper.htm?arnumber=5980082.
Kulyukin, V A.: Advances in Human-Robot Interaction, 354 pages, Dec. 2009.
Lee, S. W. et al.: Biomimetic Approach Enables Functional Movements of Hand Post Stroke: A Pilot Study, 2 pages, dated 2012.
Lipomi, D. J. et al., "Skin-like pressure and strain sensors based on transparent elastic films of carbon nanotubes." Nature nanotechnology, vol. 6, No. 12, pp. 788-792, Jan. 2011. [Online]. Available: http://www.ncbi.nlm.nih.gov/pubmed/22020121.
Majidi, C. et al., "A non-differential elastomer curvature sensor for softer-than-skin electronics," Smart Materials and Structures, vol. 20, No. 10, p. 105017, Oct. 2011. [Online]. Available: http://stacks.iop.org/0964-1726/20/i=10/a=105017?key=crossref.0cca7e97d6ad7110bcdcaf45f30f3b60.
Malcolm, Philippe et al., Fast Exoskeleton Optimization. Science, vol. 356, Issue 6344, pp. 1230-1231, Jun. 23, 2017.
Mattila, H. R., Intelligent textiles and clothing, Woodhead Publishing Limited, 525 pages, © 2006.
McGeer, T., Passive Bipedal Running. Proceedings of the Royal Society of London. Series B, Biological Sciences, 240(1297): p. 107-134, May 1990.
Newman, D. J. et al., Astronaut Bio-Suit System to Enable Planetary Exploration. In International Astronautical Conference, Vancouver, Canada, Oct. 2004.
Park, Y. L. et al., Active Modular Elastomer Sleeve for Soft Wearable Assistance Robots, 2012 IEEE/RSJ International Con. on Intelligent Robots and Systems Vilamoura, Algarve, Portugal, 8 pages, Oct. 7-12, 2012.
Park, Y.-L., et al., "Design and Fabrication of Soft Artificial Skin Using Embedded Microchannels and Liquid Conductors," IEEE Sensors Journal, vol. 12, No. 8, pp. 2711-2718, Aug. 2012. [Online]. Available: http://ieeexplore.ieee.org/lpdocs/epic03/wrapper.htm?arnumber=6203551.
Park, Y.-L., "Hyperelastic pressure sensing with a liquid-embedded elastomer," Journal of Micromechanics and Microengineering, vol. 20, No. 12, p. 125029, Dec. 2010. [Online]. Available: http://stacks.iop.org/0960-1317/20/i=12/a=125029?key=crossref.84cffc44789ba7bde0bodfd169e25af91.
Park, Y.-L., et al.: Bio-inspired Active Soft Orthotic Device for Ankle Foot Pathologies, 2011 IEEE/RSJ International Conference on Intelligent Robots and Systems, San Francisco, CA, USA, 8 pages, Sep. 25-30, 2011.
Pereira da Fonseca, P. F.: Validation of two types of textile electrodes for electrocardiography and electromyography measurement applications, 126 pages, dated Jul. 2012.
Polonen et al. Automatic Intensity Quantification of Fluorescence Targets from microscope Images with Maximum Likelihood Estimation. 17th European Signal Processing Conference, Aug. 24-28, 2009—retrieved online Oct. 25, 2016.
Pratt, J. et al., The RoboKnee: An exoskeleton for enhancing strength and endurance during walking, in IEEE Int. Conf. Robotics and Automation (ICRA), New Orleans, USA (IEEE Press), pp. 2430-2435, Apr. 2004.
Quintero, H. A. et al., "Control and Implementation of a Powered Lower Limb Orthosis to Aid Walking in Paraplegic Individuals," in IEEE International Conference on Rehabilitation Robotics, Switzerland, pp. 1-6, Jun. 29-Jul. 1, 2011.
Ramuz, M. et al., "Transparent, Optical, Pressure-Sensitive Artificial Skin for Large-Area Stretchable Electronics," Advanced Materials , May 2012. [Online]. Available: http://doi.wiley.com/10.1002/adma.201200523.
Reid, S. A. et al., "Biomechanical assessment of rucksack shoulder strap attachment location: effect on load distribution to the torso," presented at the RTO HFM specialists' Meeting on "Soldier Mobility: Innovations in Load Carriage System Design and Evaluation," NATO-RTO Meeting Proceedings: MP-056 (Neuilly-sur-Seine: NATO). Jun. 1-6, 2000.
Royer, T.D. et al., (2005) Manipulations of Leg Mass and Moment of Inertia: Effects on Energy Cost of Walking, Medicine & Science in Sports & Exercise, vol. 37. No. 4: p. 649-656, 2005.
Salvendy, G.: Smart Clothing Technology and Applications, Human Factors and Ergonomics, by Taylor and Francis Group, LLC, 290 pages, © 2010.
Schiele, A. "Ergonomics of Exoskeletons: Objective Performance Metrics" in Euro Haptics conference and symposium on Haptic Interfaces for Virtual Environmental Teleoperator Systems, Salt Lake City, UT, USA, Mar 2009.
Scilingo, E. P. et al., "Strain-sensing fabrics for wearable kinaesthetic-like systems," IEEE Sensors Journal, vol. 3, No. 4, pp. 460-467, Aug 2003. [Online]. Available: http://ieeexplore.ieee.org/lpdocs/epic03/wrapper.htm?arnumber=1226639.
Silva, H. R., et al.: Wireless Hydrotherapy Smart-Suit Network for Posture Monitoring, 5 pages, dated 2007.
Strauser, K. A. et al., "The development and testing of a human machine interface for a mobile medical exoskeleton" in IEEE Int Conf, Intelligent Robots and Systems, San Francisco, CA. USA, Sep. 2011.
Tesconi, M., et al., "Wearable sensorized system for analyzing the lower limb movement during rowing activity," 2007 IEEE International Symposium on Industrial Electronics, pp. 2793-2796, Jun 2007. [Online]. Available: http://ieeexplore.ieee.org/lpdocs/epic03/wrapper.htm?arnumber=4375052.
Tiwana, M. I., et al., "A review of tactile sensing technologies with applications in biomedical engineering," Sensors and Actuators A:

(56) References Cited

OTHER PUBLICATIONS

Physical, vol. 179, pp. 17-31, Jun 2012. [Online]. Available: http://linkinghub.elsevier.com/retrieve/pii/S0924424712001641.
Vogt, D. M., et al., Design and Characterization of a Soft Multi-Axis Force Sensor Using Embedded Microfludic Channels, IEEE Sensors Journal, vol. 13. No. 10, 9 pages, Oct 2013.
Walsh, C. J., et al., A Quasi-Passive Leg Exoskeleton for Load Carrying Augmentation. International Journal of Humanoid Robotics, Special Issue: Active Exoskeletons, 4(3): 487-506, 2007.
Wehner, M., 2012 "Man to Machine, Applications in Electromyography," EMG Methods for Evaluation Muscle and Nerve Functions. Intech Publishing, Sep. 13, 2012 http://intechopen.com/articles/show/title/man-to-machine-applications-in-electromyography.
Wehner, M., et al., "Experimental characterization of components for active soft orthotics," in Proc. IEEE Int. Conf. Biomed. Rob. Biomechatron., Roma, Italy, Jun. 2012.
Wehner, M., et al., "Lower Extremity Exoskeleton Reduces Back Forces in Lifting" ASME Dynamic Systems and Control Conference, Hollywood, California, USA pp. 49-56, Oct. 12-14, 2009.
Woodman, O.J. "An introduction to inertial navigation," Technical Report UCAM-CL-TR-696, Aug. 2007.
Yamada, T. et al., "A stretchable carbon nanotube strain sensor for human-motion detection." Nature Nanotechnology, vol. 6, No. 5 pp. 296-301, May 2011. [Online]. Available: http://ncbi.nlm.nih.gov/pubmed/21441912.
Zhang, R. et al., "Carbon nanotube polymer coatings for textile yarns with good strain sensing capability," Sensors and Actuators A: Physical, vol. 179, pp. 83-91, Jun 2012. [Online]. Available: http://linkinghub.elsevier.com/retrieve/pii/S0924424712001938.
Zhang, Juanjuan et al., Human-in-the-Loop Optimization of Exoskeleton Assistance During Walking, Science, vol. 356, pp. 1280-1284, Jun. 23, 2017.
Zoss, A.B., et al., Biomechanical design of the Berkeley lower extremity exoskeleton (BLEEX), IEE/ASME Transactions on Mechatronics, 11(2): p. 128-138, Apr. 2006.
PCT International Search Report, issued in International Application No. PCT/EP2003/012123, dated Jun. 22, 2004.
PCT International Search Report and Written Opinion, issued in International Application No. PCT/US2013/060225, dated May 27, 2014.
PCT International Search Report and Written Opinion, issued in International Application No. PCT/US2014/040340, dated Oct. 31, 2014.
PCT International Search Report and Written Opinion, issued in International Application No. PCT/US2014/068462, dated May 22, 2015.
PCT International Search Report and Written Opinion, issued in International Application No. PCT/US2015/014672, dated Jul. 6, 2015.
PCT International Search Report and Written Opinion, issued in International Application No. PCT/US2015/025472, dated Sep. 4, 2015.
PCT International Search Report and Written Opinion, issued in International Application No. PCT/US2015/051107 dated Aug. 5, 2016.
PCT International Search Report and Written Opinion, issued in International Application No. PCT/US2016/049706 dated Nov. 29, 2016.
Extended European Search Report issued in European Application No. 13871010.8 dated Sep. 2, 2016.
PCT International Search Report and Written Opinion, issued in International Application No. PCT/US2017/022150 dated Jun. 9, 2017.
Extended European Search Report issued in European Application No. 14803880.5 dated May 19, 2017.

\* cited by examiner

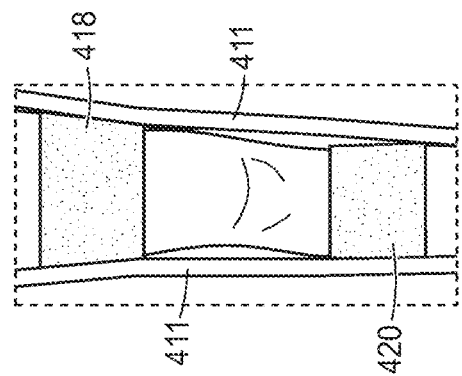
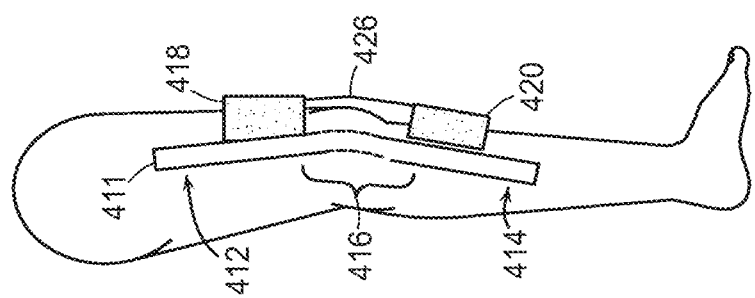
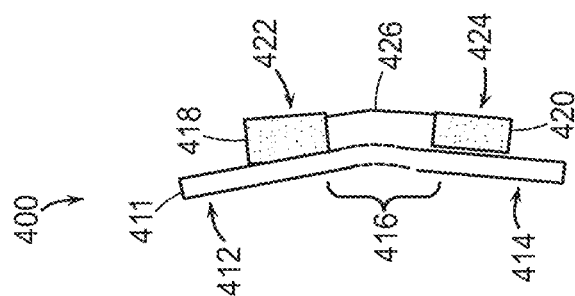

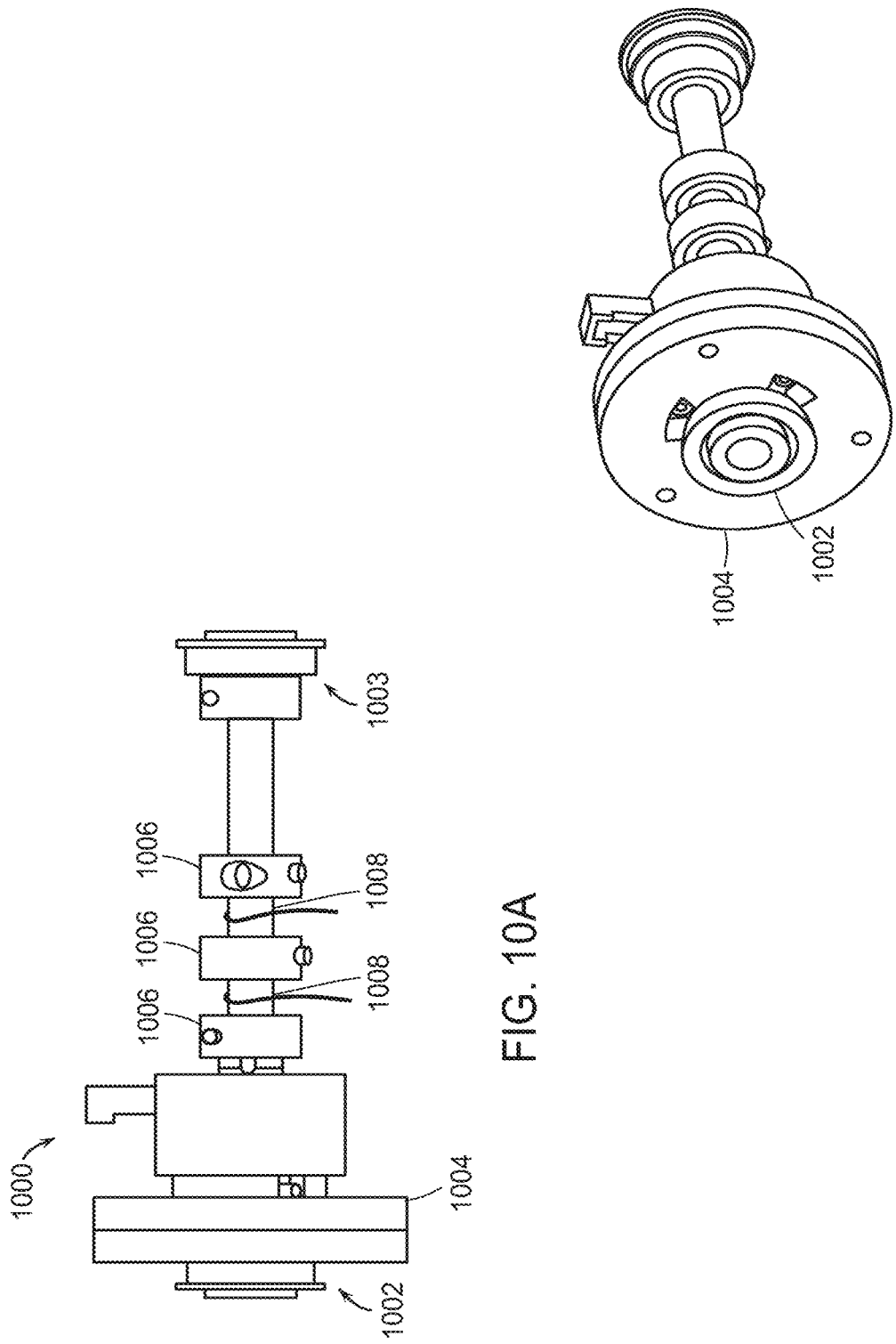

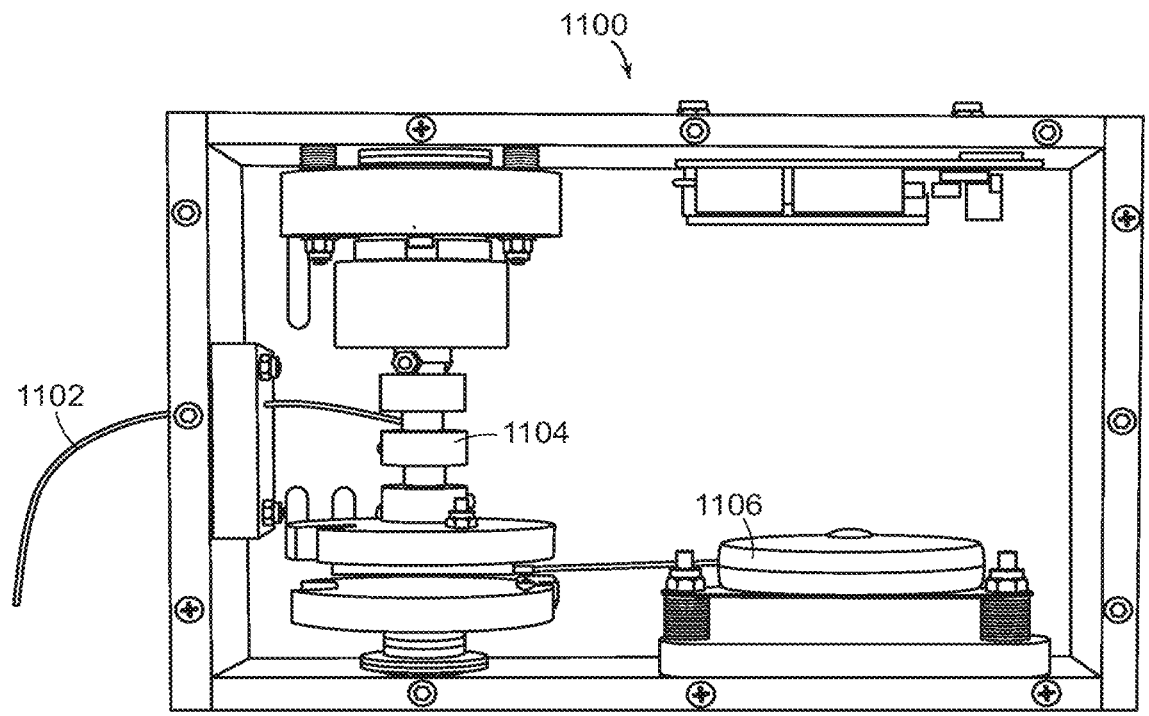
FIG. 11
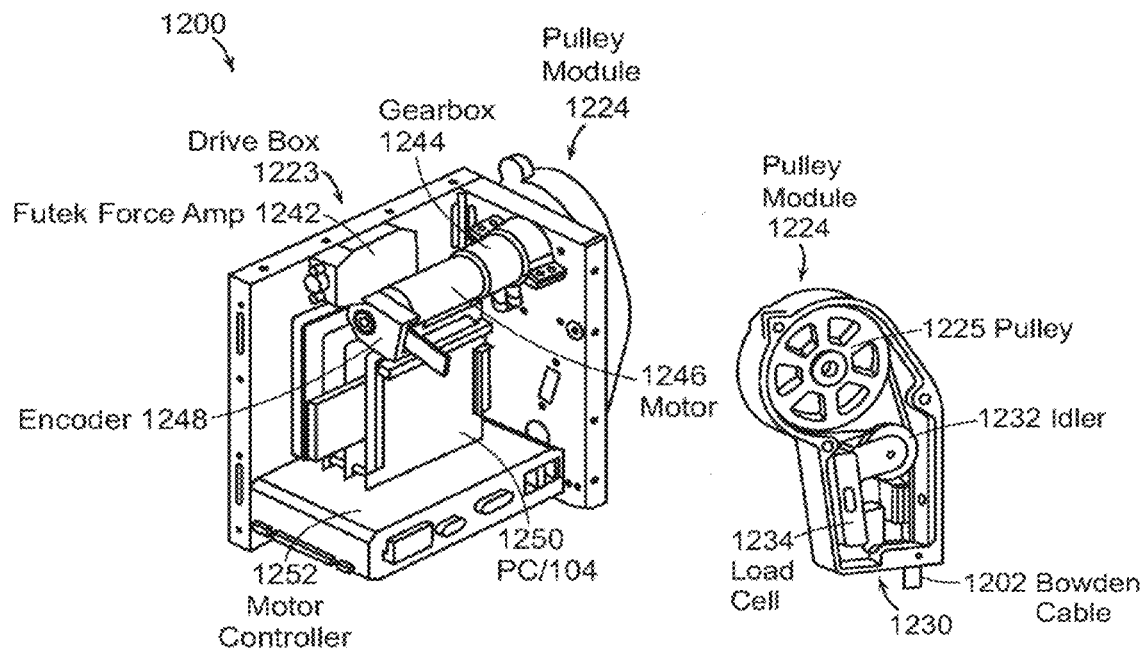
FIG. 12A
FIG. 12B

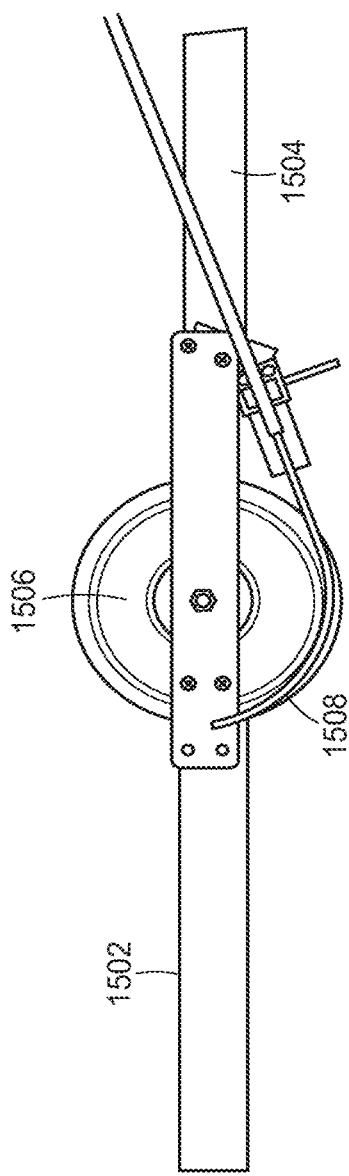
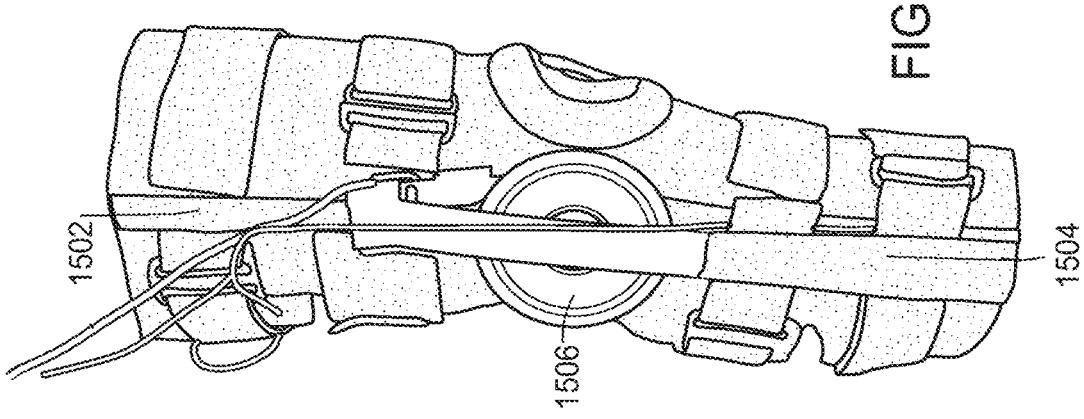
FIG. 15B
FIG. 15A

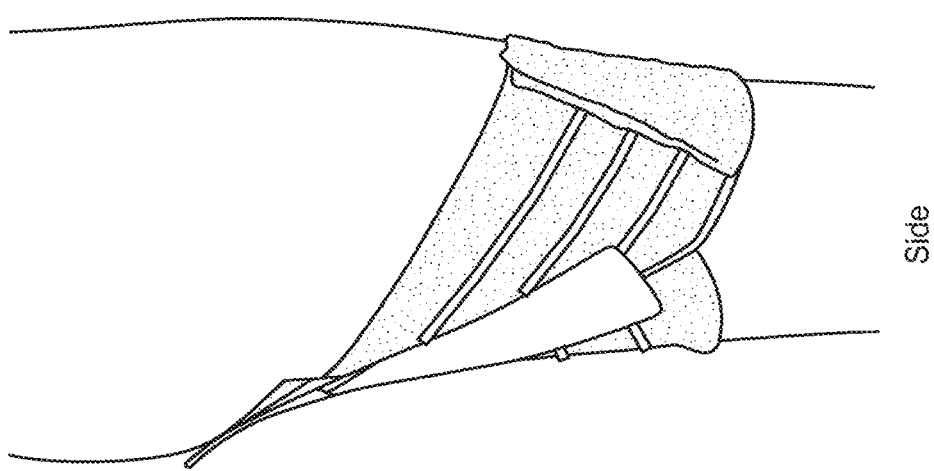
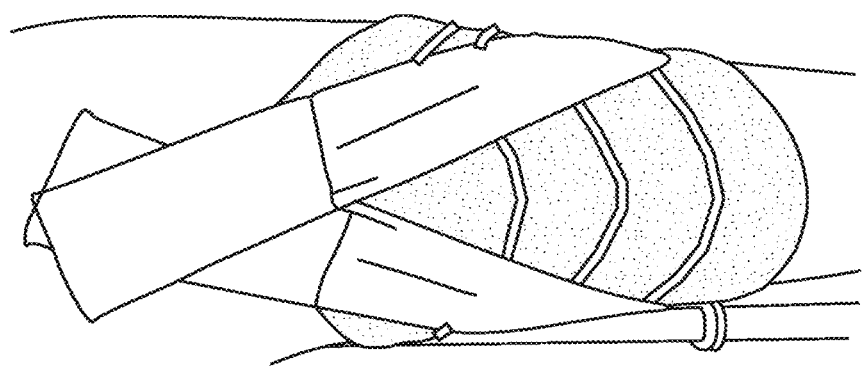
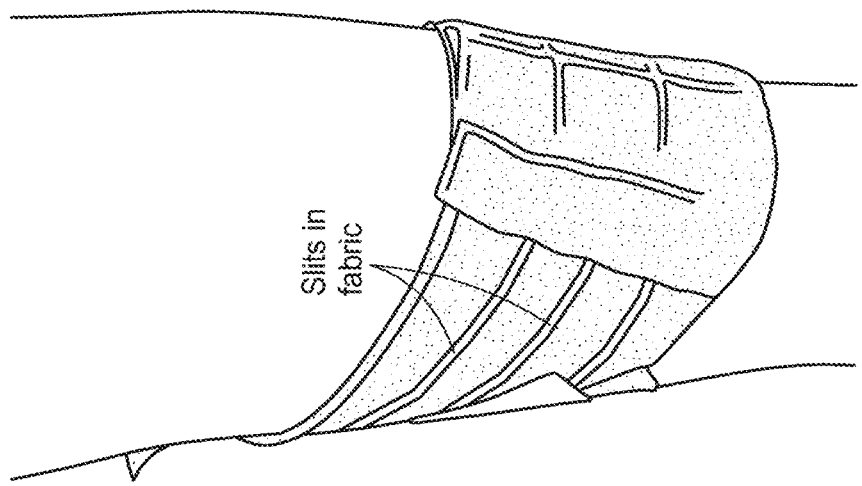
FIG. 31C Side
FIG. 31B Back
FIG. 31A Front-Side
Slits in fabric

ORTHOPEDIC DEVICE INCLUDING PROTRUDING MEMBERS

CROSS-REFERENCES TO RELATED APPLICATIONS

This application is a U.S. national phase application of PCT International Patent Application No. PCT/US2015/025472, filed on Apr. 10, 2015, titled, "ORTHOPEDIC DEVICE INCLUDING PROTRUDING MEMBERS", which claims priority to U.S. provisional application Ser. No. 61/977,880, filed on Apr. 10, 2014, entitled "KNEE EXOSKELETON AND DOWNHILL WALKING DEVICE," U.S. provisional application Ser. No. 62/138,848, filed on Mar. 26, 2015, entitled "WEARABLE DEVICE TO ASSIST ELDERLY IN WALKING UP STAIRS AND INCLINES," and U.S. provisional application No. 61/980,961, entitled "SOFT EXOSUIT FOR ASSISTING THE LOWER BODY" filed on Apr. 17, 2014, each of which is hereby incorporated herein by reference in its entirety.

BACKGROUND

Standard knee braces worn following knee injuries generally support the knee in the body's frontal plane. However, they are not helpful for supporting and buffering the knee against motion in the body's sagittal plane. Electric generators worn during walking generally provide resistive torques only when the knee is in motion. However, this is not useful for motion in the sagittal plane, e.g., lowering the body slowly during hiking, or lifting the body again. The need for an orthopedic device to buffer motion in a direction of rotation of a joint would be helpful for not just the knee, but also applies to other body parts.

SUMMARY

The Inventors have recognized and appreciated that an orthopedic device that provides for control of movement in both the coronal plane and in the sagittal plane would be beneficial. The Inventors have recognized and appreciated that an orthopedic device that provides for control of the rotation of a joint at rest and/or in action would be beneficial. In view of the foregoing, various embodiments are directed generally to orthopedic devices and methods, apparatus, and systems for using the orthopedic devices, that facilitate control of the rotation of a joint at rest and/or in action.

This instant disclosure provides example systems, apparatus, and methods that facilitate control of the rotation of a joint at rest and/or in action. Non-limiting example embodiments relate to a knee exoskeleton adapted to providing assistance for uphill walking, downhill walking, lifting, and/or muscle weakness.

Example systems, methods, and apparatus herein provide an orthopedic device that includes a pair of base mechanisms for positioning along opposite sides of a body, a control system, and at least one powered element. Each base mechanism includes a base portion having a rigid first end, a rigid second end, and a central region. The central region of the base portion is for positioning proximate to an axis of rotation of a joint of the body. The central region comprises a series of at least three links that each enable rotation of the rigid first end with respect to the rigid second end within at least one quadrant and that each prevent rotation of the rigid first end with respect to the rigid second end within at least two other quadrants. Each base mechanism also includes a first anterior protrusion extending from the first end of the base portion, proximate to the central region, toward an anterior side of the axis of rotation of the joint to a first pivot point; a second anterior protrusion extending from the second end of the base portion, proximate to the central region, toward an anterior side of the axis of rotation of the joint to a second pivot point; and a cable coupled to the first pivot point and the second pivot point. The control system receives input from at least one sensor indicating an occurrence of at least one event in a movement of a wearer of the orthopedic device and generates a responsive control signal. The at least one powered element receives the responsive control signal from the control system and, in response, controls a tensile force through the cable between the first pivot point and the second pivot point of each base mechanism to produce beneficial forces in the pair of base mechanisms that are translated to the wearer.

Example systems, methods, and apparatus herein also provide an orthopedic device that includes a pair of base mechanisms for positioning along opposite sides of a limb including a joint. Each base mechanism includes a base portion for positioning along a side of a limb, the base portion having a rigid first end, a rigid second end, and a central region. The central region of the base portion is for positioning proximate to an axis of rotation of a joint of the limb. The central region enables rotation of the rigid first end with respect to the rigid second end. Each base mechanism also includes a first anterior protrusion, configured to extend toward an anterior side of the axis of rotation of the joint, from the first end of the base portion proximate to the central region to a first pivot point; a second anterior protrusion, configured to extend toward an anterior side of the axis of rotation of the joint, from the second end of the base portion proximate to the central region to a second pivot point; a cable coupled to the first pivot point and the second pivot point and capable of exerting a tensile force between the first anterior protrusion and the second anterior protrusion; and at least one resilient component selected from the group consisting of a first resilient component coupled to the first anterior protrusion and configured to apply a force to the first anterior protrusion and a second resilient component coupled to the second anterior protrusion and configured to apply a force to the second anterior protrusion. The base portion is coupled to the limb such that the force from the at least one resilient component is capable of applying a torque to the limb.

Example systems, methods, and apparatus herein also provide an orthopedic device that includes two rigid components, including a medial rigid component for positioning along a medial side of a limb including a joint; and a lateral rigid component for positioning along a lateral side of the limb. Each of the two rigid components includes a base portion for positioning along the limb, two protrusions, at least two cables, and at least two resilient elements. The base portion includes a rigid first end, a rigid second end, and a central region, where the central region enables rotation of the rigid first end with respect to the rigid second end. The two protrusions include a first protrusion extending from the rigid first end along the plane of flexion of the limb to a first pivot point, and configured to rotate with respect to the rigid first end; and a second protrusion extending from the rigid second end along the plane of flexion of the limb to a second pivot point, and configured to rotate with respect to the rigid second end. Each of the at least two cables is coupled to the respective first protrusion and second protrusion of each of the two rigid components, for regulating a separation between the respective first protrusion and second protrusion. The at least two resilient elements include a first resilient component that couples to the first pivot point of the medial rigid component and is configured to apply a force to the first pivot point; and a second resilient component that couples to the first pivot point of the lateral rigid component and is configured to apply a force to the second pivot point. The force from the at least two resilient elements is capable of applying a torque to the limb.

Example methods according to the principles herein for regulating an amount of force translated to a limb including a joint include positioning any of the orthopedic devices herein along the limb, such that the central portion of each of the two rigid components is positioned proximate to an axis of rotation of a joint of the limb; using at least one processing unit to compute an angle of bending of flexion or extension of the limb; and using the at least one processing unit to transmit instructions to cause a clutch coupled to the at least two cables to regulate the separation between the respective two protrusions of each of the two rigid components, thereby regulating the amount of force translated to the limb.

Example systems, methods, and apparatus herein also provide an orthopedic device that includes two resilient components for positioning along a first side or a second side of a limb including a joint, the second side being opposite to the first side, a pulley system including at least one cable, and an interface that couples the resilient components to the limb. The resilient components include a proximal resilient component for positioning along a proximal portion of the limb; and a distal resilient component for positioning along a distal portion of the limb. The pulley system is coupled to the proximal resilient component and the distal resilient component such that the pulley system is configured to restrict a rotation between the two resilient components on receiving a signal indicating that the limb is in flexion, to cause the resilient components to deform, thereby storing an amount of potential energy. The interface causes the resilient components to apply an amount of a force, based on the stored potential energy, to cause an amount of extension of the limb.

Example systems, methods, and apparatus herein also provide an orthopedic device that includes a resilient member, an actuator unit or a clutch coupled to the intersection portion of the resilient member, and an interface that couples the resilient member to the limb. The resilient member includes a medial resilient component for positioning along a medial side of a limb including a joint; and a lateral resilient component for positioning along a lateral side of the limb. The medial resilient component and the lateral resilient component each extend from a distal portion of the limb to a proximal portion of the limb past the joint, and are configured to extend toward an anterior side of the proximal portion of the limb. The medial resilient component and the lateral resilient component meet to form an intersection portion proximate to the proximal portion of the limb. The actuator unit or a clutch is coupled to the intersection portion of the resilient member, where the actuator unit or the clutch is configured to restrict a movement of the intersection portion on receiving a signal indicating that the limb is in flexion, thereby causing the resilient member to deform to store an amount of potential energy. The interface couples the resilient member to the limb to cause the resilient components to apply an amount of force, based on the stored potential energy, to cause an amount of extension of the limb.

Example systems, methods, and apparatus herein also provide an orthopedic device that includes two rigid components for positioning along a medial side or a lateral side of a limb including a joint, and a pulley system including at least one cable. The two rigid components include a proximal rigid component for positioning along a proximal portion of the limb; and a distal rigid component for positioning along a distal portion of the limb. The pulley system is coupled to the proximal rigid component and the distal rigid component such that the pulley system causes a tensile force to be applied to at least one of the two rigid components, to cause a rotation of the proximal portion of the limb relative to the distal portion of the limb about the joint, thereby applying a force to cause a degree of a flexion or an extension of the limb.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 1A-9B show example orthopedic devices, according to the principles herein.

FIGS. 10A and 10B show an example electromagnetic clutch, according to the principles herein.

FIG. 11 shows an example clutch box, according to the principles herein.

FIGS. 12A and 12B show an example actuator unit, according to the principles herein.

FIGS. 13A-15B show example orthopedic devices, according to the principles herein.

FIGS. 27A-32D show portions of example interfaces, according to the principles herein.

DETAILED DESCRIPTION

Figure 1A:
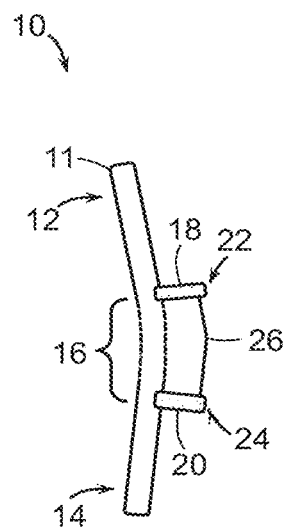

Following below are more detailed descriptions of various concepts related to, and embodiments of, inventive methods, apparatus, and systems that facilitate control of the rotation of a joint at rest and/or in action. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, and the term "including" means including but not limited to. The term "based on" means based at least in part on.

With respect to substrates or other surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a substrate or a layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the substrate (or other surface) and each other. The terms "disposed on" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

As used herein, the term "limb" encompasses the arm or leg of a human, the fore- or hind-limbs of non-human animal (such as but not limited to a cat, or a dog, etc.), or the wing of a bird.

As used herein, the "medial side" of a limb refers to the side of the limb closest to the other limb of the pair (e.g., pair of forelimbs, pair of hind limbs, pair of arms, pair of legs).

As used herein, the "lateral side" of the limb refers to the side of the limb opposite to the medial side.

As used herein, a "rigid" material refers to a material that displays a stiffness ranging from highly unyielding to more pliant or somewhat flexible materials. A "rigid" material herein refers to materials with a value of Young's modulus greater than or equal to about 0.1 GPa. In an example, a material at the lower end of this range of Young's modulus, or possibly even lower than about 0.1 GPa, could be considered a "rigid" material. For example, a material having a value of Young's modulus less than about 0.1 GPa can be considered a "rigid" material if it is used to form a rigid end, a rigid component, or other rigid structure having dimensions perpendicular to the axis of bending of a limb (or other body segment) that is sufficiently large, such that the rigid end, rigid component, or other rigid structure exhibits little deflection under the applied loads, or if, when attached to the limb (or other body segment), the rigid end, a rigid component, or other rigid structure are supported sufficiently to exhibit little deflection. As a non-limiting example, the little deflection can be considered deflection of less than about 2.0 to about 3.0 cm.

As used herein, a "passive element" refers to a device element that is not powered and that can be used for energy storage, such as but not limited to a spring, an elastic element, an artificial exotendon, or other compliant material.

As used herein, a "powered element" refers to a device element that is powered using a power supply, including device elements powered via on-board or off-board power supplies. Non-limiting examples of powered elements include an actuator (such as but not limited to a cable drive, a pneumatic actuator, etc.) and a controllable clutch.

Systems, methods, and apparatus herein are directed to orthopedic devices that provide supportive forces at the joint of a limb as a function of joint angle for such movement as lowering and raising the body, as compared to just as a function of velocity.

In some example, the orthopedic devices uses springs to store energy and release it as opposed to requiring force from a motor, as with some existing orthopedic devices. The example devices easily combine the integration of dampers with springs for more flexibility in modulating and controlling the impedance at the joint.

An example system, method, and apparatus herein provides orthopedic devices that can automatically align with a user's biological joint at the knee with a simple mechanism.

FIG. 1A shows an example base mechanism 10 of an orthopedic device according to the principles described herein. The example base mechanism 10 includes a base portion 11 having a rigid first end 12, a rigid second end 14, and a central region 16. The central region 16 of the base portion 11 is configured to facilitate rotation of the rigid first end 12 relative to the rigid second end 14. The example base mechanism 10 includes a protrusion 18 that extends from the first end 12 of the base portion 11 to a pivot point 22. The example base mechanism 10 also includes a protrusions 20 that extends from the second end 14 of the base portion 11 to a pivot point 24. The example base mechanism 10 also includes a cable 26 that couples pivot point 22 of protrusion 18 to pivot point 24 of protrusion 20. The example base mechanism 10 is coupled to at least one powered element and a control system that receives input from at least one sensor indicating an occurrence of at least one event in a movement of a wearer of the example orthopedic device and generates a responsive control signal. The at least one powered element receives the responsive control signal from the control system and, in response, controls a tensile force through the cable 26 between the pivot points 22 and 24 to produce beneficial forces in the base mechanism, which can be translated to the wearer.

In an example, the at least one powered element is configured to control the tensile force through the cable 26 upon an indication of at least one signal, responsive to the one or more predefined events occurring during movement of the wearer of the orthopedic device. The control of the extension of the cable 26 can cause a control of the tensile forces through the cable 26 to generate beneficial forces at the base portion 11, which can be translated to the wearer.

In one example, the control of the tensile force through cable 26 between the pivot points 22 and 24 reduces a maximum separation between pivot points 22 and 24. In one example, the control of the tensile force through cable 26 between the pivot points 22 and 24 provide resistance that limits a maximum separation between pivot points 22 and 24. In one example, the control of the tensile force through cable 26 between the pivot points 22 and 24 provides resistance that allows an increased maximum separation between pivot points 22 and 24. In one example, the control of the tensile force through cable 26 between the pivot points 22 and 24 produces no resistance to an increase in the maximum separation between pivot points 22 and 24.

In a non-limiting example where the orthopedic device is positioned at a leg of a wearer, the at least one powered element can be configured to apply a desired magnitude of tensile force between protrusions 18 and 20, or to impose a maximum allowable separation between pivot points 22 and 24, upon an indication of at least one signal that the wearer is at certain points in the gait cycle. The at least one powered element can be configured to reduce or eliminate the tensile force acting on the cable 26 or to eliminate the restriction on maximal separation between pivot points 22 and 24, to allow for increased separation between the pivot points 22 and 24 at certain other points during the gait cycle.

Figure 1B:
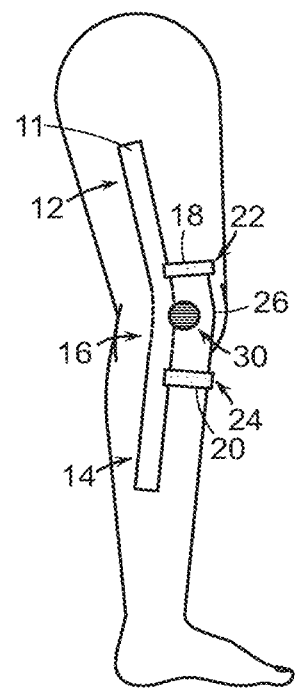

FIG. 1B shows an example base mechanism 10 of an orthopedic device according to the principles described herein, that is coupled to a limb of a wearer. In this non-limiting example, the limb is a leg. However, in other examples, the example orthopedic device can be applied to other limbs (including arms) or other body segments that include a joint (including the shoulder/arm joint, or the joint coupling the pelvic region and the thigh/femur). As shown in FIG. 1B, the example base mechanism 10 of the orthopedic device can be disposed about the limb such that the base portion 11 is positioned along a side of the limb, and a portion of the central region 16 is positioned proximate to the axis of rotation 30 of a joint of the limb. The example base mechanism 10 is configured such that the protrusions 18 and 20 extend towards an anterior side in the sagittal plane of the axis of rotation 30. According to the principles herein, the example base mechanism 10 is coupled to the limb of the wearer such that a tensile force exerted using the cable 26 can cause a torque to be exerted on the limb about the axis of rotation 30.

An example orthopedic device according to the principles herein can include a base mechanism 10 disposed at a side of the limb of the wearer, such as shown in FIG. 1B.

Another example orthopedic device according to the principles herein can include two base mechanisms 10, each configured to be disposed at opposite sides of the limb of the wearer. For example, the orthopedic device can include a medial base mechanism (based on base mechanism 10) for positioning along a medial side of the limb, and a lateral base mechanism (based on base mechanism 10) for positioning along a lateral side of the limb, substantially opposite to the first side.

Figure 2A:
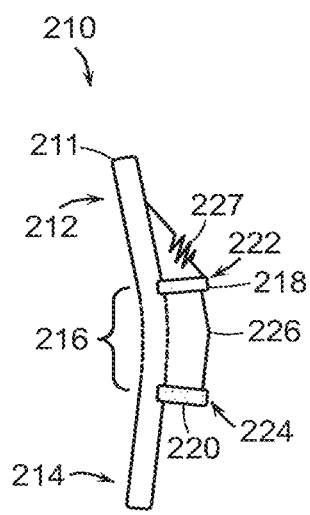

FIG. 2A shows another example base mechanism 210 of an orthopedic device according to the principles described herein. The example base mechanism 210 includes a base portion 211 having a rigid first end 212, a rigid second end 214, and a central region 216. The central region 216 of the base portion 211 is configured to facilitate rotation of the rigid first end 212 relative to the rigid second end 214 about a portion of the central region 216. The example base mechanism 210 includes a protrusion 218 that extends from the first end 212 of the base portion 211 to a pivot point 222. The example base mechanism 210 also includes a protrusion 220 that extends from a second end 214 of the base portion 211 to a pivot point 222. The example base mechanism 210 also includes a cable 226 that couples pivot point 222 of protrusion 218 to pivot point 224 of protrusion 220.

Figure 2B:
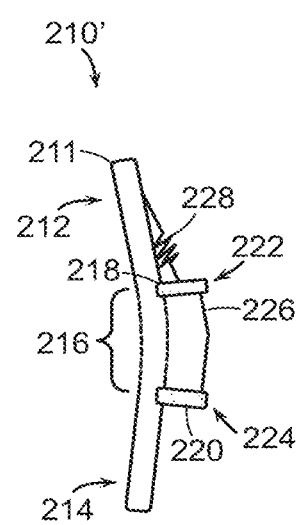
Figure 2C:
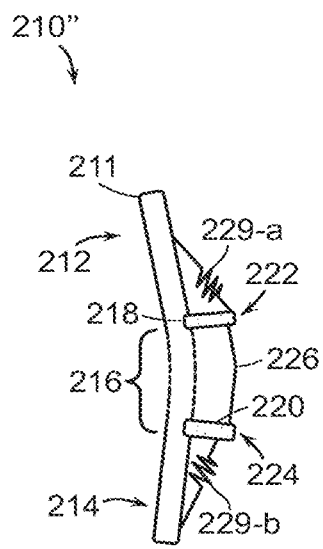

Example base mechanism 210 also includes at least one resilient component that operates in cooperation with the cable 226 and the protrusions 218 and 220 to apply torques to body segments about the axis of rotation of a joint of the body segments. The example base mechanism 210 can be configured such that the at least one resilient component couples the base portion to at least one of the protrusions. The example of FIG. 2A shows a base mechanism 210 that includes a resilient component 227 coupling a first end 212 of base portion 211 to pivot point 222 of protrusion 218. FIG. 2B shows another example base mechanism 210' that includes a resilient component 228 coupling the first end 212 of base portion 211 to a different portion of protrusion 218 (i.e., a point along the mid-section of protrusion 218). FIG. 2C shows another example base mechanism 210" that includes two resilient components 229-a and 229-b. Resilient component 229-a couples the first end 212 of base portion 211 to pivot point 222 of protrusion 218, while resilient component 229-b couples the second end 214 of base portion 211 to pivot point 224 of protrusion 220. While the example of FIG. 2C shows both resilient components 229-a and 229-b coupled to the pivot point of a protrusion, at least one of resilient components 229-a and 229-b could be coupled to a different portion of a protrusion (such as but not limited to a point along the mid-section of the protrusion).

In any of the example orthopedic devices described in connection with FIGS. 2A through 2C, the example base mechanism 210, 210' or 210" can be coupled to at least one powered element and a control system that receives input from at least one sensor indicating an occurrence of at least one event in a movement of a wearer of the example orthopedic device and generates a responsive control signal. The at least one powered element receives the responsive control signal from the control system and, in response, controls a tensile force through the cable 226 between the pivot points 222 and 224 to produce beneficial forces in the base mechanism. which can be translated to the wearer.

In an example, the at least one powered element is configured to control the extension of the cable 226 between the pivot points 222 and 224. The at least one powered element can be configured to control the extension of the cable 226 upon an indication of at least one signal, responsive to the one or more predefined events occurring during movement of the wearer of the orthopedic device. The control of the extension of the cable 226 causes a control of the tensile forces through the cable 226 to generate beneficial forces at the base portion 211 during movement of the wearer.

In various examples, the control of the tensile force through the cable 226 between the pivot points 222 and 224 can limit a maximum separation and/or limit a rate of change of a maximum separation between pivot points 222 and 224. In various examples, the control of the tensile force through the cable 226 between the pivot points 222 and 224 may not limit a maximum separation and/or not limit a rate of change of a maximum separation between pivot points 222 and 224.

In a non-limiting example where the orthopedic device is positioned at the leg of a wearer, the at least one powered element can be configured to apply a desired magnitude of tensile force between protrusions 218 and 220, or to limit a maximum separation between pivot points 222 and 224, upon an indication of at least one signal that the wearer is at certain points in the gait cycle. The at least one powered element can be configured to reduce or eliminate the tensile force acting on the cable 226 or to eliminate the restriction on a maximal separation between pivot points 222 and 224, to allow for increased separation between the pivot points 222 and 224 at certain other points during the gait cycle.

Figure 2D:
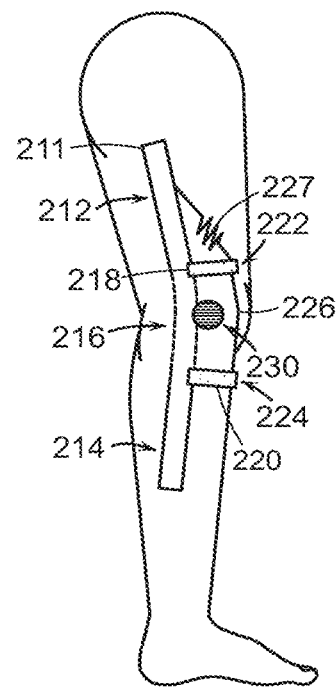

FIG. 2D shows the example base mechanism 210 of the orthopedic device of FIG. 2A coupled to a limb of a wearer. In this non-limiting example, the limb is a leg. However, in other examples, the example orthopedic device can be applied to other limbs (including arms) or other body segments that include a joint (including the shoulder/arm joint, or the joint coupling the pelvic region and the thigh/femur). As shown in FIG. 2D, the example base mechanism 210 of the orthopedic device can be disposed about the limb such that the base portion 211 is positioned along a side of the limb, and a portion of the central region 216 is positioned proximate to the axis of rotation 230 of a joint of the limb. The example base mechanism 210 is configured such that the protrusions 218 and 220 extend towards an anterior side in the sagittal plane of the axis of rotation 230. According to the principles herein, the example base mechanism 210 is coupled to the limb of the wearer such that a tensile force exerted using the cable 226 and the resilient component 227 can cause a torque to be exerted on the limb about the axis of rotation 230. While the description is made relative to the example base mechanism 210 of FIG. 2A, it also applies to example base mechanisms 210' and 210" of FIGS. 2B and 2C, respectively.

An example orthopedic device according to the principles herein can include a base mechanism 210 (or 210' or 210") disposed at a side of the limb of the wearer, such as shown in FIG. 2D for base mechanism 210.

Another example orthopedic device according to the principles herein can include two base mechanisms (any of base mechanisms 210 and/or 210' and/or 210"), each configured to be disposed at opposite sides of the limb of the wearer. For example, the orthopedic device can include a medial base mechanism (based on any of base mechanisms 210 and/or 210' and/or 210") for positioning along a medial side of the limb, and a lateral base mechanism (based on any of base mechanisms 210 and/or 210' and/or 210") for positioning along a lateral side of the limb, substantially opposite to the first side.

In any of the example orthopedic devices according to the principles herein, the central region of the base portion enables the rotation of the rigid first end relative to the rigid second end. In any of the example orthopedic devices according to the principles herein, the central region of the base portion enables the rotation of the rigid first end relative to the rigid second end in at least one quadrant. In some of the example orthopedic devices according to the principles herein, the central region of the base portion may not enable the rotation of the rigid first end relative to the rigid second end in one quadrant. In some of the example orthopedic devices according to the principles herein, the central region of the base portion may not enable the rotation of the rigid first end relative to the rigid second end in two quadrants.

Figure 3A:
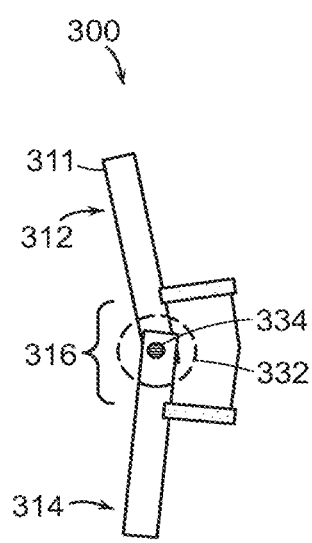

For example, as shown in FIG. 3A, example base mechanism 300 can includes a base portion 311 having a central region 316 that enables rotation of the rigid first end 312 relative to the rigid second end 314. In the example shown in FIG. 3A, the central region 316 comprises a hinged region 332 that enables rotation. In this example, the rigid first end 312 is coupled to the rigid second end 314 via a hinge 334. Hinge 334 may enable rotation through all quadrants. Alternatively, hinge 334 may prevent rotation in one or two quadrants.

Figure 3B:
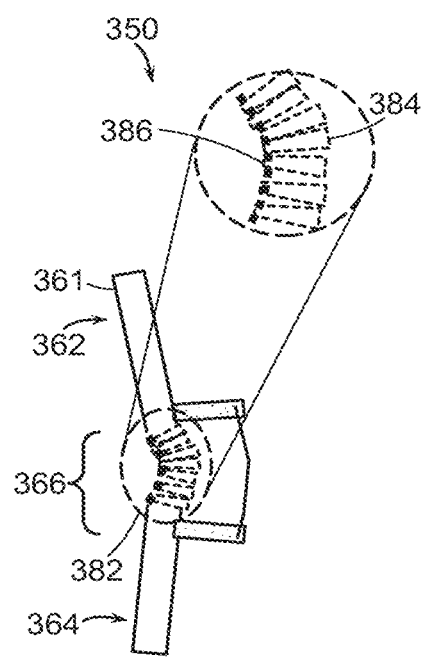

As shown in FIG. 3B, example base mechanism 350 can include a base portion 361 having a central region 366 that enables rotation of the rigid first end 362 relative to the rigid second end 364. In the example shown in FIG. 3B, the central region 366 comprises a flexible portion 382 that enables rotation. The flexible portion 382 can include two of more linking members 384 that are configured to facilitate an amount of rotation relative to each other (see magnified region of FIG. 3B). The example linking members 384 can be coupled to each other using a linking component 386, such as but not limited to a flexible backing or pin structures. In another example, the flexible portion of the central region can be formed from a material that can be deformed elastically or otherwise reproducible during actuation, such as but not limited to a shape memory alloy material, a polymeric material, or an elastic flexible material.

In embodiments of the invention in which a central region of a base mechanism uses a plurality of elements that are each capable of enabling rotation, each element that is capable of enabling rotation may only enable a limited range of rotation. In embodiments of the invention in which a central region of a base mechanism uses a plurality of elements that are each capable of enabling rotation, each element that is capable of enabling rotation may also prevent a limited range of rotation.

In any of the example orthopedic devices according to the principles herein, the rigid end regions of the base portion can be formed from a plastic or other rigid polymer material, carbon fiber or other carbon-based material, a metal material (such as but not limited to steel, aluminum, or titanium-based material.

In any of the example orthopedic devices according to the principles herein, the orthopedic device can be configured such that the protrusions are continuous with the base portion, or are separate components that are coupled to the base portion (such as but not limited to using a pin structure). In an example, the protrusions can be coupled to the base portion to allow an amount of rotation between the protrusions and the base portion.

In any of the example orthopedic devices according to the principles herein, the protrusions can be formed from a rigid material exhibiting any degree of rigidity ranging from a high rigidity to intermediate rigidity (a semi-rigid material) to a more flexible material. For example, the protrusions can be formed from a plastic or other rigid polymer material, carbon fiber or other carbon-based material, a metal material (such as but not limited to steel, aluminum, or titanium-based material, or can be a combined arrangements of various elements ranging from flexible, semi-rigid, and rigid elements. For example, the protrusions can be formed from spring-like and other elastic materials that can be used for regenerative purposes.

In any of the example orthopedic devices according to the principles herein, the protrusions can include a padded structure that extends along the base portion. For example, as shown in FIG. 4A, example base mechanism 400 can include a base portion 411 having a rigid first end 412, a rigid second end 414, and a central region 416. Base mechanism 200 can also includes protrusions 418 and 420 that are configured as padded structures. Protrusion 418 has a longitudinal structure having a length that extends to pivot point 422 and couples to cable 426. Protrusion 420 has a longitudinal structure having a length that extends to pivot point 424 and couples to cable 426. In some embodiments, protrusion 418 is coupled to first end 412 and protrusion 420 is coupled to second end 414. The example base mechanism 400 can be coupled to at least one powered element and a control system that receives input from at least one sensor indicating an occurrence of at least one event in a movement of a wearer of the example orthopedic device and generates a responsive control signal. The at least one powered element receives the responsive control signal from the control system and, in response, controls a tensile force through the cable 426 between the pivot points 422 and 424 to produce beneficial forces in the base mechanism, which may be translated to the wearer whether the wearer is moving or still.

In an example, the at least one powered element is configured to control the tensile force extension of the cable 426 between the pivot points 422 and 424. The at least one powered element can be configured to control the extension of the cable 426 upon an indication of at least one signal, responsive to one or more predefined events occurring during movement of the wearer of the orthopedic device. The control of the extension of the cable 426 causes a control of the tensile forces through the cable 226 to generate beneficial forces at the base portion 411, which may be translated to the wearer whether the wearer is moving or still.

In various examples, the control of the extension of the cable 426 between the pivot points 422 and 424 can limit a maximum separation between pivot points 422 and 424 and/or apply a desired magnitude of tensile force in the cable 426.

In a non-limiting example where the orthopedic device is positioned at the leg of a wearer, the at least one powered element can be configured to apply a desired magnitude of tensile force between protrusions 418 and 420, or to limit a maximum separation between pivot points 422 and 424, upon an indication of at least one signal that the wearer is at certain points in the gait cycle. The at least one powered element can be configured to reduce or eliminate the tensile force acting on the cable 426 or to eliminate a restriction on a maximal separation between pivot points 422 and 424, to allow for increased separation between the pivot points 222 and 224 at certain other points during the gait cycle.

FIG. 4B shows the example orthopedic structure of FIG. 4A positioned on a limb such that the protrusions 418 and 420 extend along the base portion, substantially parallel to the limb. In this non-limiting example, the limb is a leg. However, in other examples, the example orthopedic device can be applied to other limbs (including arms) or other body segments that include a joint (including the shoulder/arm joint, or the joint coupling the pelvic region and the thigh/femur). In a non-limiting example, the protrusions 418 and 420 can also extend over a portion of the surface of the limb. The example protrusions 418 and 420 can be formed using soft, semi-rigid, or rigid padding elements to. The longer length of protrusions 418 and 420 along the base portion provide for an increase in the moment arm when generating joint torques from tensile cable forces. In addition, padded structures can provide for increased comfort and protect superficial nerves in some parts of the limb of the wearer.

In a non-limiting example, the protrusions 418 and 420 can also extend over a portion of the surface of a body part. As shown in the example of FIG. 4C, the padded structures of protrusions 418 and 420 can extend over an anterior portion of the surface of the leg.

Figure 5B:
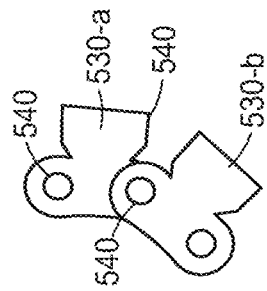
Figure 5C:
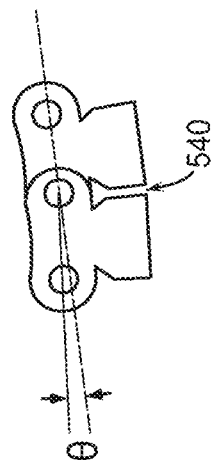
Figure 5A:
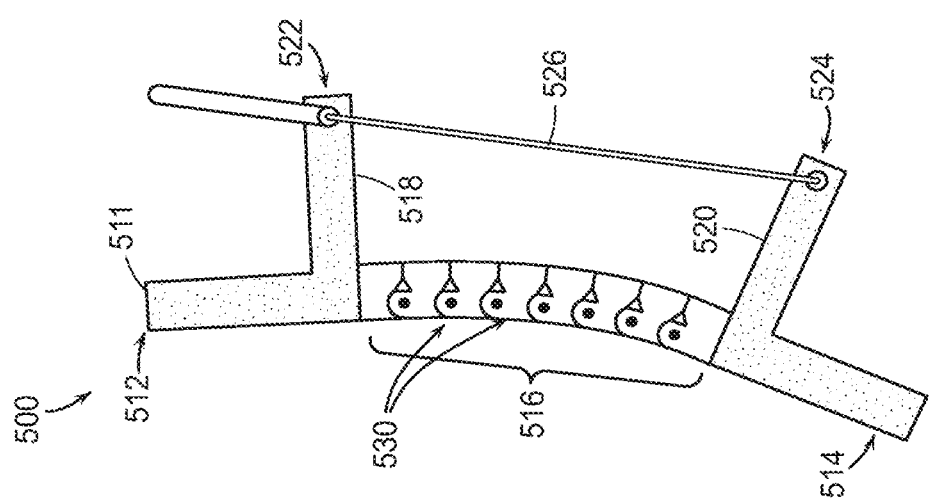

FIGS. 5A to 5C show sections of a non-limiting example orthopedic device in which the central region includes incompressible linking components. In an example, the incompressible linking components are configured to bend preferentially in a given direction of rotation, and to prevent bending beyond a certain extent in the other direction.

FIG. 5A shows a portion of the central region 516 of an example orthopedic device in which the central region comprises a series of linking components 530. The example base mechanism 500 includes a base portion 511 having a rigid first end 512, a rigid second end 514, and a central region 516 and protrusions 518 and 520. The rigid first end 512 includes a protrusion 518 that extends to pivot point 522. The rigid second end 514 includes a protrusion 520 that extends to pivot point 524. Protrusion 518 and 520 are coupled to cable 526 at pivot points 522 and 524, respectively. The example base mechanism 500 can be coupled to at least one powered element and a control system that receives input from at least one sensor indicating an occurrence of at least one event in a movement of a wearer of the example orthopedic device and generates a responsive control signal. The at least one powered element receives the responsive control signal from the control system and, in response, controls a tensile force through the cable 526 between the pivot points 522 and 524 to produce beneficial forces in the base mechanism, which may be translated to the wearer whether the wearer is moving or still.

In an example, the at least one powered element is configured to control the extension of the cable 526 between the pivot points 522 and 524 based on signals received at a control system, according to the principles described herein.

In an example, the central region 516 includes a series of at least three linking components that each enable rotation of the rigid first end 512 with respect to the rigid second end 514 within at least one quadrant and that each prevent rotation of the rigid first end 512 with respect to the rigid second end 514 within at least two other quadrants. In some embodiments, the central region 516, as a whole, also enables rotation of the rigid first end 512 with respect to the rigid second end 514 within at least one quadrant and prevents rotation of the rigid first end 512 with respect to the rigid second end 514 within at least two other quadrants.

FIGS. 5B and 5C illustrate two components 530-a and 530-b that form an exemplary link in a flexible portion. The example components 530-a and 530-b are designed so that they enable rotation in one or two quadrants of rotation, rather than all quadrants. The examplary components are linked at pin joints, and are shaped to mechanically present a hard stop at edge 540 that can limit the extent of rotation in a given direction. As shown in FIG. 5C, the two components 530-a and 530-b are shaped to cause a hard stop that limits the extent of the relative rotation of the liking components to an angle $\theta$ greater than 0° and less than 180°. The hard stop created by the shape of two components prevents them from rotating to linearly align with each other, thereby ensuring that a torque can be applied to the rigid end portions at any allowable range of relative orientation. Thus, the linking components of FIG. 5A are configured as a flexible structure that is restricted to bend preferentially in one or two quadrants in a plane perpendicular to the axis of rotation of the joint.

The linking components 530 allow the limb to bend about the joint, and support compressive loads without buckling when moments are applied to the rigid end components. The plurality of links in central region 516 of base mechanism 500 may enable alignment of central region 516 with the center of rotation of the joint automatically. The plurality of links in central region 516 of base mechanism 500 may enable alignment of central region 516 with the center of rotation of the joint with little effort. The axis of rotation can vary somewhat throughout the range of motion of the limb (such as but not limited to the knee's center of rotation during a walking cycle). Therefore, the example orthopedic device is configured to allow the center of rotation of the joint to move automatically throughout the gait.

Figure 6B:
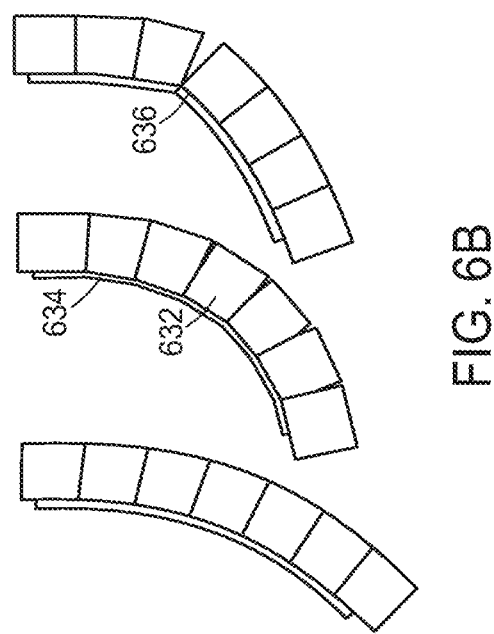
Figure 6A:
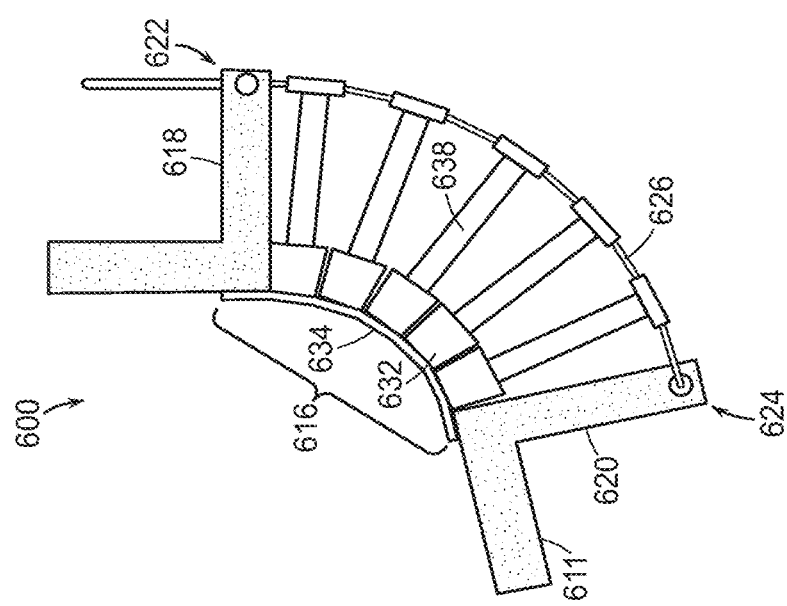

FIGS. 6A to 6B show sections of another non-limiting example orthopedic device in which the central region includes incompressible linking components. The linking components of FIGS. 6A and 6B are also configured as a flexible structure that is permitted to bend preferentially in one or two quadrants of rotation, rather than all quadrants. The example base mechanism 600 includes a base portion 611 having a central region 616 and protrusions 618 and 620. Each protrusion 618 and 620 extends from the base portion 611 and couples to cable 626 at pivot points 622 and 624, respectively. The example base mechanism 600 can be coupled to at least one powered element and a control system that receives input from at least one sensor indicating an occurrence of at least one event in a movement of a wearer of the example orthopedic device and generates a responsive control signal. The at least one powered element receives the responsive control signal from the control system and, in response, controls a tensile force through the cable 626 between the pivot points 622 and 624 to produce beneficial forces in the base mechanism during the movement of the wearer.

In an example, the at least one powered element is configured to control the extension of the cable 626 between the pivot points 622 and 624 based on signals received at a control system, according to the principles described herein.

In an example, the central region 516 includes a series of at least three linking components that each enable rotation of the rigid first end with respect to the rigid second end within at least one quadrant and that each prevent rotation of the rigid first end with respect to the rigid second end within at least two other quadrants.

As shown in FIGS. 6A and 6B, the central region 616 includes a series of links comprising blocks 632 and a flexible layer 634. Flexible layer 634 couples the blocks 632 together, and allows the central region to bend at the junction 636 between two of the blocks 632 in the one or two allowed quadrants about the axis of rotation. As shown in FIG. 6B, the blocks are shaped to prevent rotation in two quadrants. If the movement of the limb is tending to cause the orthopedic device to rotate in those quadrants, the block faces contact each other and prevent that rotation.

In an example, the flexible portion can be formed with a degree of curvature, as shown in FIGS. 6A and 6B. This can allow the orthopedic device to bend more easily than if the flexible region is formed with less curvature or substantially straight. In the example of FIG. 6A, the central region 616 of the orthopedic device includes additional structures, referred to herein as rigid standoffs 638. The rigid standoffs 638 are coupled to the cable 626, to hold the cable at a radial distance (whether large or small) away from the blocks, thereby maintaining a more constant moment arm as the structure bends. In a non-limiting example, the rigid standoffs may include small segments of low-friction sheathing on the ends, to provide a low-friction passageway for the cable. If the cable goes straight in an example base mechanism that does not include these rigid standoffs 638, the distance between the cable 626 and flexible layer 634 can decrease at large angles of bending of the limb (such as, but not limited to, large bending knee angles). The ridged standoffs 638 can be used to create a constant-moment system in conjunction with a spring that increases in force, but may also be less useful if the radius goes close to zero at large end angles.

FIGS. 7A through 7D show another example base mechanisms of orthopedic devices that are similar to the embodiments of FIG. 2A or 2B. The example base mechanisms include a base portion 711 having a rigid first end 712, a rigid second end 714, and a central region 716. The central region 716 of the base portion 711 is configured to facilitate rotation of the rigid first end 712 relative to the rigid second end 714 within the central region 716. The example base mechanism 710 includes protrusions 718 and 720. Protrusion 718 extends from the first end 712 to pivot point 722. Protrusion 720 extends from the second end 714 to pivot point 724. The example base mechanism 710 also includes a cable 726 that couples pivot point 722 of protrusion 718 to pivot point 724 of protrusion 720.

Figure 7A:
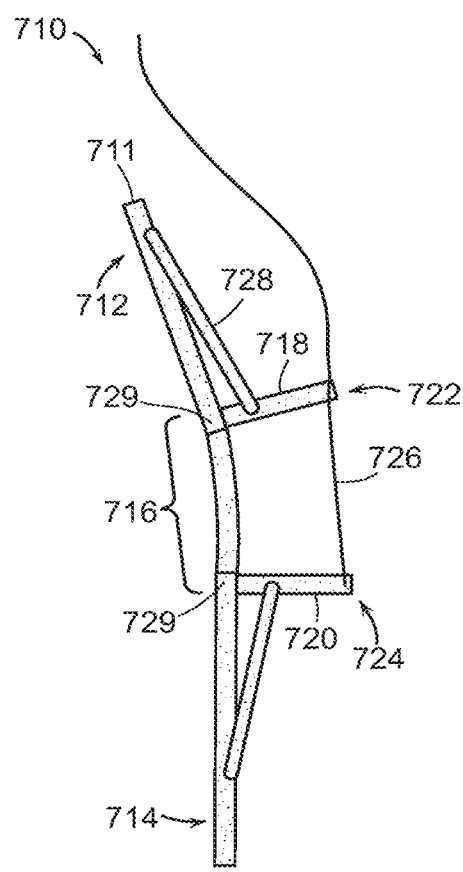
Figure 7B:
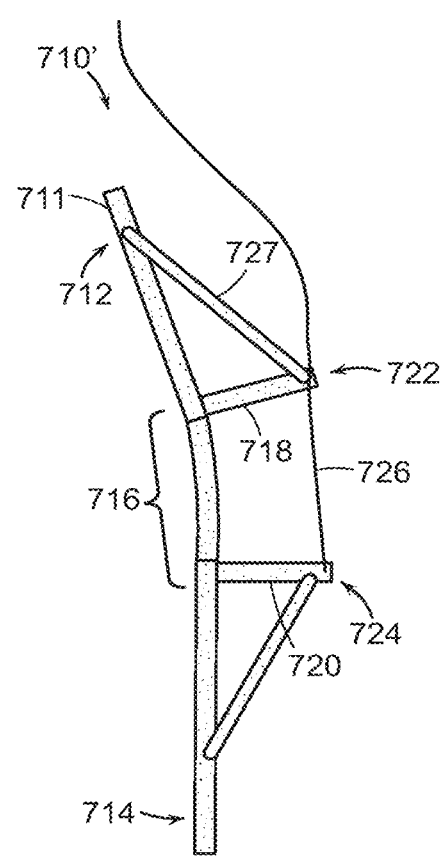
Figure 7C:
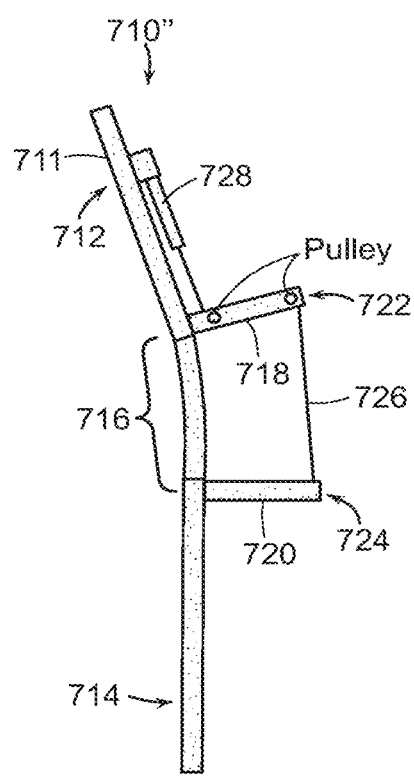
Figure 7D:
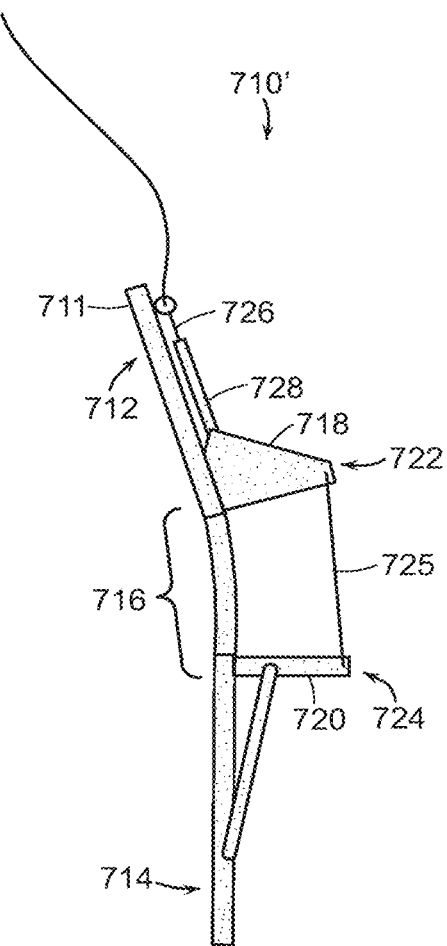

Example base mechanism 710 also includes at least one resilient component that operates in cooperation with the cable 726 and the protrusions 718 and 720 to apply torques to body segments about the axis of rotation of a joint of the body segments. The example base mechanism 710 can be configured such that the at least one resilient component couples the base portion to at least one of the protrusions. The example of FIG. 7B shows a base mechanism 710 that includes a resilient component 727 coupling a first end 712 of base portion 711 to pivot point 722 of protrusion 718. FIGS. 7A, 7C, and 7D show example base mechanisms 710, 710" and 710" that includes a resilient component 728 coupling the first end 712 of base portion 711 to a different portion of protrusion 718 (i.e., a point along the mid-section of protrusion 718). Both FIGS. 7A and 7B show example base mechanisms that includes two resilient components, each coupling the protrusions 718 and 720 to a different rigid end of the base portion 711. The example of FIG. 7B shows both resilient components couple to the pivot points of the protrusions, while FIG. 7A shows an example where both resilient components coupled to a different portion of a protrusion (such as but not limited to a point along the mid-section of the protrusion).

FIGS. 7A through 7D show various embodiments of orthopedic devices that include at least one resilient component 727 or 728 coupled to the protrusions.

In the example of FIG. 7A, the protrusions are formed as rigid beams that are configured to pivot about pivots 729 about their base at the base portion 711. This enables the protrusions to rotate so the distance between their ends is fixed if the powered element (such as but not limited to the controllable clutch) is locked.

In the example FIG. 7B, the beams protruding from the base beams act as elastic members (such as but not limited to a leaf springs) and can bend so that the orthopedic device structure as a whole can bend. The elastic elements 728 can be connected or otherwise coupled to the elastic member to provide an additional resistive force.

In the example FIG. 7C, the cable between the protrusion 718 and 720 extends over pulleys to change the direction of the cable. The cable can be attached to an elastic element (or a motor) so that a restoring force is applied.

In embodiments according to the principles herein, the rigid elements parallel to the limb could be connected by a simple pin joint or by a more complicated mechanism that can bend at multiple locations but will not buckle.

In the example of FIG. 7D, a fixed length cable is coupled to protrusions having a triangular conformation. This example uses a rigid frame similar to that used in the examples of FIGS. 7A through 7C, except that the distance between the pivot points of the triangles is fixed by a cable, a string, or other equivalent structure. The Bowden inner cable is coupled, near the rigid first end 712 of the base portion, to the elastomer spring. In an example implementation, the elastomer spring is mounted on the rigid first end of the base portion 711, and is in series with the motor (not shown). In this example, the motor can cause a tensile force to act on the cable 726 between the protrusions 718 and 720, essentially as a clutch, if the wearer is descending (e.g., going downhill), and then release the tensile force on the cable or use the retraction to provide regenerative power when releasing stored spring energy. In an example where the user is ascending an incline (e.g., going uphill), the motor can be caused to apply less force to allow an amount of slack in the cables until the control system receives an indication that the foot has made contact with a surface. At this point, the control system can be caused to issue a command to cause the spring to be wound, i.e., to store an amount of potential energy, so that when the user extends the limb, there is an amount of potential energy stored in the orthopedic device to assist the wearer.

In any of the example orthopedic devices described in connection with FIGS. 7A through 7D, the example base mechanism 710, 710' or 710" can be coupled to at least one powered element and a control system that receives input from at least one sensor indicating an occurrence of at least one event in a movement of a wearer of the example orthopedic device and generates a responsive control signal. The at least one powered element receives the responsive control signal from the control system and, in response, controls a tensile force through the cable 726 between the pivot points 722 and 724 to produce beneficial forces in the base mechanism during the movement of the wearer.

In an example, the at least one powered element is configured to control the extension of the cable 726 between the pivot points 722 and 724. The at least one powered element can be configured to control the extension of the cable 726 upon an indication of at least one signal, responsive to the one or more predefined events occurring during movement of the wearer of the orthopedic device. The extension of the cable 226 controls the tensile forces through the cable 226 to generate beneficial forces at the base portion 711, which can be translated to the wearer whether the wearer is moving or still.

Figure 8B:
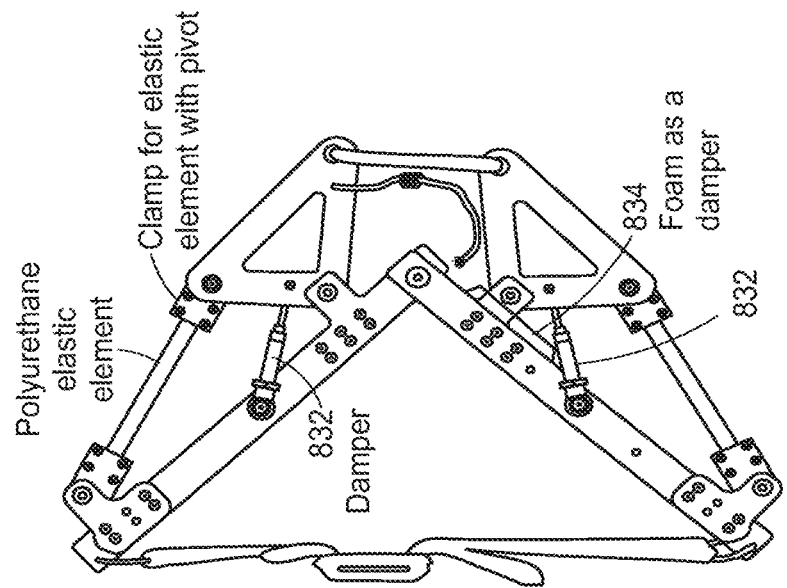
Figure 8A:
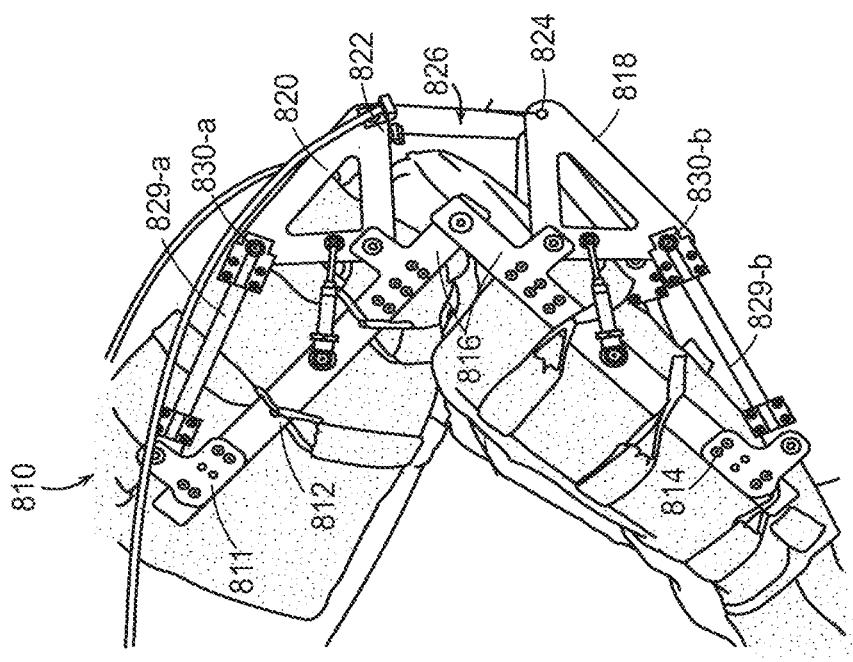

FIGS. 8A and 8B show an example orthopedic device 810 that is similar to the embodiment shown in FIG. 2C. Example orthopedic device 810 includes a base portion 811 having a rigid first end 812, a rigid second end 814, and a central region 816. The central region 816 of the base portion 811 enables rotation of the rigid first end 812 relative to the rigid second end 814. The example base mechanism 810 includes protrusions 818 and 820, each of which extends from the base portion 811 to pivot points 822 and 824, respectively. The example base mechanism 810 also includes a cable 826 that couples pivot point 822 of protrusion 818 to pivot point 824 of protrusion 820.

Example base mechanism 810 also includes at least one resilient component that operates in cooperation with the cable 826 and the protrusions 818 and 820 to apply torques to body segments about the axis of rotation of a joint of the body segments. The example base mechanism 810 can be configured such that the at least one resilient component couples the base portion to at least one of the protrusions. As shown in FIGS. 8A and 8B, the example base mechanism 810 includes two resilient components 829-a and 829-b. Resilient component 829-a couples the first end 812 of base portion 811 to a point along an edge of protrusion 818, while resilient component 829-b couples the second end 814 of base portion 811 to a point along an edge of protrusion 220. While the example of FIG. 2C shows both resilient components 829-a and 829-b coupled to the pivot point of a protrusion, at least one of resilient components 829-a and 829-b could be coupled to a different portion of a protrusion (such as but not limited to a point along a different edge of the protrusion).

In a non-limiting example, the protrusions 818 and 820 coupled to the base portion 811 such that an amount of rotation can occur between the protrusions 818 and 820 relative to the base portion 811.

In a non-limiting example, at least one damper spring 832, damper component 834, or other resilient component can be used to couple portions of the protrusions 818 and 820 to the central region of the orthopedic device 810. Damper component 834 can be positioned along the top of the rigid base ends, near the base of the protrusions 818 and 820. As a non-limiting example, damper component 834 can be a foam. Either damper springs 832 or damper component 834, or both damper springs 832 and damper component 834, can be used to cushion the protrusions 818 and 820 as they rotate back into their original position. Hysteresis in the elastic elements or friction elements (such as but not limited to damper springs and/or damper components) at the pivot point 818 and 820 of the protrusions 818 and 820 can be beneficial. Friction elements at various locations in the example orthopedic device also could be used provide an increased force resisting the motion of the limb, which can be beneficial.

In an example, implementation the base portions can be formed as rigid beams for positioning in parallel with the thigh and shank (lower leg below the knee). These rigid beams are connected together using springs and a Bowden cable that extends up to a clutch/actuation box mounted on the wearer's torso. The rigid portions of the exoskeleton are connected to the wearer through a fabric interface. Sensors of the wearer's gait or knee angle (such as but not limited to at least one footswitch, gyroscope, and/or angle sensor) can be used to indicate to the device when the clutch or actuation should be applied. According to any of the control systems according to the principles described herein. In an example orthopedic device of FIGS. 8A and 8B, the Bowden cable sheath can be connected to pivot point 822, and the inner cable extends further to pivot side 824.

Figure 8C:
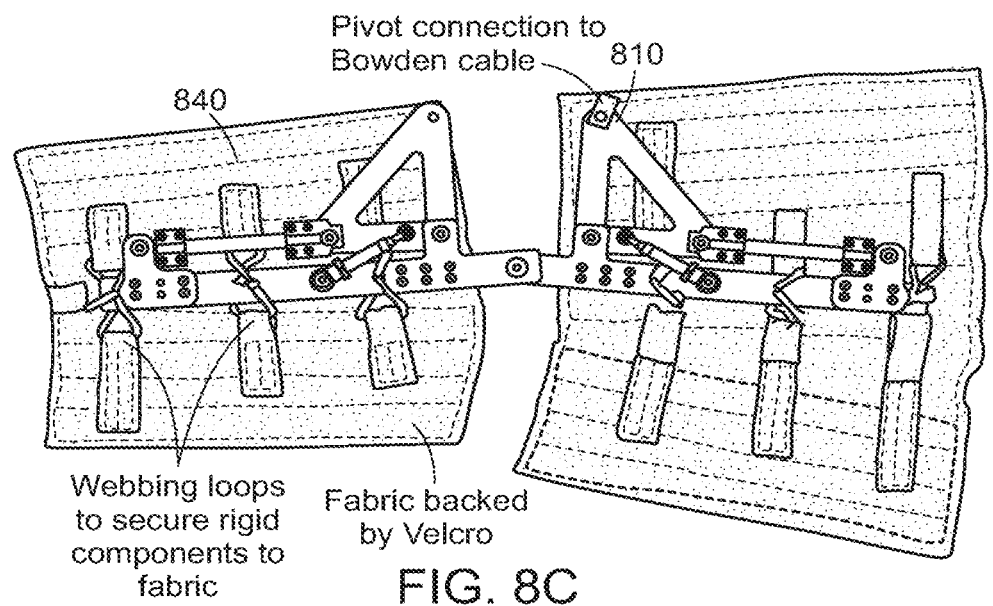

FIG. 8C shows an example interface 840 that can be used to couple the base mechanisms of the orthopedic device to the limb, to couple the beneficial forces from the orthopedic device to the limb. In any example herein, the interface can be made of a fabric, VELCRO® fasteners (VELCRO INDUSTRIES B.V., the Netherlands), or other similar material.

Figure 8D:
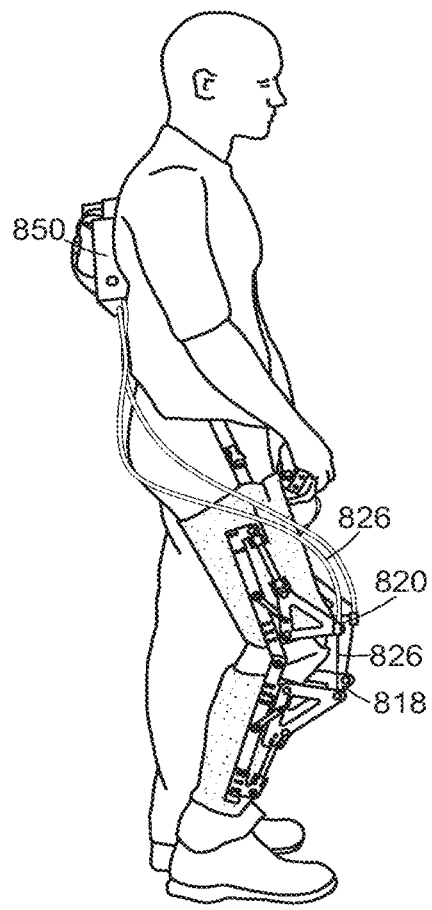
Figure 8E:
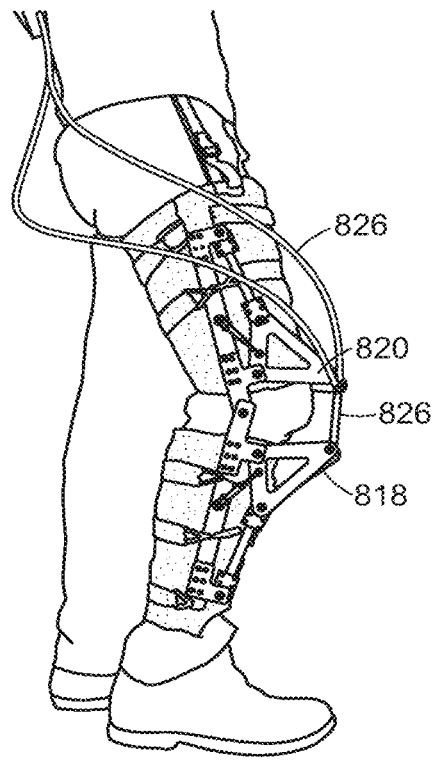

FIGS. 8D and 8E shows the example orthopedic device of FIGS. 8A and 8B positioned on a leg of a wearer. As shown in FIG. 8D, the cable 826 from the orthopedic device 810 can couple the protrusions 818 and 820 to a powered element, such as but not limited to an actuator or a clutch. The powered element can be housed in a backpack, a bag, coupled to the waist, or strapped to another body part. The base mechanism can be coupled to the powered element via the cable 826. The control system can be housed in the backpack, the bag, coupled to the waist, or strapped to another body part. FIGS. 8D and 8E show an example of the orthopedic device where the cables terminate at a clutch box located in a pack on the wearer's back.

FIG. 8B shows the position and conformation of the components of the example orthopedic device if the clutch is engaged and the corners of the triangular elements are held at a fixed maximum allowable distance apart (in this example, using a rope to hold them together). Since the orthopedic device is bent at an angle due to the position of the limb, the elastic elements 829-a, 829-b are stretched and a restoring force is generated about the joint. FIG. 8B shows the conformation and position of components of the example orthopedic device if no force is acting on the elastic elements.

In this embodiment, there is a linkage including two triangular elements which pivot about their connections to the element parallel to the leg. On one corner of these, the Bowden cable sheath or inner cable are connected; on the other corner, an elastic element is connected. The elastic element extends from the corner of the triangular piece to the rigid element parallel to the leg.

An example operation of the orthopedic device of FIGS. 8A through 8D can be as follows. When the orthopedic device is coupled to body parts including a joint and the wearer bends the body part about the joint, the distance between the pivot points of the rigid protrusions increases. This exerts a force to pull the inner cable of the Bowden cable out of the Bowden cable sheath. This movement can then be resisted using a powered element, such as but not limited to a clutch or damper in the unit attached to the waist belt. This causes the orthopedic device to absorb power from the knee, for example, if an individual is walking downhill. An example orthopedic device herein can be used to help to prevent or buffer against the high torques that the knee can experience during downhill walking, which can lead to injury. The orthopedic device also could be configured to hold the cable in place using a powered element (such as a clutch). In this embodiment, the orthopedic device acts as a rigid brace and prevents the wearer's knee from bending. The compliance of the wearer's muscle and the fabric permit a small amount of additional bending.

In an embodiment, a resilient component (such as but not limited to a spring, leaf spring, or other elastic component) may be disposed in series with the cable. Energy can be stored in the resilient component in series with the cable, and returned to the wearer if the orthopedic device is locked with a clutch.

In another embodiment, a motor or an actuator can be implemented to exert a force on the cable (i.e., actively pull on the cable). In this embodiment, the orthopedic device acts to extend the wearer's limb, for example to help a wearer walking uphill or standing up from a squatting position when the orthopedic device is coupled to one or both legs.

In another embodiment, a resilient component (such as but not limited to a spring or other elastic element) could also be disposed in series between the motor and the region of coupling of the two rigid protrusions.

In any example orthopedic device according to the principles herein, another force transmission element may be used in place of the cable. The force transmission element can be any component capable of transmitting a force. Although generally described as a cable, such as but not limited to a Bowden cable, a force transmission element may alternatively include a fluidic muscle actuator, a webbing strap, an electroactive material actuator (e.g. polymer or shape memory alloy), an active or passive clutch, and non-Newtonian fluids within microchannels. With respect to a Bowden cable, such a force transmission element includes a metal cable surrounded by a sheath.

Further, a force transmission element may be any element capable of generating a force. Examples of force transmission elements that generate a force include springs, dampers, and other materials and/or shapes that behave as spring-damper systems in addition to active or passive clutches that can selectively engage and disengage such elements.

Figure 9A:
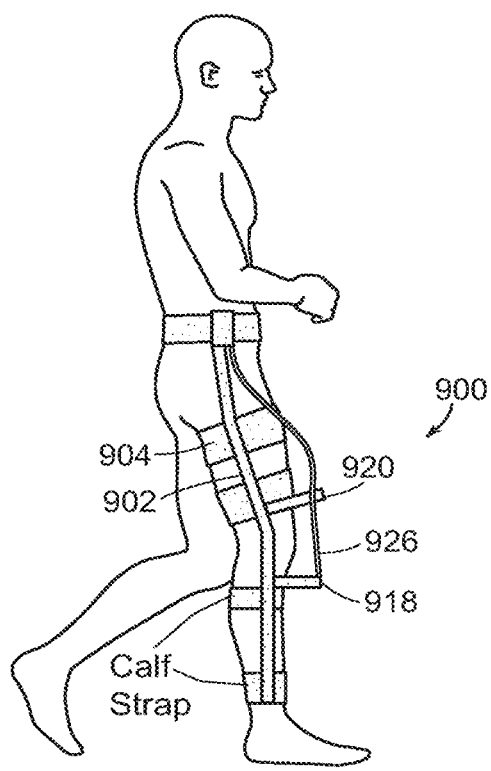
Figure 9B:
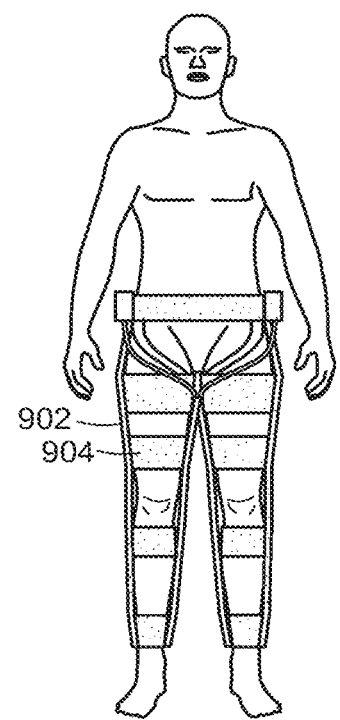

FIGS. 9A and 9B show a non-limiting example of an orthopedic device 900 disposed at both legs of a wearer. The example orthopedic device includes two rigid bars 902 for positioning along the legs with protrusions 918 and 920 that are directed anterior to the joint, such that the protrusions 918 and 920 can apply a force anterior to the axis of rotation to the knee joint. In the example of FIGS. 9A and 9B, the rigid bars 902 are coupled to the limbs using straps 904. In another example, the straps 904 can be configured as a continuous piece of fabric along the entire length that the rigid bars are sewn into, or otherwise coupled with, along their length. At the central region of the orthopedic device, there are protrusions 918, 920 from the top and bottom rigid bars so that the ends of the protrusions are several centimeters forward from the center of rotation of the joint. A Bowden cable sheath is connected to the end of the top protrusion 920, and the inner cable extends down to the end of the bottom protrusion 918. The Bowden cable sheath is attached with a pivot so it can rotate and self-align with the direction of the cable. This Bowden cable extends upwards to the wearer's waist, where it terminates in a unit that includes a clutch or a damper or an actuator or some combination of thereof. A waist belt is connected to several straps extending down to the knee brace to hold it up and keep it from falling down the leg.

The example of FIG. 9A shows an orthopedic device including a brace mechanism that is coupled to a side of a limb. In another example, the orthopedic device can include two brace mechanisms, each positioned on opposite sides of the limb.

FIG. 9B shows a non-limiting example implementation in which an orthopedic device is positioned on each limb.

In an embodiment, the orthopedic device includes a cross-bar across an anterior portion of the limb, to link the two base mechanisms on either side of the limb. In this example, the cross-bar keeps the two base mechanisms in some fixed orientation and position laterally with respect to each other.

In an embodiment, the orthopedic device does not include Bowden cables but does include a clutch, or a damper, or an actuator unit attached to the protrusion on top of the rigid element.

An example operation of the orthopedic device of FIGS. 9A and 9B is as follows. Under flexion, when the movement of the limb causes the structure to bend with the relative rotation of the upper limb and lower limb, the separation between the pivot points of the protrusions increases. This pulls the inner cable out of the Bowden cable sheath. This motion can then be resisted by a clutch or damper in the unit attached to the waist belt. This will absorb the power from the knee, for example, if an individual is walking downhill, standing from a squatting position, lifting a load, or other movement. The device could also hold the cable in place using a clutch, so the device acts as a rigid brace that prevents the wearer's joint from bending. The compliance of the muscles and fabric will them permit a small amount of additional bending. Some energy could also be stored in a spring in series with the cable and returned to the wearer if the device is locked with a clutch.

In another example, the orthopedic device is configured to actively exert a force on the cable using a motor or other actuator. In this case, the orthopedic device acts to extend the limb of the wearer, for example, to assist with walking uphill or standing up from a squatting position.

Any example orthopedic device according to the principles herein can include a control system that receives input from at least one sensor indicating an occurrence of at least one event in a movement of a wearer of the orthopedic device and generates a responsive control signal. The at least one powered element receives the responsive control signal from the control system and, in response, controls a tensile force through the cable between the first pivot point and the second pivot point of each base mechanism to produce beneficial forces in the base mechanism that are translated to the wearer.

Example control systems are provided for controlling a tensile force through the cable between the first pivot point and the second pivot point of each base mechanism to produce beneficial forces in the base mechanism during a downhill (descent) movement of the wearer. In this example, the limb is a leg, and the control system is configured to, in response to first input indicating a maximum extension of the knee in a descent movement, generates a responsive control signal that causes the at least one powered element to increase the tensile force through the cable to limit a maximum separation between the first pivot point and the second pivot point of each base mechanism of the pair of base mechanisms. The control system, in response to second input indicating a foot strike in a descent movement, generates a responsive control signal that causes the at least one powered element to reduce the tensile force through the cable to allow an increased separation between the first pivot point and the second pivot point of each base mechanism of the pair of base mechanisms.

Example control systems are provided for controlling a tensile force through the cable between the first pivot point and the second pivot point of each base mechanism to produce beneficial forces in the base mechanism during an uphill (ascending) movement of the wearer. During uphill walking, in each gait cycle an extension moment at the knee can occur shortly after foot strike of the corresponding foot, and continue for roughly a quarter of the gait cycle (which is defined to extend from one foot strike until the next foot strike of the same foot). This knee moment propels the body upward during uphill walking. In an example, it can be preferable to create tension in a cable at the same times as this biological moment in order to assist the knee effectively. The beginning of this knee extension moment period can be an indicator of a first event in the gait cycle. One possibility for this first event is an inflection point in the knee angle that occurs at roughly 5-8% in the gait cycle. A second event in the gait cycle can correspond to the end of this knee extension moment period. Another example event can be the next inflection point in the knee angle that occurs roughly at 30-33% in the gait cycle. The beginning time could be approximated by one or more of several other signals that could serve as a first event. These include determining the foot strike time itself and adding a delay, or detecting another gait event that is closely related in time to the beginning of this knee extension moment period. For example, a gyroscope mounted on a wearer's heel can show a distinct peak at around 4% in the gait cycle as the wearer's foot rotates downward after heel strike. In an example, using this gait event (based on the gyroscope signal) in conjunction with a short time delay could be used as an indicator of an event coinciding with the beginning of the knee extension moment. Other potential gait events occurring at almost this time include the heel strike itself, or the foot on the opposite leg lifting off the ground. Each of these gait events could be used effectively as a first event for the control system. Similarly, one or more of several other gait events corresponding to times close to the end of the extension moment period could be used as a second event for the control system. In an example, this second event could be indications of the center of mass reaching a peak displacement as measured in the vertical direction, or the hip angle of the same leg passing through zero degrees (e.g., the thigh being in line with the torso). In this example, the control system, in response to a first input, generates a responsive control signal that causes the at least one powered element to increase the tensile force through the cable to decrease a maximum separation between the first pivot point and the second pivot point of each base mechanism of the pair of base mechanisms. The control system, in response to a second input, generates a responsive control signal that causes the at least one powered element to reduce the tensile force through the cable to allow an increased separation between the first pivot point and the second pivot point of each base mechanism of the pair of base mechanisms.

Example control systems are provided for controlling a tensile force through the cable between the first pivot point and the second pivot point of each base mechanism to produce beneficial forces in the base mechanism during movement of the limb is a leg. In this example, the control system, in response to first input indicating an increasing extension of the knee in an approximately level movement, generates a responsive control signal that causes the at least one powered element to increase the tensile force through the cable to decrease a maximum separation between the first pivot point and the second pivot point of each base mechanism of the pair of base mechanisms. The control system, in response to second input indicating an increasing flexion of the knee in an approximately level movement, generates a responsive control signal that causes the at least one powered element to reduce the tensile force through the cable to allow an increased separation between the first pivot point and the second pivot point of each base mechanism of the pair of base mechanisms.

An example system, method, and apparatus herein provides an improved knee brace/exoskeletons, that provides resistive torques as a function of knee angle when the knee is in any bent configuration, even if it is stationary or straightens out after bending initially. It does this by storing energy in springs or elastic elements which become loaded as the knee bends, and then either returning most of that energy to the wearer as the leg straightens, or by releasing the energy into dampers or an electric generator.

An example system, method, and apparatus herein can also provide assistive torques to the knee to support lifting heavy objects or strength enhancement for applications such as rigid exoskeletons or impaired individuals. In these implementations, the orthopedic device could be used with actuators to straighten the leg actively, or again use spring or elastic elements to store energy as the leg is bent and released. The example orthopedic device is lighter and simpler than existing technologies, and is extremely low-power. For example, a configuration that uses a clutch to hold the energy in the springs provides a low-power solution.

An example system, method, and apparatus herein can be used to provide a resistive force about the knee that is always present if the knee is bent. This example control scheme can be used for activities involving movement such as but not limited to skateboarding, skiing, snowboarding, or water-skiing, where the user remains in a crouched position for much of the time.

An example orthopedic device according to the principles herein provides a exoskeletons that can align with the biological joints more perfectly. Many existing rigid exoskeletons (including rehabilitation exoskeletons) can alter natural movement patterns, which is undesirable.

For any example orthopedic device according to the principles herein, the control system can include at least one memory and at least one processing unit configured to execute processor-executable instructions stored in the memory. Based on the processor-executable instructions, the orthopedic device can be caused to compute a joint angle of the joint in response to input and generate a responsive control signal based, at least in part, on the computed joint angle. In an example, the control system can include at least one microcontroller and/or other integrated circuit component. In an example, the control system can include at least one coil, such as but not limited to a near-field communication (NFC) enabled coil, to receive and/or transmit data.

As a non-limiting example, the systems, methods and apparatus described herein can provide for communication of data and or the results of analysis of data to computing devices, including smartphones (such as but not limited to an Iphone®, an Android™ phone, or a Blackberry®), tablets, slates, electronic books, laptops, electronic gaming systems (such as but not limited to an XBOX®, a Playstation®, or a Wii®), electronic readers, or other computing devices, to facilitate external monitoring capabilities.

In any example herein, the control system can be configured to receive a signal, including data, from a sensor component such as but not limited to a triaxial accelerometer, a gyroscope, hydration sensor, temperature sensor, and an electromyography (EMG) component. An example control system herein can include one or more of a battery (including a rechargeable battery, a transmitter, a transceiver, an amplifier, a processing unit, a charger regulator for a battery, a radio-frequency component, a memory, and an analog sensing block, a flash memory, a communication component (such as but not limited to Bluetooth® Low-Energy radio) and/or other sensor component.

An example sensor can be configured to provide to the control system data indicative of sensor data such as but not limited to at least one of the joint angle, a muscle activation condition, a pressure on a foot during a gait cycle, an instance in time that a foot strikes a surface during a gait cycle, or the tensile force in each cable. The sensor can be configured to provide input indicative of gait for a wearer of the orthopedic device, where the joint angle is computed based on the data indicative of gait. The input indicative of gait can include data indicative of a gradient of descent of the wearer.

In any example, the sensor unit may be coupled to a portion of the orthopedic device and/or a portion of the limb, to provide the data indicative of a degree of extension or flexion of the limb. The sensor can be configured to provide data indicative of the angle between the proximal portion of the limb and the distal portion of the limb, thereby providing the data indicative of the degree of extension or flexion of the limb.

The control system can be configured to generate a control signal that causes the powered element to control the tensile force through the cable between the first pivot point and the second pivot point. As a result, a resistive torque is applied to the limb on detection of a signal indicating a flexion of the limb or a signal indicating a degree of flexion of the limb maintained for a period of time greater than a predetermined threshold. The data can be derived from a sensor configured to provide data indicative of at least one of the joint angle, a muscle activation condition, a pressure on a foot during a gait cycle, an instance in time that a foot strikes a surface during a gait cycle, or the tensile force in each cable.

In a non-limiting example orthopedic device, the powered element can be an actuator or a controllable clutch. For example, the control system can issue commands to cause a controllable clutch to control an extension of the cable. FIGS. 10A and 10B show a non-limiting example electromagnetic clutch 1000 that can be implemented as a controllable clutch according to the principles herein. Clutch 1000 includes bearings 1002 and 1003, discs 1004, and shaft collars 1006. The cable of any of the orthopedic devices herein can be coupled to the clutch 1000 at locations 1008. As described herein, the clutch 1000 can be locked or unlocked. The example clutch can be operated to connect and disconnect at least one of the rotating shafts to the driving member to provide output power for work. While typically the motions involved are rotary. The clutch 1000 can be engaged by an electromagnet of the clutch assembly.

While an electromagnetic clutch is described, other example clutch assemblies also can be implemented in an example orthopedic device according to the principles herein.

The example control system can be configured such that the controllable clutch retracts in the cable at the portions of the movement of the wearer where the maximum allowable separation is to be maintained between the pivot points. The controllable clutch can be configured to control the extension of the cable based on commands from the control system. On receiving a first signal, the control system can cause the clutch to lock. By causing the clutch to lock to holding the cable at the desired extension, the control system can cause the movement of the wearer of the orthopedic device to generate tensile forces to be applied through the cables. As a result, the desired beneficial forces can be generated at the body segments coupled to the orthopedic device. On receipt of a second signal, the example control system can be configured to command the clutch to unlock, responsive to the one or more predefined events occurring during movement of the wearer. When the clutch is unlocked, the cable is allowed to extend more freely, and as a result allow the wearer to move more freely. The locked state of the controllable clutch limits a maximum allowable extension of the coupled cable, as a result, the maximum separation between the first pivot point and the second pivot point of the same base portion is limited. The unlocked state of the controllable clutch allows the extension of the coupled cable to vary, which allows variable separation between the first pivot point and the second pivot point of the same base portion.

In a non-limiting example orthopedic device, the powered element can be an actuator coupled to a controllable clutch. The actuator could be used to create tension in the cable at the appropriate points in the movement cycle (e.g., during a downhill portion of a walking gait cycle) so as to cause the movement of the wearer to increase the tensile force to once it is detected that the wearer is walking downhill. At other portions of the movement cycle, the clutch unit could be used to reduce the extension of the cable and to hold the cable in place to impose the maximum allowable separation of the pivot points, thereby generating the beneficial forces.

In an example, the clutch may be operable manually, to allow the wearer to manually lock or unlock the cable to adjust the extension of the cable.

FIG. 11 shows an example clutch box 1100, showing a Spectra line 1102 winding about a shaft 1104. The Bowden cable sheath (not shown) is connected to the outside of the housing where the spectra line exits the box. The Spectra line extends to the protrusions of a first base mechanism of the orthopedic device. The clutch box 1100 can also a second spectra line leading to a the protrusions of a first base mechanism of the orthopedic device, and wraps around the shaft just to the right of Spectra line 1102.

A clutch is shown on the right of the lower shaft which either permits the shaft to spin freely or locks it to the housing. On the right side of the figure, a larger-diameter pulley 1106 winds a small cable connected to a spring-retract key fob. This creates a torque on the shaft, which winds up the Spectra line 1102 after it has been extended. This force is small enough that it does not affect the motion of the limb. The example clutch box 1100 also includes a microcontroller that can be configured to execute processor-readable instructions to cause the powered element to effect the control schemes described herein. For example, the microcontroller can be configured to perform the data analysis described herein based on data received from sensor components and/or to send at least one signal to the clutch to engage or disengage based on the analysis of the sensor data. In the non-limiting example it FIG. 11, the microcontroller is an Arduino microcontroller that does processing of sensors, and sends signals to the clutch to engage or disengage.

In a non-limiting example operation of the orthopedic device, the microcontroller can be used to send a signal to cause the clutch to engage when the wearer's opposite foot lifts off from the ground. At this point, the wearer is placing all of their weight on one leg, and they begin to bend that leg if they are walking downhill. The clutch engaged prevents the inner cable (Spectra line) from exiting the sheath further, which means that the maximum allowable distance between the corners of the two triangular elements is approximately constant (minus the stretch of the Spectra line). This means that as the knee bends, the triangular elements must rotate about where they connect to the rigid beams parallel to the leg. This in turn stretches the elastic elements connected to the other protrusions (such as the corner of the triangular protrusion elements of FIGS. 8A and 8B). This provides a spring force which resists the motion of the knee. If the knee then straightens again, the spring force will assist the knee to straighten. However, if the user is walking and wishes to swing their knee, the microcontroller can be used to send a signal to the clutch to cause it to disengage, based on an analysis of data from the sensors. In this example implementation, the clutch can be set to disengage when the opposite foot touches down on the ground again. Once the clutch disengages, the elastic elements retract, causing the triangular pieces to rotate and the inner cable to be pulled out of the Bowden cable sheath. This frees the limb to move uninhibited for the movement (e.g., a next step).

In an example implementation, dampers can be used to resist the motion of the triangular elements rotating. When the knee is being loaded, dampers in parallel with the elastic elements provide additional resistive forces against the knee's bending. When the clutch is released, the dampers prevent the triangular protrusions from rotating back to their original position very quickly, and thereby causing noise and disruption.

In a non-limiting example operation of the orthopedic device, the microcontroller can be used to send a signal to cause the clutch to engage and lock while the leg is straight, and then the exoskeleton provides a resistive torque if the leg is bent. The orthopedic device continues to apply the torque if the wearer holds their position, for example if they are searching for a foot-plant location while walking downhill. The orthopedic device may also apply torques if the wearer lifts their body up again, for example if the wearer reverses their direction of walking. During downhill walking applications, the exoskeleton then disengages the clutch when the knee is bent. This will smoothly release the force on the leg, permitting the knee to bend additionally to prepare for swing without restriction. Optionally, when the force is released, it can be used to power a generator.

In a non-limiting example operation of the orthopedic device for lifting applications, the microcontroller can be used to send a signal to cause the clutch to be locked while the leg is straight, and then the wearer squats to pick up a heavy object. In this scenario, when the wearer stands up straight again, the orthopedic device provides assistive forces as the wearer straightens their leg, at which point the clutch could be released and they could walk normally.

In an example, the control system can issue commands to cause an actuator to control an extension of the cable. An example actuator unit 1200 includes a drive motor 1222 and a pulley module 1224, such as is shown in FIGS. 12A and 12B. The actuator unit 200 is used to drive a Bowden cable 1202 based on commands from the control system. The Bowden cable 1202 is attached to a pulley wheel 1225 in the pulley module 1224 and is extended and retracted by rotation of the pulley wheel 125. In accord with some embodiments, the drive motor 1222 includes gearing (e.g., a gear box as shown in FIGS. 12A and 12B) to increase the drive torque of an output shaft coupled to the pulley module 1224 to drive the Bowden cable 1202 that provides the assist to the user's motion. In other aspects, the motor 1222 is connected directly to the pulley module 1224 without intermediate gearing.

The drive motor 1222 advantageously comprises an encoder (not shown) or other positional sensor configured to indicate the rotational position of the motor output shaft. The drive motor 1222 (and encoder if provided) are connected to a motor controller 1228 used to control the power, speed and direction of the drive motor 1222. In accord with some aspects of the present concepts, a centralized motor controller is provided to control more than one motor. Alternatively, each actuator unit 200 includes its own resident system controller 1226 configured to receive sensor inputs and to communicate with the motor controller 1228 to control the operation of the drive motor 1222 for that actuator unit. The system controller 1226 (or optionally centralized motor controller) can include a computer or microprocessor-based system, such as, but not limited to, those based on the PC/104 standard. The drive motor 1222 is coupled directly or indirectly (e.g., through a gear train) to the pulley module 1224 comprising a pulley wheel 1225 engaging the proximal end of the Bowden cable 1202.

The pulley module 1224 comprises a housing 230 adapted to engage the Bowden cable sheath 144 such that, when the pulley wheel 1225 is rotated in a first direction, the Bowden cable 1202 wraps around the pulley causing the distal end of the Bowden cable 1202 to be retracted into the distal end of Bowden cable sheath 144 and, when the pulley is rotated in a second direction, the Bowden cable is unwound from the pulley, causing the distal end of the Bowden cable 1202 to extend from the Bowden cable sheath 144. In at least some embodiments, the pulley 1225 is enclosed in the housing 230 such that, when it is rotated in the second direction, the cable 1202 is driven out and can apply an extension force.

The control system 1226 is configured to sense or determine the gait of the user and actuate the drive motor 1222 to pull on the Bowden cable during specific times of the gait cycle or to actuate another actuation system configured to introduce forces at specific times of the gait cycle (or other movement).

In accord with various example implementations, the sensor can take many forms, including sensors that sense the angular position of specific joints. See, for example, commonly owned WO 2013/044226 A2, which is hereby incorporated by reference in its entirety. In accord with some aspects, the sensors comprise a pressure sensor or a simple on/off switch that senses the pressure of the foot during the gait cycle, such as but not limited to a heel strike.

In accord with other aspects of the present concepts, one or more sensors can take the form of EMG sensors that sense muscle activation at specific locations. The pattern and scale of these activations can either determine gait cycle (pattern) or amount of assistance required (based on scale). Other sensors that detect joint position, relative or absolute, either with respect to ground or respect to a point on the wearer, may be used to determine gait pattern and, therefore, can be used to control actuator activation. Other sensors can include, but are not limited to, hyper elastic strain sensors, accelerometers, inertial measurement units, internal measurement Units (IMU) and/or Goniometer sensors. These sensors, or other sensors, singly or in combination, can detect motion indicative of body position. Depending on the sensor(s) used, heuristics specific to that system are able to be developed to determine when the muscles in the body are applying force to a joint (e.g., such as the ankle, knee, or hip) so that the orthopedic device can, in turn, be configured to apply force at the appropriate time.

In some aspects, the actuator unit 200 is configured to communicate with a local or remote external computer (e.g., a desktop or laptop computer, tablet or a smartphone) over a communication channel, such as Ethernet (e.g. wired or wireless—WiFi), Blue Tooth, I2C, or other open or proprietary communication channel.

An example method is provided for regulating a movement of a limb including a joint using any of the orthopedic device described herein. The method includes positioning the orthopedic device along the limb, such that the central portion of each of the two rigid components is positioned proximate to an axis of rotation of a joint of the limb, using at least one processing unit to compute an angle of bending of flexion or extension of the limb, and using the at least one processing unit to transmit instructions to cause a clutch coupled to the at least two cables to regulate the separation between the respective two protrusions of each of the two rigid components, thereby regulating the movement of the limb.

At least one sensor component is used to provide data indicative of at least one of an angle of bending of flexion or extension of the limb, a muscle activation condition, a pressure on a foot during a gait cycle, an instance in time that a foot strikes a surface during a gait cycle, or the tensile force in each cable. Data from the one or more sensors can be used to determine data indicative of the angle of bending of flexion or extension of the limb. The example system can include at least one actuator coupled to the at least two cables to apply a tensile force to the at least two cables.

In an example orthopedic device according to the principles herein, a motor can be used in conjunction with a clutch. The motor can be connected to the spectra line of a cable, either along its length before the clutch, connected to the shaft the clutch is mounted to, or at any other location. In this example, the clutch could serve to hold the spectra line of the cable, while the resilient components (including elastic elements) in the example orthopedic device are stretched (e.g., based on joint angle). In this example, the motor could be configured to function as a generator, so that when the clutch is released, the motor could be configured to harvest the energy stored in the resilient components (including elastic elements).

In an example orthopedic device according to the principles herein, energy could be harvested from the movement to charge a capacitor, a battery, a fuel cell, or other power source. The power source could be used to power the clutch and the microprocessor.

In an example orthopedic device according to the principles herein, the timing of the signals from the control system of can be set based on many possible scenarios. For example a powered element (such as the clutch or motor) could be engaged based on the angle or velocity of a first limb (such as a first leg), the angle or velocity of a second limb (such as but not limited to the opposite leg, the time of contact of the second limb with the ground or other surface, the first limb being in contact with the ground or other surface, or any combination of these. An alternate control system by the control system could use the angle of the first limb reaching a maximum value as a trigger for the powered element (such as but not limited to disengaging the clutch and/or discontinuing the tensile force exerted by the motor).

In an example orthopedic device according to the principles herein, the powered element could be used to cause the applied force to be lowered smoothly over a longer period of time (e.g., the time period covering 10-20% of the gait cycle), instead of instantly or in a short period of time. In an example where the powered element is a clutch, the start time of the clutch releasing the cable could be earlier than it would be otherwise, such that the force is mostly released when the leg needs to be free for a range of motion. The clutch or other powered element could release fully if the opposite limb had planted, even after a ramp-down period for the force. This control system sequence of a prolonged force release can be used in an orthopedic device including a motor or damper in series with the cable, with the motor or dampler either absorbing the energy or acting as a generator. The damper could also be a one-directional damper, only absorbing energy from the system if the orthopedic device was releasing force, and not if the limb was being loaded initially. This would enable dampers with longer time constants to be used.

In an example orthopedic device according to the principles herein, the cable can be disposed to remain in line with rigid end, rigid component, or other rigid elements, so the cable would remain planar in-line when the orthopedic device is subjected to load forces during use.

The example orthopedic device can be configured to facilitate easy donning and doffing. As a non-limiting example, the cable could be removable from the rigid elements, so the rigid elements could be worn constantly and the actuation system (including the cable) is coupled to the rigid elements only when needed. In an example, slots can be introduced into the sides of the rigid elements to facilitate the coupling of the actuation system (including the cable).

The example orthopedic device can be configured to facilitate an amount of flexibility in the area of the joint so that slight motion is possible in the frontal plane and coronal plane. This is beneficial, e.g., when the rigid elements need to be tapered to follow the shape of the limb (such as a tapered shape).

In an example orthopedic device according to the principles herein, simplified clutch box could be used that includes a precision clock spring. The spring could be used for applying a tension to the cable and facilitate rewinding of the cable.

In an example orthopedic device according to the principles herein, the cable of a first base mechanism could be controlled and actuated separately from the cable of the second base mechanism.

In an example orthopedic device according to the principles herein, the clutch could be mounted to a portion of the base mechanism, or could be mounted to a separate area of the wearer (such as but not limited to a backpack or other device).

In an example orthopedic device according to the principles herein, the sensors could be configured to sense the knee joint angle using encoders or other means, or using accelerometers or gyroscopes mounted to a portion of the orthopedic device, e.g., to detect foot-falls, limb joint angle (including knee joint angle), or other gait events.

In an example orthopedic device according to the principles herein, the resilient component (such as but not limited to the springs or other elastic element) could be configured with some initial tension so that there is a larger force immediately for small changes in the limb (e.g., small knee angle changes). This could be done in conjunction with a hard stop at the joint, preventing it from bending beyond an orientation and potentially lead to hyperextension (e.g., a knee being bent past vertical in the "wrong" direction).

An example orthopedic device according to the principles herein can be used to provide resistive torques as a function of joint angle when the limb is in any bent configuration, even if it is stationary or straightens out after bending initially. The example orthopedic device can be configured to store energy in springs or other elastic elements, which become loaded as the limb is bent, and then either returning most of that energy to the wearer as the limb straightens, or by releasing the energy into dampers or an electric generator.

An example orthopedic device according to the principles herein can be configured to provide assistive torques to the knee to support lifting heavy objects or strength enhancement for applications, such as but not limited to, rigid exoskeletons or impaired individuals. In the examples, the orthopedic device could be used with actuators to straighten the limb actively, or again use spring or other resilient components to store energy as the limb is bent and release it. The example orthopedic devices herein can be made lighter and simpler than existing technologies, and can require less power (e.g., in a configuration that uses a clutch to hold the energy in the springs or other resilient components.

An example orthopedic device according to the principles herein can be configured to provide a resistive force about the knee that is always present if the knee is bent. This could be used for applications such as but not limited to skateboarding, skiing, snowboarding, or waterskiing, where the wearer remains in a crouched position for longer periods of time.

An example orthopedic device according to the principles herein can be configured to substantially self-align with the joint, regardless of the motion of the limb.

An example orthopedic device according to the principles herein can be configured to locking a clutch while the leg is straight, so that the orthopedic device provides a resistive torque if the leg is bent. The example orthopedic device can be configured to continue to apply the torque if the wearer holds their position, for example, if the wearer is searching for a foot-plant location while walking downhill. The example orthopedic device can be configured to also apply torques if the wearer lifts their body up again, for example if the wearer reverses their direction of walking. During an implementation for downhill walking, the example orthopedic device can be configured to then disengage a clutch when the knee is bent. This can smoothly release the force on the leg, permitting the knee to bend additionally to prepare for swing without restriction. The example orthopedic device can be configured such that, when the force is released, the released force is used to power a generator.

An example orthopedic device according to the principles herein can be configured for assistance with lifting. In this example, the clutch can be locked while the limb is straight, and then the wearer would squat to pick up a heavy object. When the wearer stands up, the example orthopedic device can be used to provide assistive forces as they straighten their leg, at which point the clutch could be released and they could walk normally.

In an example orthopedic device according to the principles herein, the sensors can be Stochastic Resonance (SR) sensors.

Figure 13A:
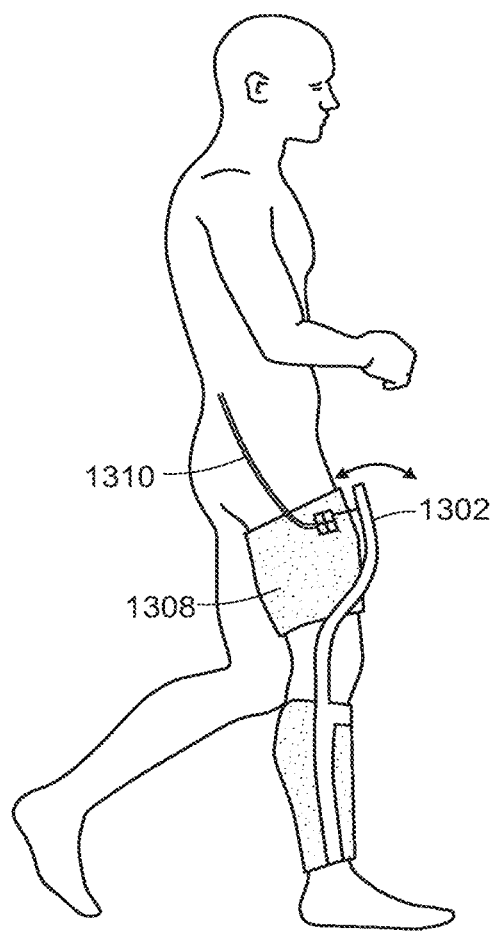
Figure 13B:
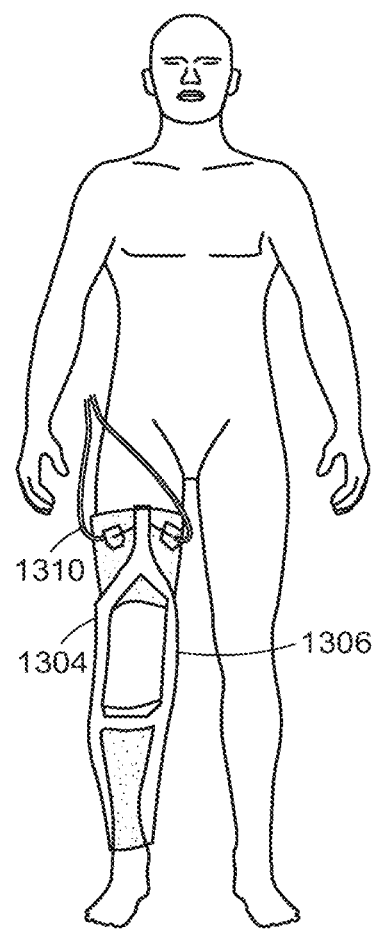

FIGS. 13A and 13B show an example orthopedic device formed from a resilient member 1302 that includes a medial resilient component 1304 for positioning along a medial side of a limb including a joint and a lateral resilient component 1306 for positioning along a lateral side of the limb. The medial resilient component 1304 and the lateral resilient component 1306 each extend from a distal portion of the limb to a proximal portion of the limb past the joint, and are configured to extend toward an anterior side of the proximal portion of the limb. The medial resilient component 1304 and the lateral resilient component 1306 meet to form an intersection portion proximate to the proximal portion of the limb (indicated at 1302). A powered element, such as but not limited to an actuator unit or a clutch, is coupled to the intersection portion of the resilient member. The powered element (actuator unit or clutch) is configured to restrict a movement of the intersection portion on receiving a signal indicating that the limb is in flexion, thereby causing the resilient member to deform to store an amount of potential energy. An interface 1308 couples the resilient member 1302 to the limb, to cause the resilient components to apply an amount force, based on the stored potential energy, to cause an amount of extension of the limb.

The example orthopedic device can include a cable to couple the resilient member 1302 to the powered element. For example, the orthopedic device can include at least one cable linking the intersection portion of the resilient member to the actuator unit or the clutch. An elastic member can be disposed in series between the at least one cable and the actuator unit or the clutch.

In the example of FIGS. 13A and 13B, at least one of the medial resilient component and the lateral resilient component comprises a leaf spring. The resilient member 1302 can be formed from a leaf spring that extends up from the wearer's lower leg and is connected to the thigh via a Bowden cable 1310. If the wearer bends their knee, the leaf spring could provide a restoring force to straighten it again. This could occur if a clutch was locked, or if an actuator was providing a force to the cable.

In an example, an additional spring can be disposed in series with the Bowden cable, possibly at the end with a clutch or actuator unit.

In an example, a clutch or actuator unit can also be mounted on the thigh. In this example, the Bowden cable can be omitted.

Any example control system herein can be used to analyze data from a sensor component to generate the signal indicating that the limb is in flexion.

The powered element (such as the actuator unit or a clutch) can be configured to restrict or retract the at least one cable on receiving the signal indicating that the limb is in flexion, thereby causing the at least one cable to apply a tensile force to the intersection portion of the resilient member to cause the resilient member to deform.

Figure 14A:
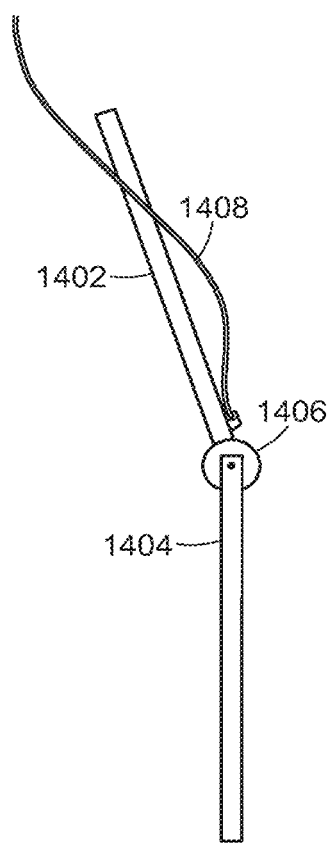
Figure 14B:
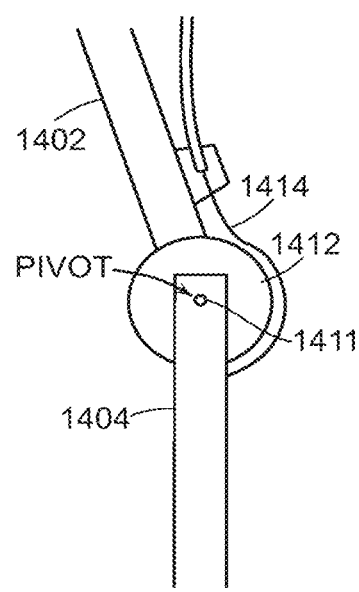

FIGS. 14A and 14B show an example orthopedic device that includes two resilient components for positioning along a opposite sides of a limb including a joint, on the medial and lateral sides. The two resilient components are formed as a proximal resilient component 1402 for positioning along a proximal portion of the limb, and a distal resilient component 1404 for positioning along a distal portion of the limb. The example orthopedic device includes a pulley system coupled to at least one cable 1408. The pulley system 1406 is coupled to the proximal resilient component 1402 and the distal resilient component 1404 such that the pulley system 1406 is configured to restrict a rotation between the two resilient components on receiving a signal indicating that the limb is in flexion, to cause the resilient components to deform, thereby storing an amount of potential energy.

At least one of the proximal rigid component and the distal rigid component comprises a leaf spring. In an example, the two leaf springs may be connected by a pivot 1411 (shown in FIG. 14B).

As shown in FIG. 14B, the pulley system can include a drum 1412 around which the cable is wound. The drum is attached to one of the resilient components and not the other. In an example, the drum is attached to the proximal resilient components and not the distal resilient component.

As shown in FIG. 14A, the inner cable of the Bowden sheath is wound around the drum of the pulley system.

In an example, the orthopedic device can also include an interface coupled to the limb, to cause the resilient components to apply an amount of a force, based on the stored potential energy, to cause an amount of extension of the limb. If they are locked together, the entire structure can be deformed (bent) to store energy. The interface can be formed as a fabric interface to the wearer (not shown).

In non-limiting examples, the resilient components either can be locked together, using a Bowden cable plus clutch or actuator, as shown, or using a clutch mounted at the pivot or free to rotate. If they are locked together, the entire structure can be deformed (bent) to store energy. This would be used in conjunction with a fabric interface to the wearer (not shown).

Any example control system herein can be used to analyze data from a sensor component to generate the signal indicating that the limb is in flexion.

The example system further includes at least one of a clutch and an actuator coupled to the at least one cable, to cause the pulley system to restrict the rotation between the two resilient components.

FIGS. 15A and 15B show an example orthopedic device that includes two rigid components 1502 and 1504 for positioning along a medial side or a lateral side of a limb including a joint. The device includes a proximal rigid component 1502 for positioning along a proximal portion of the limb and a distal rigid component 1504 for positioning along a distal portion of the limb. The device includes a pulley system 1506 including at least one cable, wherein the pulley system is coupled to the proximal rigid component and the distal rigid component such that the pulley system causes a tensile force to be applied to at least one of the two rigid components, to cause a rotation of the proximal portion of the limb relative to the distal portion of the limb about the joint, thereby applying a force to cause a degree of a flexion or an extension of the limb.

The example orthopedic device can further include a rigid bar that is non-rotatably coupled to the distal rigid component and to a housing of the pulley. The cable can be connected to the distal rigid component to cause a rotation of the proximal rigid component relative to the distal rigid component. A motor can be coupled to the at least one cable, configured to actuate the at least one cable to rotate the pulley.

In an example, the proximal rigid component or the distal rigid component can be formed from a leaf spring, or at least one of the two rigid components can be formed from a carbon fiber rod.

The example orthopedic device can include a rigid bar that is non-rotatably coupled to the distal rigid component and to a housing of the pulley. The at least one cable is connected to the distal rigid component to cause a rotation of the proximal rigid component relative to the distal rigid component.

The pulley system can be configured such that a flexion motion of the limb causes extension of the at least one cable and cause extended portions of the at least one cable to retract around the pulley when the flexion motion is discontinued.

An example control system can be coupled to the pulley system, to cause the pulley system to retract the at least one cable to increase a magnitude of the tensile force applied to the at least one of the two rigid components, or to cause the pulley system to release the at least one cable to reduce the magnitude of the tensile force applied to the at least one of the two rigid components. A load cell can be coupled to the at least one cable, to determine the magnitude of the tensile force of the cable.

The example control system can be configured to issue commands based on data indicative of movement of the joint, received from the sensors. The control system can include at least one sensor unit to provide data indicative of the gait of a wearer of the orthopedic device, and an actuation component coupled to the pulley system, to cause the pulley system to retract the at least one cable based on the data from the at least one sensor unit. In another example, the control system can include a clutch coupled to the at least one cable, wherein the control system is configured to cause the clutch to lock on receiving a signal indicating that the limb is extended. The control system is configured such that the clutch can be manually unlocked. For example, the control system can include a manual switch coupled to a portion of the limb, to actuate the pulley system In another example, the control system can include at least one memory and at least one processing unit configured to execute instructions stored in the memory, to cause the orthopedic device to compute at least one of a joint angle of the joint and a point of a gait cycle, and to transmit instructions to cause the clutch to regulate the at least one cable based on at least one of the computed joint angle and the point of the gait cycle, for exerting the tensile force.

In an example, the orthopedic device can include at least one sensor configured to provide data indicative of the joint angle, the point of the gait cycle of a wearer of the orthopedic device, data indicative of a gradient of ascent of the wearer, data indicative of the degree of extension or flexion of the limb (including data indicative of an angle between a proximal portion of the limb and a distal portion of the limb to provide the data indicative of the degree of extension or flexion of the limb), or a foot sensor to detect a heel strike of a wearer of the orthopedic device.

The orthopedic device can further include an interface coupled to the limb, to cause the tensile force applied to at least one of the two rigid components to be applied to the limb, thereby causing the rotation of the proximal portion of the limb relative to the distal portion of the limb about the joint. The interface can be formed from a flexible material.

Studies have shown the lower extremity joint moments and angles for younger adults for different inclined slopes and for stairs. An elderly person's gait can differ. Climbing stairs requires a larger range of joint angles and higher moments than walking on level ground. The knee extension moment for ascending stairs increases almost threefold. These changes can be due to the increased potential energy needed to raise one's center of mass (CoM).

Figure 16:
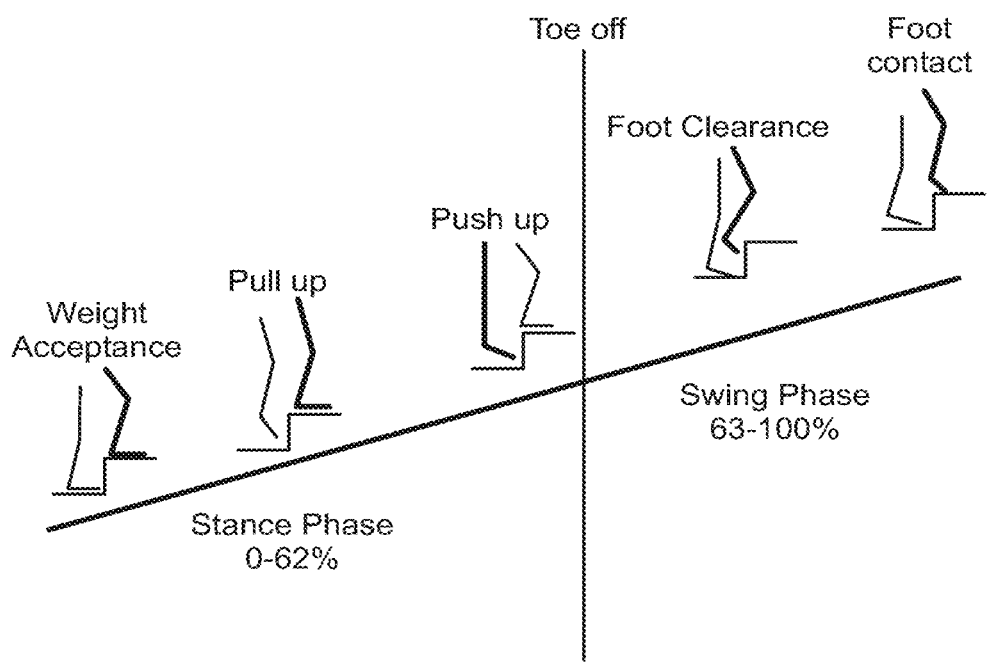
FIG. 16 shows two stride cycles or one gait cycle for stair ascent, according to the principles herein.

A gait cycle includes the time between foot contact and the next time the same foot meets the ground. FIG. 16 illustrates two stride cycles or one gait cycle for stair ascent. FIG. 16 focuses on the position of one leg through the entire cycle, which is in bold. At the beginning of the gait cycle to ascend stairs, the person first makes foot contact and transfers weight to that leg; the ankle is dorsiflexed and the hip and knee are flexed. Then the hip and knee extends to bring the body upward during the pull up phase. After the trailing foot leaves the ground and has made contact with the next stair, the leg in bold then plantarflexes to push the CoM upward and onto the other leg during the push up phase. The foot leaves the ground (toe off), which ends the stance phase and begins the swing phase. The hip and knee flex to clear the ground and plant the forefoot on the next step, which is the end of the gait cycle (100% of the gait cycle).

The percentages of gait cycle are computed averages. The body lifts itself in two ways. Temporally, the trailing leg pushes up first using plantarflexion, then the leading leg hip and knee extends to pull the body upward. These two actions are shown in FIG. 16. This phase of the gait cycle requires the most work by the muscles in order to generate enough potential energy. The ankle has peak power production at 54-56% of the gait cycle during the push up phase while the hip and knee have peak power production at 16 and 18-20% of the gait cycle, respectively during the pulling up phase.

The kinematics of walking up an incline is similar to those of walking up stairs. To walk uphill, again, the ankle plantarflexors, during the double support phase, and hip and knee extensors, during the single support phase, provide higher moments than during level walking in order to raise the CoM. The primary difference between incline and stairs is that inclines require higher ankle dorsiflexion (20 percent) and lower knee flexion moments (40%). The table below shows the positive work rate in healthy adults for walking up different inclines. The instantaneous work rate can be computed as the dot product of the ground reaction force and the CoM velocity. The integral of the instantaneous work rate over an interval yields the total work rate.

| Incline (degree) | Positive Work Rate (W/kg) |
| --- | --- |
| 0 | 0.39 |
| 3 | 0.40 |
| 6 | 0.51 |
| 9 | 0.62 |

Most elderly experience sarcopenia, the reduction of muscle mass, which is commonly associated with decreased strength and moment capacities. Neural degeneration also occurs, which leads to the use of proximal over distal leg muscles. Older adults become more cautious when walking and further modify their gait. Together these changes have a number of effects on gait and in general, make daily tasks even walking on level ground more difficult. Yet, walking up stairs and inclines pose an even larger problem for older adults. Ascending an incline differs from walking on level ground in that the leading leg's hip and knee extensors along with the trailing leg's plantarexor must perform more work to raise the body's CoM. This device, which assists normal movement by providing added torque about the knee and hip, can help the elderly to perform these challenging tasks by assisting extension of the joints to help elevate the CoM.

The biomechanics of walking up and incline and stairs do differ slightly. Yet, this difference is small enough such that one device can help elderly in ascending both stairs and inclines. The overall moment requirements and timing are very similar between the two actions. The main difference between the two actions for both younger and older adults is higher dorsiflexion and lower knee flexion moments required for walking up an incline.

Older adults have lower trailing leg propulsion due to decreased plantarflexion moment, which requires them to rely more heavily on hip and knee extension during the pull up phase of the gait. The device provides added moment about the knee and hip, rather than the ankle, to make it easier for them to climb stairs in a way that is feels natural to the user. The device does not aim to modify an older adult's gait to mirror that of a younger adult, but to increase their overall mobility. The maximum moment output for the knee and hip while ascending stairs is much closer to the person's maximum capacity for elderly than it is for younger adults. The table also displays percent of capacity, which is the average maximum peak moment over the moment capacity for that movement.

The device provides an added moment so that older adults can produce a smaller moment and still ascend the stairs. Studies have shown that when an assistive torque is applied, humans decrease their muscle activation so that the overall moment output is matches the usual moment profile during walking. Therefore, with assistance, the moment they produce can be a smaller percentage of their overall capacity. The assistive moment needed is calculated based on the percent of capacity that young adults use while ascending stairs, which is 35% for the hip and 40% for the knee. The device can add moment about the hip such that that the older adult is producing 35% of their maximum hip capacity. If their capacity is 1.17 Nm/kg, then the older adult must produce no more than 0.41 Nm/kg. The peak moment output of the hip during gait is 0.65 Nm/kg so the device must add 0.65×0.41=0.24 Nm/kg. A similar calculation can be done to determine the added moment necessary for the knee.

In an example implementation, the orthopedic device can have the following attributes:
Wearable underneath the user's clothing
  Provide up to 25% torque, 0.16 Nm/kg at the hip or 0.25 Nm at the knee,
which is 13 N and 20 N assuming an 80 kg person
  Actuate during the appropriate phase of the gait cycle
  Operate 10 times for 5 minutes before recharging
  Don and Doff easily in less than 2 minutes
  Straightforward and simple to operate
  Provide little resistance to hip or knee flexion
  Comfortable
  Weigh less than 5 kg
  Various example orthopedic devices are described that are based on differing actuation systems.

Figure 17:
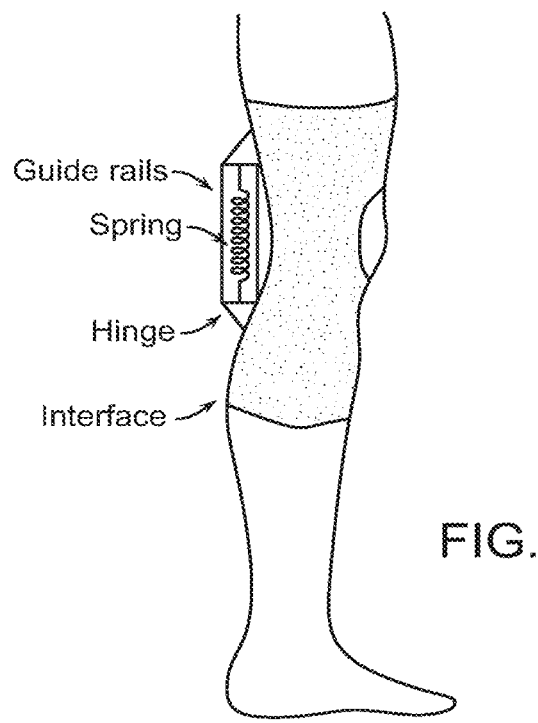
FIGS. 17-25B show example orthopedic devices, according to the principles herein.

FIG. 17 illustrates an orthopedic device comprising an actuated spring on a wearer. The example device includes an extended spring coupled to a limb (in this non-limiting example, a leg) posterior to the joint. He example device uses the spring force to aid knee extension and actuation to flex the knee by compressing the spring. To limit or eliminate torsion on the spring, the spring can be disposed between two platforms with guide rails such that the platforms are substantially parallel. During flexion, the guide rails can be actuated to decrease in length, thereby compressing the spring. Once the knee has fully flexed and the user is about to enter the pull up phase of the gait, the actuator disengages, and the spring expands vertically, producing a moment about the knee to aid extension.

Actuators can be used to extend the spring during flexion and such that the spring is in the extended position and compresses during knee extension. To ensure consistent moment output of the springs, a guiding mechanism can be used so that the springs are restricted from moving to the side of the leg and hinder knee extension.

The device of FIG. 17 can be worn outside the clothes.

Figure 18A:
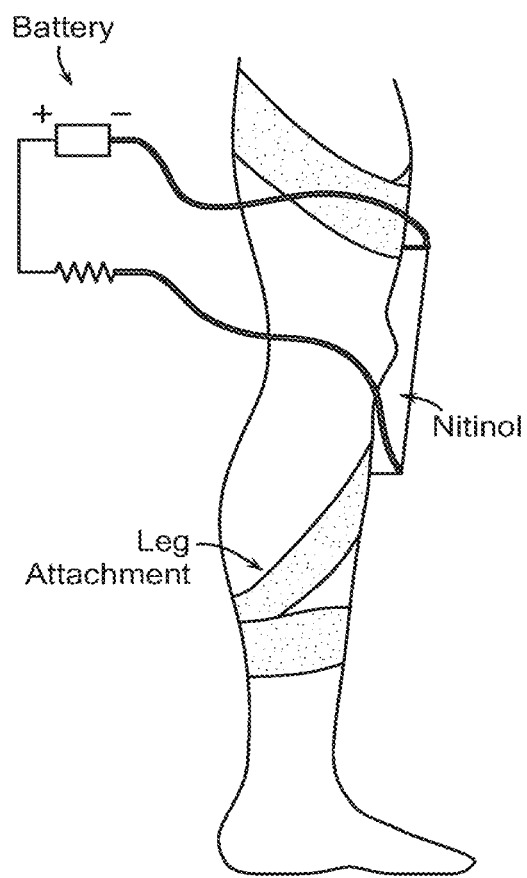
Figure 18B:
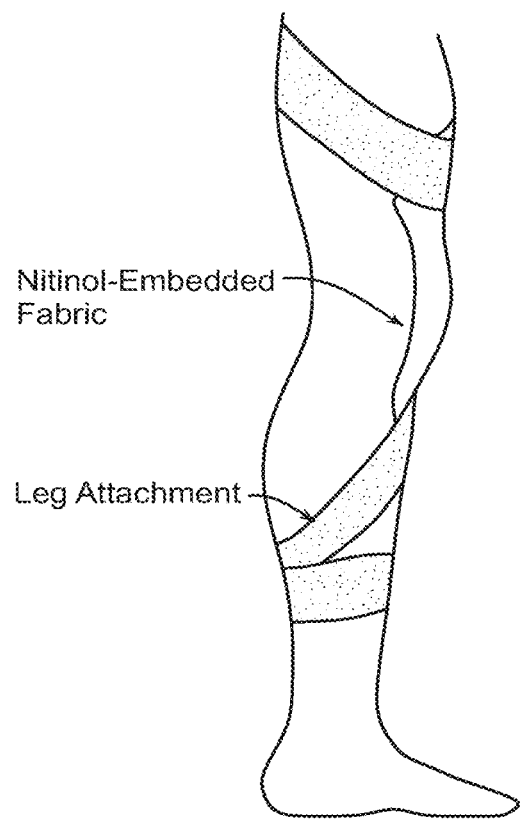

FIGS. 18A and 18B illustrate an orthopedic device comprising a nitinol wire on a wearer. In the device of FIGS. 18A and 18B, the actuation device is nitinol-based. Nitinol, a shape memory alloy, can return to the original shape at which it was annealed when an electric current is supplied. If the wire is placed in front of the knee, when powered, it shortens in length and can aid extension of the knee. If the wire is annealed in a spring shape, the effective length of the wire decreases to the length of the spring. It is possible to use other such shapes for this purpose.

A power supply and Arduino can be used to actuate and control the wire.

In an example, a single wire or multiple wires can be placed on the front of the knee as shown in FIGS. 18A and 18B, and wires can be interwoven, or they can be embedded in a fabric. Multiple wires can be used on either side of the patella to provide more force and also more anchor points to help distribute the force. The wires are placed closer to the center the knee otherwise, when actuated, they could promote knee flexion rather than extension. The wires can also be woven together or embedded in a fabric, which can provide more comfort and possibly provide the needed force. The Nitinol may not be a feasible solution for actuation.

Figure 19:
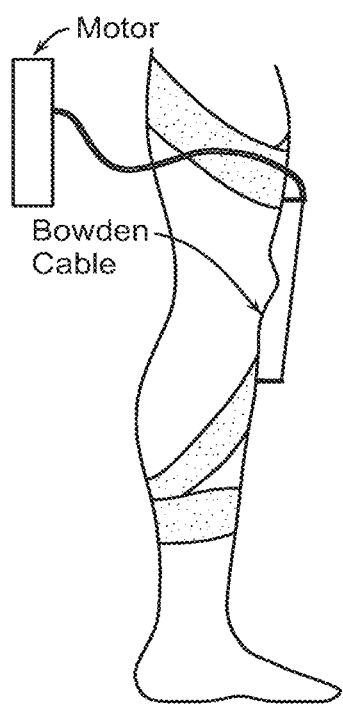

FIG. 19 illustrates an orthopedic device comprising cable-based actuation on a wearer. In the device of FIG. 19, the cable based actuation system uses a motor and pulley to move a cable that is attached to the shin and thigh. When the motor pulls on the cable, the length shortens thereby helping the knee to extend. The cable can be placed slightly away from the body so that it is comfortable for the user. This may require that the device be worn outside the clothing, which is undesirable. Placing cables on either side of the patella may be a better option, but may require a mechanism to prevent the cables from falling to the sides of the leg such that it assists flexion when actuated. During flexion the cable can be made slack such that it does not interfere with normal movement.

Figure 20:
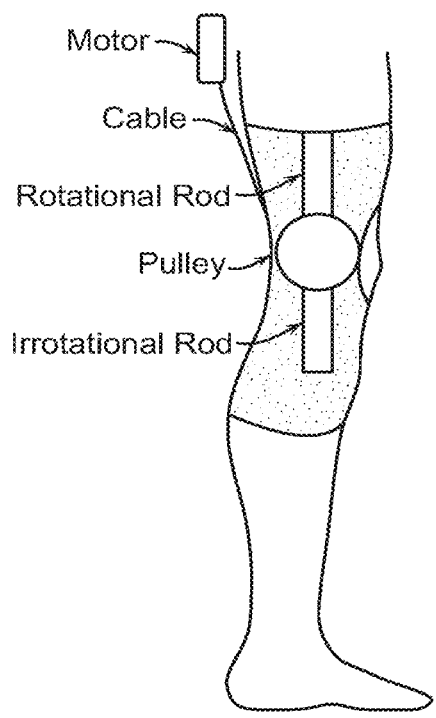

FIG. 20 illustrates an orthopedic device comprising cable-actuated pulley on a wearer. In the device of FIG. 20, the pulley is placed on the outside of the knee and is attached to one Bowden cable, a plate and two rods, one on the thigh and one on the shin. When the motor attached to the Bowden cable actuates, it will rotate the pulley. The top rod is coupled to the pulley but the bottom rod is attached to the non-rotational plate behind the pulley. When the pulley rotates clockwise, the top rod moves relative to the bottom rod such that the two rods are in line. This can assist the user in extending their knee. When the user flexes their knee, the Bowden cable is slack and the wearer should experience no resistance. The cable rewinds itself around the pulley so that it is ready for actuation.

Figure 21A:
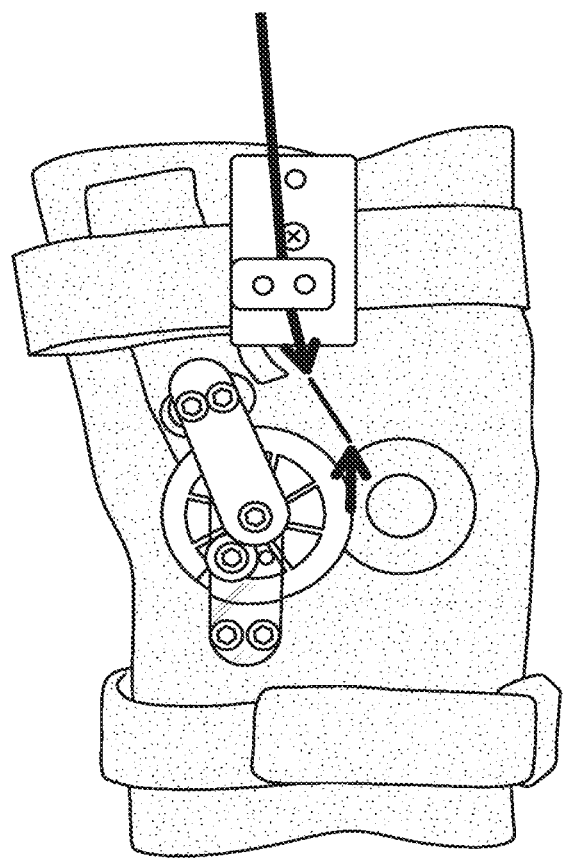
Figure 21B:
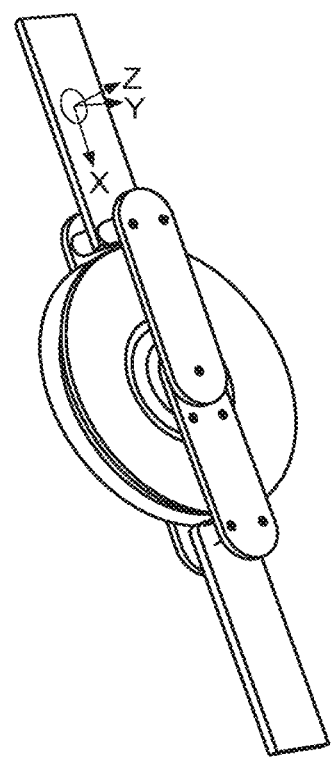

An example implementation of an orthopedic device is shown in FIG. 21. In the device of FIG. 21, laser cut acrylic rods are embedded in two pockets on the side of an interface. This allows the device to fit closer to the leg and transfer torque to it. Inextensible straps above and below the knee secure the brace and ensure that the rods are coupled to the body well. In this example, the lower rod is fixed to the pulley. When pulling on the cable, the rods move and as a result the orthopedic device is actuated. The housing for the sheath and cable are not securely attached to the interface. A downward force applied to the cable causes the sheath holder to move downward toward the pulley, which can be undesirable.

An example orthopedic device is provided that includes a metal sheath holder coupled to a metal loop (see FIG. 23) and fastened using Velcro fastener on the upper part of the interface to hold the loop in place. When pulling on the cable, the sheath moves if the brace moves, but does not move relative to it. The example orthopedic device of FIG. 22 includes an acrylic plate and a long rod on either side of the pulley for both the upper and lower parts of the pulley. This allows the rigid components to lay more closely to the limb rather than be offset from the knee. This example orthopedic device is more comfortable, includes fewer parts, and has a lower profile. The example orthopedic device includes an extended brace and rods so that the force can be transferred to the leg over a larger area, which should be more comfortable for the user.

Figure 22:
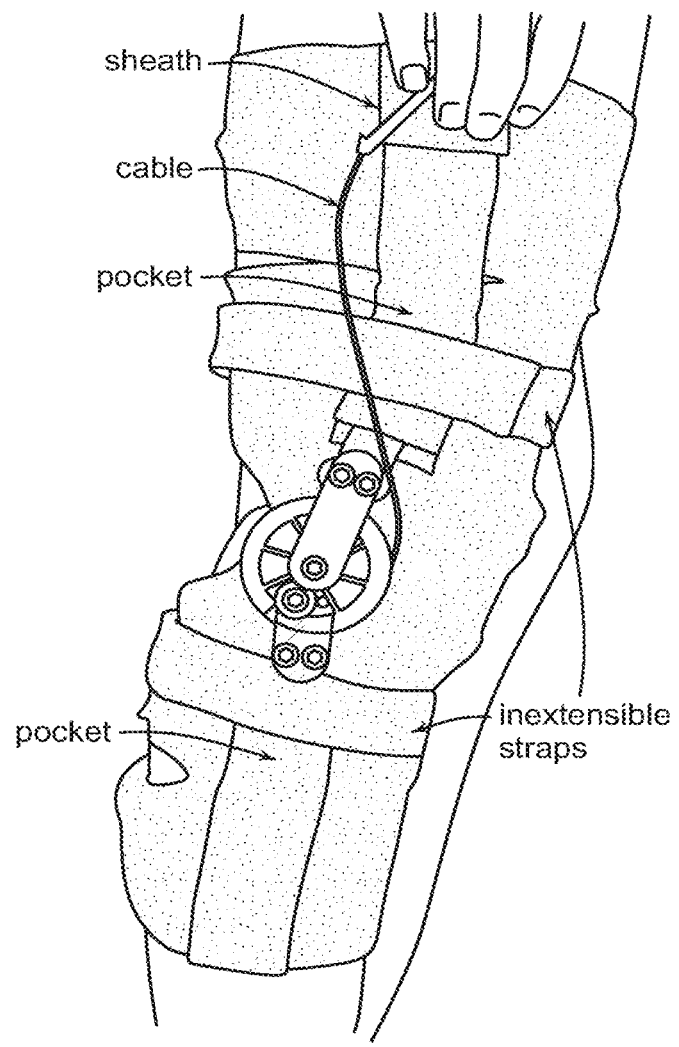
Figure 23:
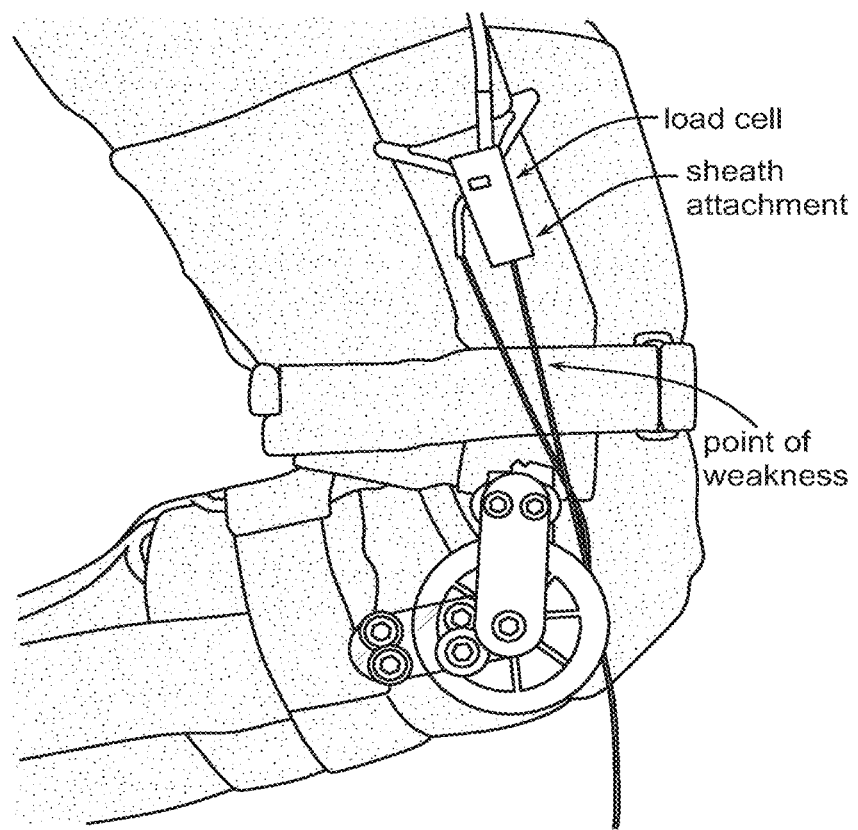

FIG. 22 illustrates an orthopedic device comprising a sheath on a wearer. In the device of FIG. 22, the sheath is attached so that the least amount of exposed cable is present. The sheath attachment is directly above the pulley (FIG. 24 so that the cable exits and is then in contact with the pulley. The sheath enters a hole in the side of a piece of acrylic; the hole narrows so that the cable, not the sheath can exit the other side. The hole is angled so that the cable exits and runs parallel rather than perpendicular to the pulley's track. This helps the cable to run as efficiently as possible. Also, the cable terminates where the bottom rod couples to the pulley. In this example, the cable is not looped through a hole in the pulley, which could prevent the cable from laying at on the pulley.

Figure 24:
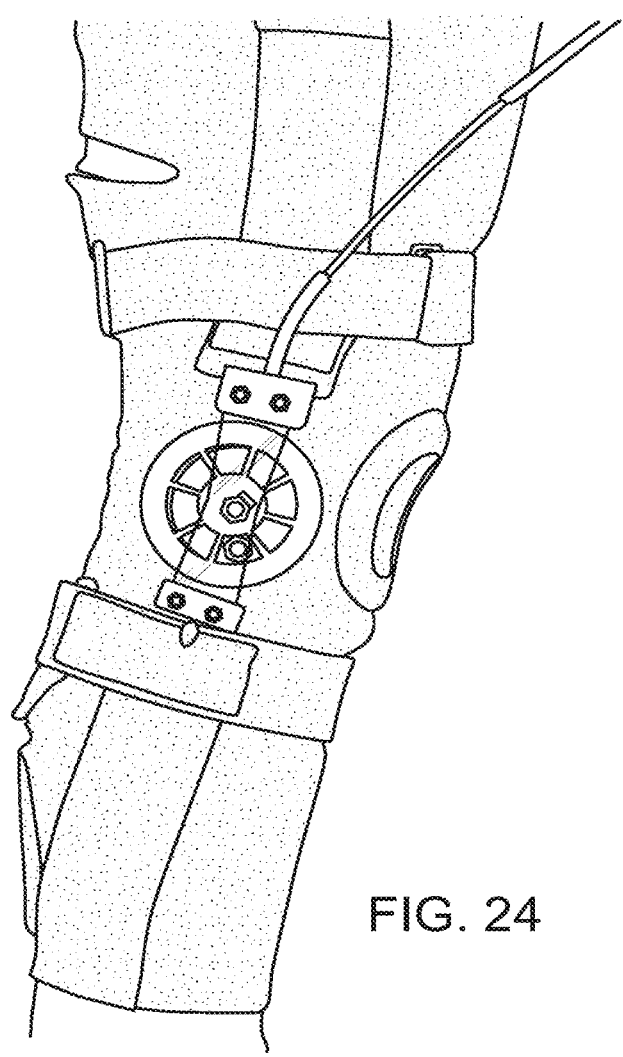

FIG. 24 illustrates an orthopedic device comprising an exemplary interface on a wearer. In the device of FIG. 24, an interface including reinforcements such that the force generated by the motor and transferred to the cable and rigid members are effectively transferred to the limb. The example orthopedic device includes inextensible fabric, four straps above the knee (two in front and two in back) and four straps below the knee.

Figure 25A:
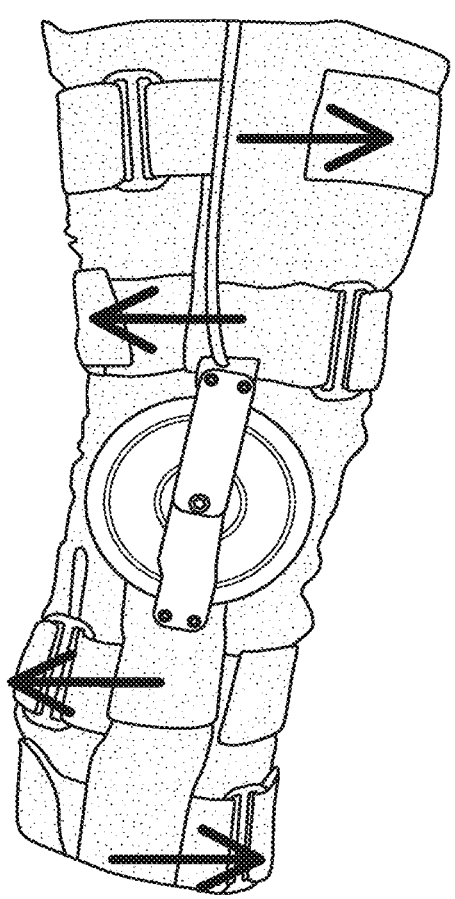
Figure 25B:
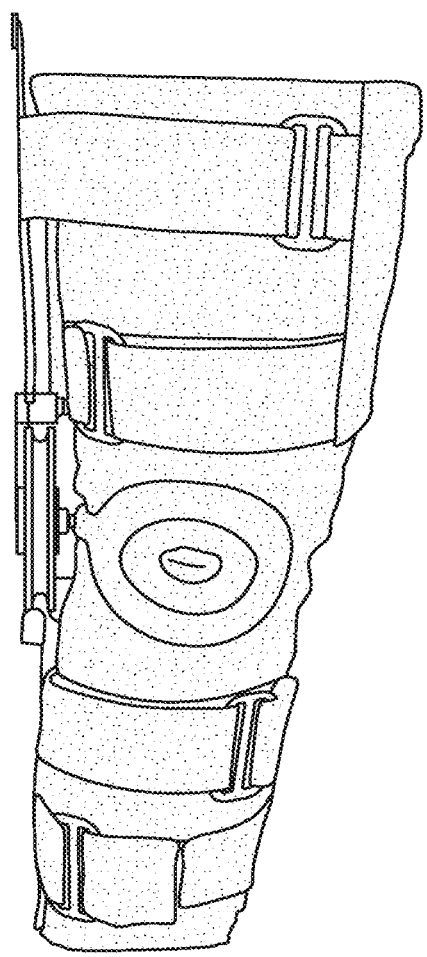

FIGS. 25A and 25B illustrate two views of an exemplary orthopedic device on a wearer. FIG. 25A shows the free body diagram (FBD) of how the rods apply forces to the pockets. FIG. 25B shows a front view of the device.

Figure 26A:
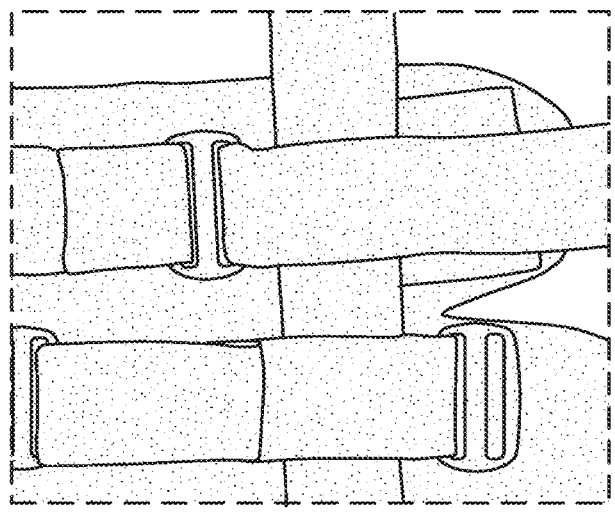
FIG. 26 shows an example device including reinforcements, according to the principles herein.
Figure 26:
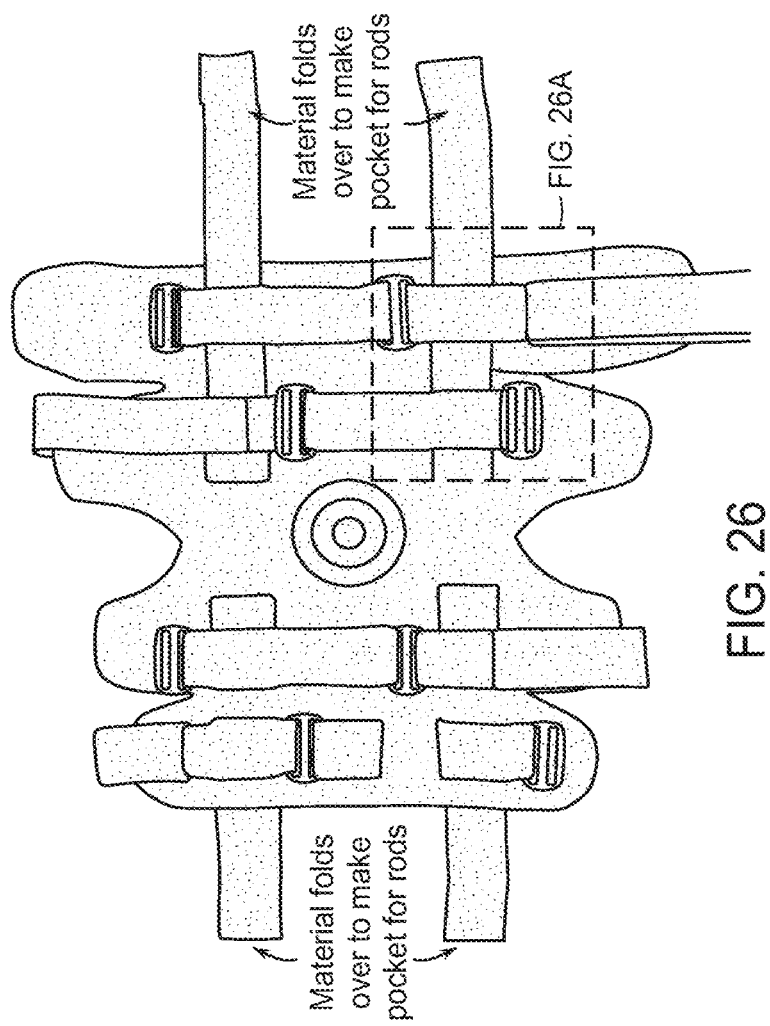
Figure 27C:
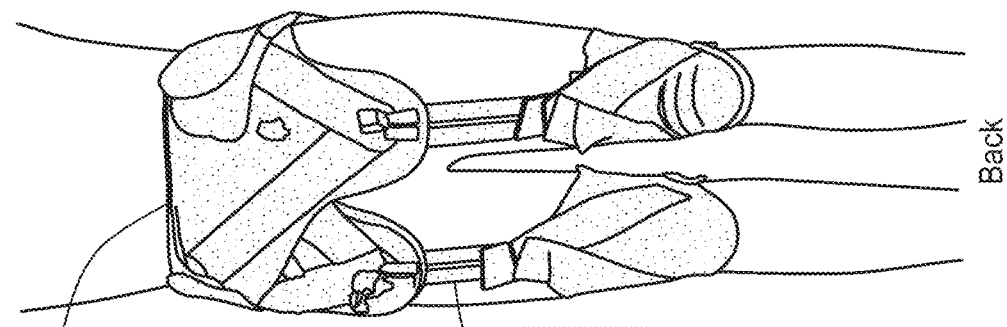
Figure 27B:
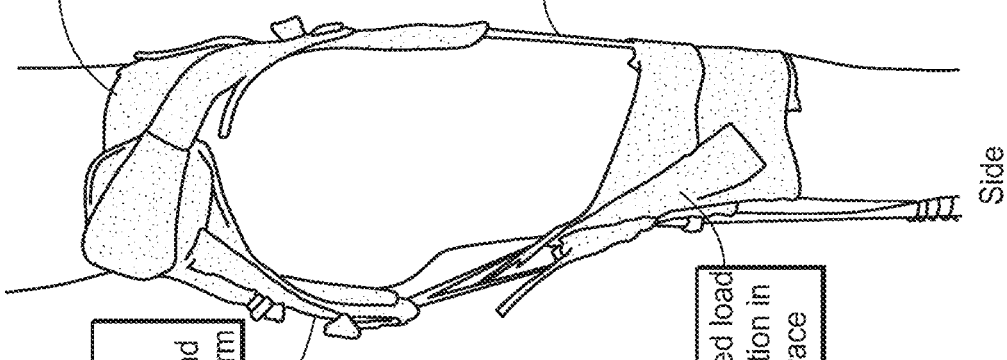
Figure 27A:
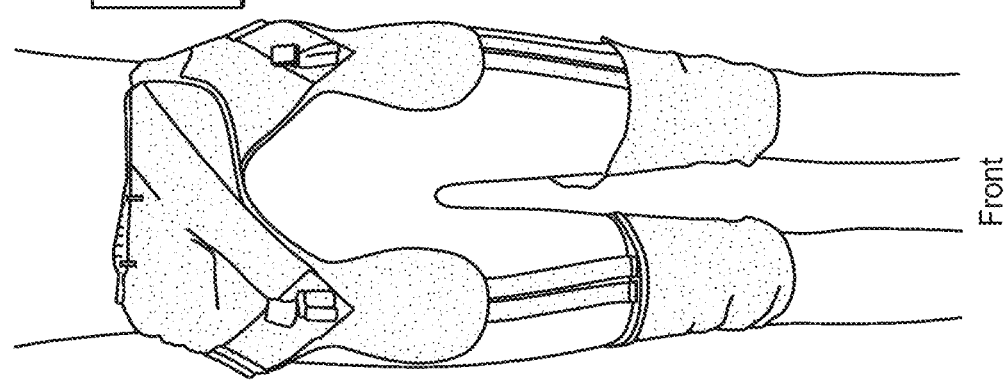
Figures 28A, 28B:
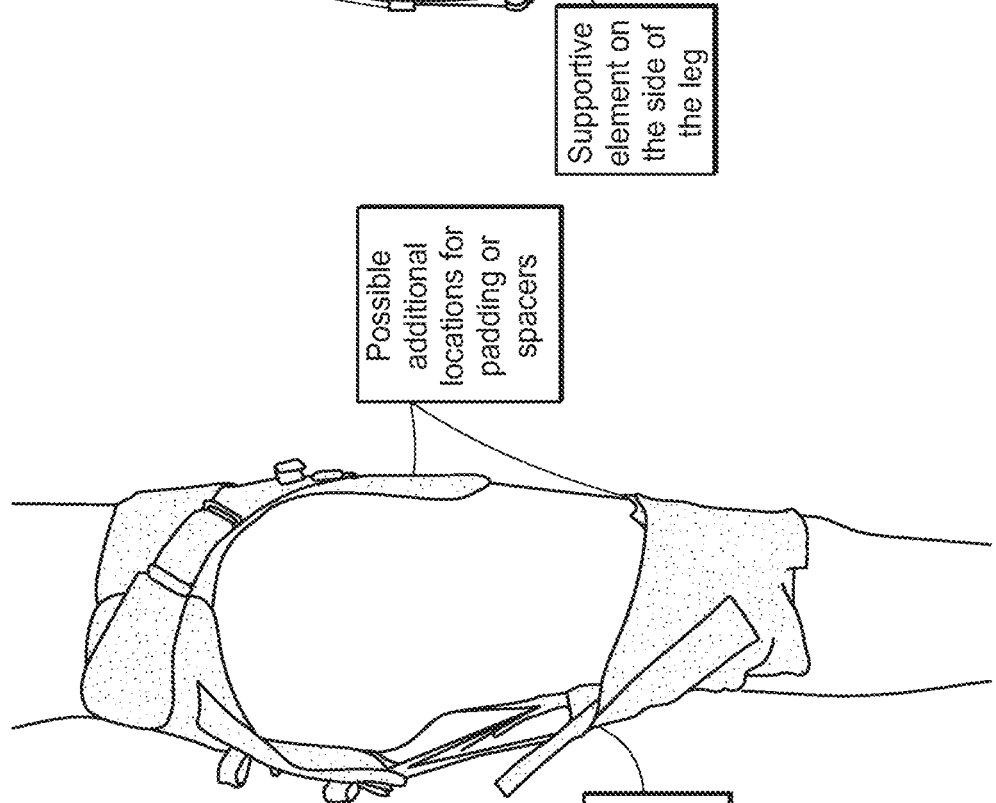
Figure 29:
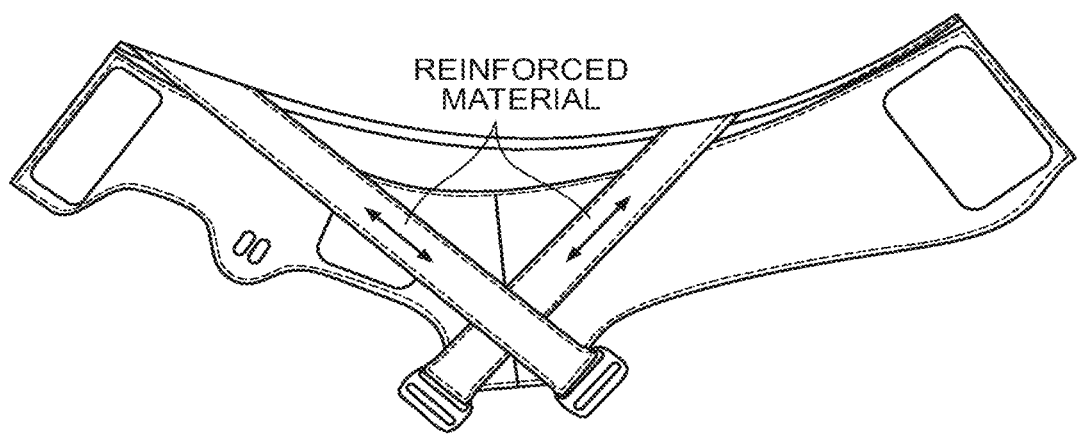

FIG. 26 illustrates an example device including reinforcements. The rods themselves are more robust, and the brace has further reinforcements so that the rods do not move or minimally relative to the leg. Laser cut 0.06" mm steel is a better alternative to the acrylic rods that break so easily while still allowing for a quick manufacturing process. The rod and pulley system are more secure with In order to actuate the cable that causes the brace to move, the cable can be attached to actuation unit, which includes of a motor, gear box, pulley, motor controller and batteries. The cable attaches to a pulley and when the motor shaft rotates, the pulley moves, thereby moving the cable. These items can be housed in a unit worn on the user's back. The cable from the knee and the sensor from the foot couple to the bottom of the unit.

An example exosuit can include passive elements and powered elements. The passive elements can be used for energy storage (e.g. as artificial exotendons, etc.). The active elements, such as actuators (e.g. cable drive, pneumatic, etc.) can be powered via on-board or off-board power supplies. The passive and/or powered elements can be interfaced with the wearer via compliant materials and a soft wearable fabric. In some aspects, the exotendons can be resilient and behave biomimetically as tendons (e.g., as an elastic band), storing energy supplied from natural biomechanical movement or from actuators configured in series within the exotendons themselves, and releasing such stored energy during complementary movement. The actuators may include, by way of example, one or more air-powered pneumatic actuators, one or more DC motors, one or more electro-active materials (e.g. polymer), or combinations thereof.

An example orthopedic device herein facilitates load transfer. An example capability of the orthopedic devices is that, whether used as a standalone, or in combination with a soft exosuit, it can provide a means to transfer load via a rigid connection to the ground that is parallel to the wearer's skeletal structure. This could be the weight of the device itself, some portion of the weight of the wearer, or additional load that is carried by the wearer. The could be achieved by connecting the distal end of the rigid bar on the shank to the ground via the ankle joint and/or the proximal part of the rigid bar on the thigh to a harness, other interface to the wearer or payload.

The knee device could be combined with similar linkages or other rigid structures around the ankle and hip to create a exoskeleton that supports each joint in the lower limbs.

Non-Limiting Example Orthopedic Device Interface

The interface used to couple the orthopedic device to the limb can be formed from any type of material that couples to the limb the forces exerted by the cable, powered elements, the resilient components, and any other passive elements.

In an example implementation, the interface can be formed from a fabric, a flexible material, or other similar material, including VELCRO® fasteners (VELCRO INDUSTRIES B.V., the Netherlands). In an example, the interface can be a portion of an exosuit.

Types of padding and spacers are described. In an example, a padding or spacers can be used in conjunction with a soft exosuit to lift the exosuit, an actuation cable, or other part of the system away from the body. In another example, reinforcement elements can be incorporated along specified paths in a textile in order to change the force distribution pattern in the textile.

Non-limiting examples of padding or spacers are described. The padding or spacers can be used in conjunction with an exosuit in many locations. These elements could be placed under a wide area of cloth, or in specific smaller locations such as where an actuation cable attaches to the textile (see FIGS. 27A through 28B). This padding or spacers could be rigid or semi-rigid elements (e.g. plastic), soft components (e.g. a rubber or foam), or a combination of these (e.g. a rigid shell with a soft inner liner).

A rigid material would be beneficial because it would be less likely to compress when forces were applied in the suit. A rigid material with a softer cushioning material underneath it (between the rigid material and the body) also would be beneficial so that the body would not feel sharp edges on the rigid material or pressure points due to the rigid material. The rigid material could also be curved to conform to the wearer's body. Furthermore, rigid materials could be precurved in a manner such that force in the exosuit causes the rigid materials to bend slightly, and in their bent shape they exert a desired pressure distribution on the body. When there is no force or a reduced force in the exosuit, they could return to their original shape.

Example functions of padding and spacers are described. Padding or spacers could provide a number of benefits to an exosuit's function. These elements could lift the exosuit textile or the exosuit's cable away from the body, creating a larger moment arm through which the exosuit could act on a joint. This would permit higher joint torques to be applied with smaller tensile forces in the exosuit.

Alternatively, padding could lift a cable or actuated region away from the body. Often, an actuated region may have the tendency to press into the body as it is shortened. Padding or spacers could lift this region away from the body, so that when it contracts, this stretch is held away from the body (so it does not touch the body or underlying textiles) or presses into the body with reduced pressure.

Padding or spacers placed under an actuated region could also protect the body or an underlying textile from the motion or abrasion of the actuated region itself, or from rigid/sharp components that are part of the actuators (for example, the mechanism at the point of connection between the actuator and the textile exosuit).

Padding or spacers could also serve to distribute pressure in the textile in a desired pattern over the body. This could mean distributing the force in the textile over a more uniform area, or creating concentrations of force over specific parts of the body that are better able to support the force. In both of these cases the padding or spacers could lead to additional comfort for the wearer.

In FIGS. 27A through 28B, examples of padding/spacers can be seen at the back of the waist and back of the thigh, where a foam has been placed between the textile and the human. In these figures, additional locations are indicated at the front of the leg, where spacers can occur at the front of the waist, front of the thigh, or underneath the cable between the waist and thigh. At the back of the waist, here, the padding creates a small offset from the body so that the cable and force sensors do not press into the body during actuation. This also improves the actuation's effectiveness, since it slightly increases the moment arm about the hip.

The paths of reinforced materials in textiles are described. Reinforcement elements can be added to textiles in specified paths in order to improve the performance of the exosuit. This is shown in FIGS. 27A-27C, and FIG. 29 through FIG. 32D. If there is a large area of cloth or textile with certain stress-strain properties, then additional segments, patches, or lengths of textile or other material can be added to it in order to create different stress-strain characteristics in those areas. This composite material can be constructed to create desired force distributions over the body when worn (with no additional force) and when force is applied in the textiles. Also, textiles can be arranged in certain orientations and attached together to create desired stress-strain patterns and force distributions even without additional reinforcing elements.

Figure 30A:
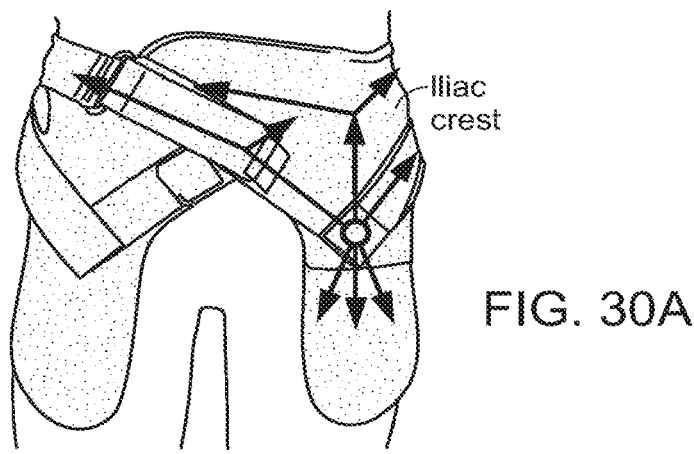
Figure 30B:
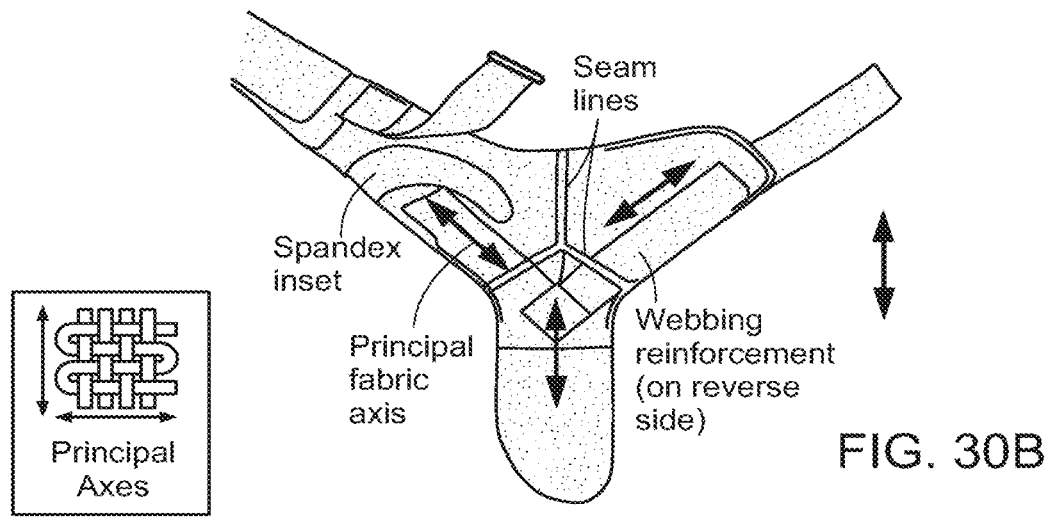
Figure 30C:
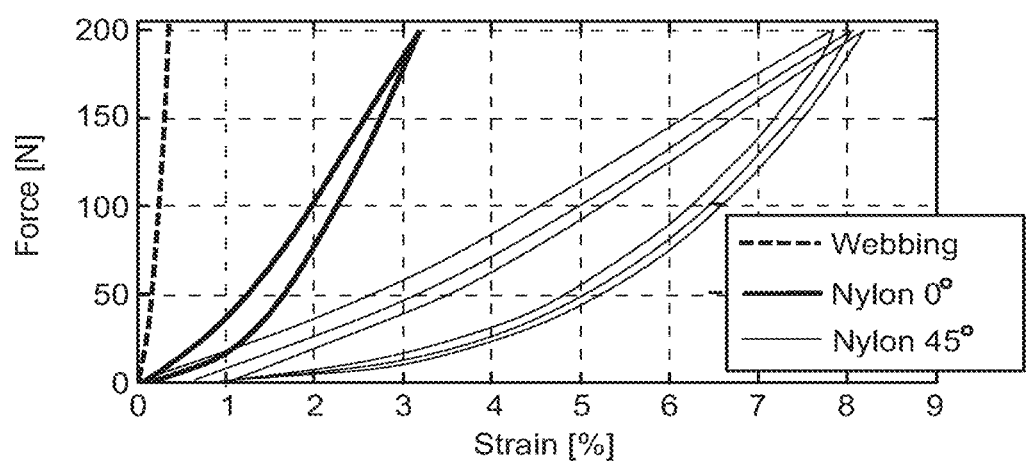
Figure 32D:
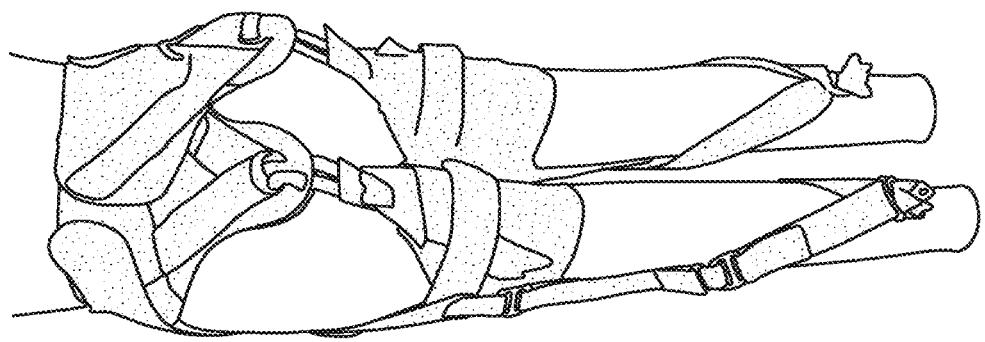
Figure 32C:
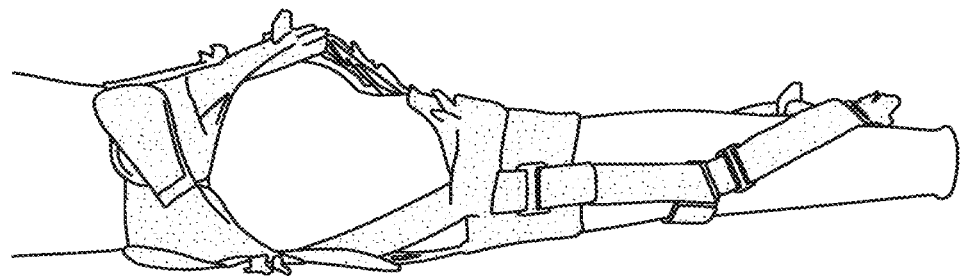
Figure 32B:
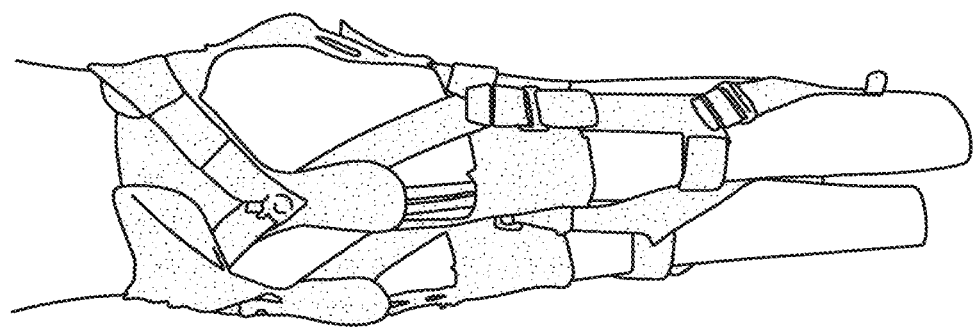
Figure 32A:
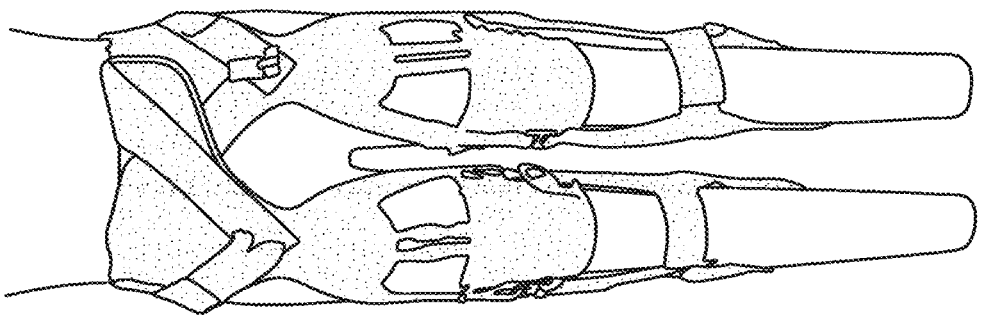
Figure 33A:
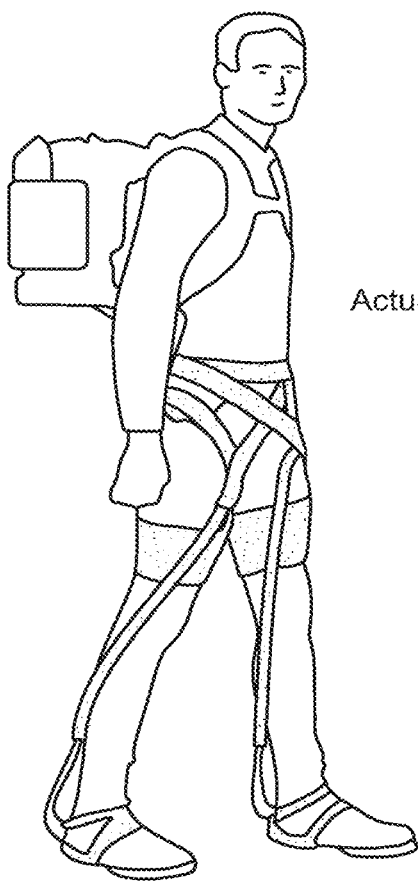
FIGS. 33A-34B show example exosuits, according to the principles herein.
Figure 33B:
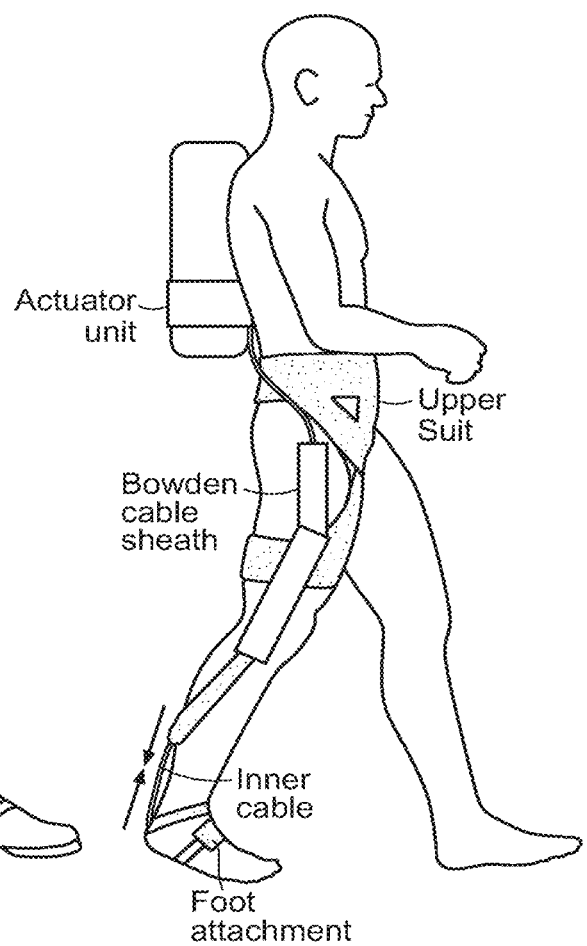
Figure 34A:
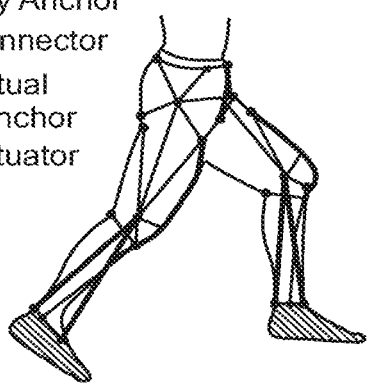
Figure 34B:
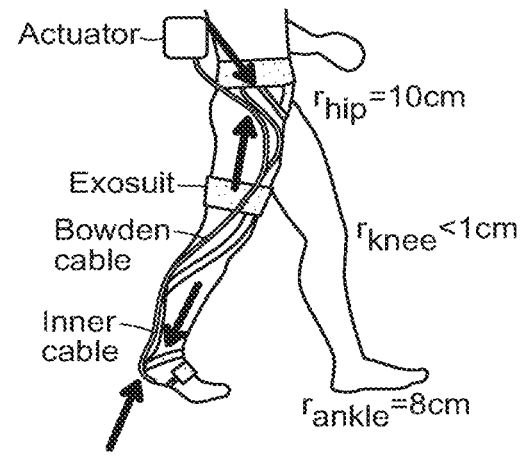

In the figures, a woven textile is shown reinforced with seatbelt webbing in certain paths. This is best illustrated in FIGS. 29 and 30A-30C, which illustrate the design of a waist belt. FIG. 30A shows a desired force distribution to transmit force from the front of the leg to the sides of the waist and around the pelvis in a comfortable manner. Force in the textile is illustrated by the arrows, and the textile in this example is constructed to have the forces in the garment meet primarily at a single point indicated by a circle, although in general any arbitrary force distribution can be created. To achieve this force distribution, the waist belt is constructed as shown in FIG. 30B. As shown in the small inset in the left of the figure, woven fabrics have two primary directions in which threads extend. These are labeled "primary axes" in the figure, and are known as the warp and weft directions in a textile. In these directions, the threads themselves support tensile forces, whereas in the directions 45 degrees from these primary axes (called the "bias"), the weave structure of the fabric supports force as well. This leads to the measured strain vs. force characteristics in FIG. 30C, where samples of material 5 cm wide by 20 cm long were tested. If a fabric is stretched on the bias, there will be generally much more strain to achieve a given force level, as is shown in this example. For comparison, seatbelt webbing is a different material that has a much denser weave and is much thicker, so it has a much lower strain for a given force. This is also shown in FIG. 30C.

To achieve the force distribution in FIG. 4A, the waist belt is constructed as shown in FIG. 4B. Patches of woven textile are oriented as shown by the arrows in FIG. 4B such that the primary axes are parallel to the arrows. This construction leads to increased stiffness in those directions. To increase stiffness further in certain areas, seatbelt webbing is sewn onto the woven textile in specific locations and in specific angles. This construction of reinforcements with seatbelt webbing in certain key areas in conjunction with oriented textiles underneath is also shown in FIGS. 27A-29, FIGS. 31A-31C, and FIGS. 32A-32D. FIGS. 27A-30C and FIGS. 32A-32D show this construction at the waist belt, and FIGS. 5 and 6 also show it on a thigh attachment.

FIGS. 31A-31C show another example of this construction, this time to create an attachment to the thigh of a wearer. In this case, if an upward force is applied to the exosuit at a point roughly at the intersection of the wide blue reinforcement seatbelt webbing strips, then the pattern of force in the textile is shown approximately by the thinner green lines shown on the figure. To make the textile stiffer in these directions, seatbelt webbing is added as shown by the wide blue strips. In this particular example, the reinforcement is added at the back of the thigh brace because that is the region of highest forces and hence highest strains.

This patterning is useful because it can decrease the stretch of the textile in those key directions of force, while permitting the textile to potentially stretch more in other directions to accommodate the wearer's shape or motion. Alternatively, the underlying textile could be oriented to support force in other directions than the reinforcement piece. For example, in FIGS. 31A-31C the base woven textile could be oriented with its principal axes vertically and horizontally. In this case, the blue seatbelt webbing would lie approximately in the direction of the bias of the fabric. To reduce the stretch in this region, the seatbelt webbing could be added on this bias path, thereby making the stretch in that direction lower than it would be without the reinforcement.

Also shown in FIGS. 31A-31C, the thigh braces could also be constructed with slits in arcs extending from the webbing to the front and back of the device. If there are directions with lower forces, then the fabric could be intentionally split to reduce or eliminate force in those areas, again to potentially lead to better conformation to the body or a better force distribution over the body. Slits in arcs could allow the brace to expand with the leg while still transmitting loads to the front and back of the leg in the pathways that resist motion most effectively. A connective layer of spandex or another more-compliant material could be between the slits in order to hold the garment together and provide a small amount of force transfer between the segments. An alternate version of this principle is shown in FIGS. 30A through 30C where an inset of spandex is included in the pattern to reduce the forces in the textile in that area. Since spandex can stretch many times more than a nylon textile, for example, then force is substantially reduced in the area of spandex. In the waist belt, this can be positioned over the iliac crest of the pelvis in order to reduce the pressure there. It can be desirable to reduce pressure in regions where a bone is protruding or very close to the skin, since otherwise this could lead to a high pressure concentration there and discomfort. This principle could also be applied to attachments to the body for prosthetic limbs made out of textiles.

Non-Limiting Example Exosuits

The example orthopedic devices according to the principles herein may be used in isolation as an independent system, or coupled to an interface (as described hereinabove). Alternatively, the example orthopedic devices may be integrated with any of the wearable system (also referred to herein as "exosuit") disclosed in PCT/US/1360225, filed Sep. 17, 2013, titled "Soft Exosuit for Assistance with Human Motion"; U.S. Provisional Patent Application Ser. No. 61/936,162, filed Feb. 5, 2014, titled "Multi-robot Cyberphysical System for Assisting Walking in Developmentally-Delayed Toddlers Application"; U.S. Provisional Patent Application No. 61/913,863, filed Dec. 9, 2013, titled "Soft, Wearable Exosuits, Assistive Devices and Related Systems"; and U.S. Provisional Patent Application No. 61/928,281, filed Jan. 16, 2014, titled "Soft, Wearable Exosuits, Assistive Devices and Related Systems", each of which preceding application is incorporated herein by reference in its entirety.

In a non-limiting example where the orthopedic devices are used in conjunction with an aforementioned wearable systems disclosed in one or more of PCT/US/11360225, or Provisional Patent Application Nos. 61/936,162, 61/913, 863, or 61/928,281, incorporated herein by reference in their entirety, such combination with the wearable systems (e.g., the soft exosuit) can (1) help prevent migration of the knee exoskeleton disclosed herein, (2) advantageously utilize soft exosuit energy injection at ankle or hip to minimize the metabolic cost of wearing the knee exoskeleton, and (3) enable the soft exosuit to utilize the rigid elements of the knee exoskeleton to provide a path for some load transfer (either as a standalone device or as part integrated with a soft exosuit).

In addition to being used as a stand-alone device, the proposed knee brace may also be combined with other soft exosuit designs that assist other joints.

For example, it could be combined with a multi-articular soft exosuit that provides assistive torques to the wearer at the ankle and hip during walking. Like other exosuits, it uses textiles to create tensile forces over the body in parallel with the muscles, which enables it to be light (2.0 kg on both legs, 10.1 kg total) and not restrict the wearer's kinematics. An example feature of the exosuit is that it can generate forces passively due to the body's motion, similar to the body's ligaments and tendons. These passively-generated forces can be supplemented by actively contracting Bowden cables using geared electric motors, to create peak forces in the suit of up to 200N. Measurements of the suit-human series stiffness is measured on several subjects. Human-subjects testing is also performed to determine the metabolic benefit provided by the suit as well as its effect on the wearer's kinematics. Five subjects have an average best-case metabolic reduction of 9.0% during loaded walking with 34.6 kg of carried mass including the exosuit and actuators. Wearing the exosuit does not change the kinematics of the hip and knee, while peak ankle dorsiflexion and plantarflexion angles is shifted towards plantarflexion (toe pointing downward) by less than 2.5 degrees.

FIGS. 33A-34B illustrate the concept of virtual anchors in exosuits for connecting actuators to a mono-articular exosuit. The right figures show the force distribution throughout a multi-articular suit and the moments arms at the ankle, knee and hip.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, one or more floppy disks, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A wearable device comprising:
    a pair of base mechanisms for positioning along opposite sides of a limb, each base mechanism comprising:
        a base portion having a rigid first end, a rigid second end, and a central region;
        the central region of the base portion for positioning proximate to an axis of rotation of a joint of the limb, wherein the central region is configured to permit rotation of the rigid first end with respect to the rigid second end; and
        a first anterior protrusion extending from the rigid first end of the base portion, proximate to the central region, toward an anterior side of the axis of rotation of the joint to a first pivot point;
        a second anterior protrusion extending from the rigid second end of the base portion, proximate to the central region, toward an anterior side of the axis of rotation of the joint to a second pivot point; and
        a cable coupled to the first pivot point and the second pivot point;
    a control system that receives input from at least one sensor indicating an occurrence of at least one event in a movement of a wearer of the wearable device and generates a responsive control signal; and
    at least one powered element that receives the responsive control signal from the control system and, in response, controls a tensile force through the cable between the first pivot point and the second pivot point of each base mechanism to produce beneficial forces in the pair of base mechanisms that are translated to the wearer.

2. The wearable device of claim 1, wherein:
    the limb is a leg;
    the control system, in response to first input indicating one or more of a foot strike in the leg, a forefoot contacting a ground, or a knee angle passing through an inflection point from increasing to decreasing, generates a responsive control signal that causes the at least one powered element to limit an extension of the cable or to increase the tensile force through the cable to limit a maximum separation between the first pivot point and the second pivot point of each base mechanism of the pair of base mechanisms to provide resistance to a flexion of a knee; and
    the control system, in response to second input indicating a foot strike in another leg of the wearer in a descent movement, generates a responsive control signal that causes the at least one powered element to discontinue limiting the extension of the cable or to reduce the tensile force through the cable to allow an increased separation between the first pivot point and the second pivot point of each base mechanism of the pair of base mechanisms.

3. The wearable device of claim 1, wherein:
    the limb is a leg;
    the control system, in response to first input indicating a beginning of an extension moment of a knee, generates a responsive control signal that causes the at least one powered element to increase the tensile force through the cable to decrease a maximum separation between the first pivot point and the second pivot point of each base mechanism of the pair of base mechanisms; and
    the control system, in response to second input indicating an approach of an end of the extension moment of the knee, generates a responsive control signal that causes the at least one powered element to reduce the tensile force through the cable to allow an increased separation between the first pivot point and the second pivot point of each base mechanism of the pair of base mechanisms.

4. The wearable device of claim 1, wherein:
    the limb is a leg;
    the control system, in response to first input indicating one or more of a foot strike in the leg, a forefoot contacting a ground, or a knee angle passing through an inflection point from increasing to decreasing in an approximately level or ascent movement, generates a responsive control signal that causes the at least one powered element to increase the tensile force through the cable to decrease a maximum separation between the first pivot point and the second pivot point of each base mechanism of the pair of base mechanisms; and
    the control system, in response to second input indicating one or more of the knee angle passing through an inflection point from decreasing to increasing, a hip of the leg passing through zero degrees, or a center of mass of the wearer reaching a maximum vertical excursion in an approximately level or ascent movement, generates a responsive control signal that causes the at least one powered element to reduce the tensile force through the cable to allow an increased separation between the first pivot point and the second pivot point of each base mechanism of the pair of base mechanisms.

5. The wearable device of claim 1, wherein the at least one powered element comprises at least one controllable clutch coupled to the cable of the base mechanism,
    wherein a locked state of the at least one controllable clutch limits a maximum allowable extension of the coupled cable, thereby limiting a maximum separation between the first pivot point and the second pivot point of the same base portion, and
    wherein an unlocked state of the at least one controllable clutch allows an extension of the coupled cable to vary, thereby permitting variable separation between the first pivot point and the second pivot point of the same base portion.

6. The wearable device of claim 5, wherein the control system permits the at least one controllable clutch to be manually unlocked.

7. The wearable device of claim 1, wherein the control system further comprises:
at least one memory; and
at least one processing unit configured to execute instructions stored in the at least one memory, to cause the wearable device to:
compute a joint angle of the joint in response to the input from the at least one sensor; and
generate the responsive control signal based, at least in part, on the computed joint angle.

8. The wearable device of claim 7, further comprising at least one sensor configured to provide data indicative of at least one of the joint angle, a muscle activation condition, a pressure on a foot during a gait cycle, an instance in time that a foot strikes a surface during a gait cycle, or the tensile force in each cable.

9. The wearable device of claim 7, further comprising at least one sensor configured to provide input indicative of gait for the wearer of the wearable device, wherein the joint angle is computed based on data indicative of gait.

10. The wearable device of claim 9, wherein the input indicative of gait comprises data indicative of a gradient of descent of the wearer.

11. The wearable device of claim 1, further comprising at least one standoff protrusion positioned at the central region of a first base mechanism of the pair of base mechanisms and/or the central region of a second base mechanism of the pair of base mechanisms, for maintaining the cable of each base mechanism separated at a distance from the axis of rotation of the joint.

12. The wearable device of claim 1, wherein the control system is further configured to generate a control signal that causes the at least one powered element to control the tensile force through the cable between the first pivot point and the second pivot point such that a resistive torque is applied to the limb on detection of a signal indicating a flexion of the limb or a signal indicating a degree of flexion of the limb maintained for a period of time greater than a predetermined threshold.

13. The wearable device of claim 1, further comprising at least one sensor unit coupled to a portion of the wearable device and/or a portion of the limb, to provide data indicative of a degree of extension or flexion of the limb.

14. The wearable device of claim 13, wherein the at least one sensor unit is configured to provide data indicative of an angle between a proximal portion of the limb and a distal portion of the limb, thereby providing the data indicative of the degree of extension or flexion of the limb.

15. The wearable device of claim 1, wherein the central region enables rotation of the rigid first end with respect to the rigid second end in at least one quadrant and prevents rotation of the rigid first end with respect to the rigid second end in two quadrants.

16. The wearable device of claim 1, wherein at least one of the rigid first end and the rigid second end comprises a leaf spring.

17. The wearable device of claim 1, wherein the first anterior protrusion is further configured as a longitudinal structure having a length that extends along the central region of the base portion towards the rigid first end.

18. The wearable device of claim 1, wherein the second anterior protrusion is further configured as a longitudinal structure having a length that extends along the central region of the base portion towards the rigid second end.

19. The wearable device of claim 17, wherein the longitudinal structure is a padded structure.

20. The wearable device of claim 1, wherein the at least one powered element comprises at least one actuator coupled to the cable, and wherein, in response to the control signal, the actuator may increase or decrease the tensile force through the cable between the first pivot point and the second pivot point.

21. The wearable device of claim 1, wherein the control of an extension of the cable comprises allowing a release of the cable of each base mechanism of the pair of base mechanisms on the occurrence of at least one event indicating that the limb is extended.

22. The wearable device of claim 1, wherein the central region comprises a series of at least three links.

23. The wearable device of claim 22, wherein the central region enables rotation of the rigid first end with respect to the rigid second end in at least one quadrant and prevents rotation of the rigid first end with respect to the rigid second end in two other quadrants.

24. The wearable device of claim 22, wherein each of the at least three links comprise incompressible blocks.

25. The wearable device of claim 24, wherein the central region comprises a flexible backing that couples the incompressible blocks, and wherein the flexible backing allows the central region to bend at a junction between the blocks.

26. The wearable device of claim 24, wherein each of the at least three links is formed with an angled portion, and wherein the at least three links are disposed relative to each other such that the angled portions of each link prevents the rotation of the rigid first end with respect to the rigid second end within at least two quadrants.

27. The wearable device of claim 22, wherein the at least three links are coupled via pin joints.

28. A wearable device comprising:
a pair of base mechanisms for positioning along opposite sides of a limb including a joint, each base mechanism comprising:
a base portion for positioning along a side of the opposite sides of the limb, the base portion having a rigid first end, a rigid second end, and a central region;
the central region of the base portion for positioning proximate to an axis of rotation of the joint of the limb, wherein the central region is configured to permit rotation of the rigid first end with respect to the rigid second end; and
a first anterior protrusion, configured to extend toward an anterior side of the axis of rotation of the joint, from the rigid first end of the base portion proximate to the central region to a first pivot point;
a second anterior protrusion, configured to extend toward an anterior side of the axis of rotation of the joint, from the rigid second end of the base portion proximate to the central region to a second pivot point;
a cable coupled to the first pivot point and the second pivot point and capable of exerting a tensile force between the first anterior protrusion and the second anterior protrusion; and
at least one resilient component selected from the group consisting of a first resilient component coupled to the first anterior protrusion and configured to apply a first force to the first anterior protrusion and a second resilient component coupled to the second anterior protrusion and configured to apply a second force to the second anterior protrusion, wherein, when the base portion is coupled to the limb, a force from the at least one resilient component is capable of applying a torque to the limb.

29. The wearable device of claim 28, wherein the at least one resilient component comprises:
a first resilient component that couples the first pivot point to the rigid first end of the base portion; and
a second resilient component that couples the second pivot point to the rigid second end of the base portion.

30. The wearable device of claim 28, further comprising at least one clutch coupled to the cable, for regulating a separation between the first pivot point and the second pivot point.

31. The wearable device of claim 30, further comprising:
at least one memory; and
at least one processing unit configured to execute instructions stored in the at least one memory, to cause the wearable device to:
compute a joint angle of the joint; and
to transmit the instructions to cause the at least one clutch to regulate the cable based on the computed joint angle, for regulating the separation between the first pivot point and the second pivot point.

32. The wearable device of claim 31, further comprising at least one sensor configured to provide data indicative of the joint angle.

33. The wearable device of claim 31, further comprising at least one sensor configured to provide data indicative of gait for a wearer of the wearable device, wherein the joint angle is computed based on the data indicative of gait.

34. The wearable device of claim 33, wherein the data indicative of gait comprises data indicative of a gradient of descent of the wearer.

35. The wearable device of claim 28, further comprising:
at least one actuator coupled to the cable; and
at least one controller configured to actuate the at least one actuator to regulate the cable, for regulating a separation between the first pivot point and the second pivot point.

36. The wearable device of claim 35, wherein the at least one actuator comprises at least one motor driven actuator, at least one pneumatic actuator, or at least one hydraulic actuator.

37. The wearable device of claim 35, wherein the at least one actuator comprises a motor driven actuator configured to apply a tensile force to the cable, for regulating the separation between the first pivot point and the second pivot point.

38. A wearable device comprising:
two rigid components, comprising:
a medial rigid component for positioning along a medial side of a limb including a joint;
a lateral rigid component for positioning along a lateral side of the limb;
wherein each of the two rigid components comprises:
a base portion for positioning along the limb, the base portion having a rigid first end, a rigid second end, and a central region, wherein the central region is configured to permit rotation of the rigid first end with respect to the rigid second end; and
two protrusions, comprising:
a first protrusion extending from the rigid first end along the plane of flexion of the limb to a first pivot point, and configured to rotate with respect to the rigid first end;
a second protrusion extending from the rigid second end along the plane of flexion of the limb to a second pivot point, and configured to rotate with respect to the rigid second end;
at least two cables, each cable being coupled to the respective first protrusion and second protrusion of each of the two rigid components, for regulating a separation between the respective first protrusion and second protrusion; and
at least two resilient elements comprising:
a first resilient component that couples to the first pivot point of the medial rigid component and is configured to apply a first force to the first pivot point; and
a second resilient component that couples to the first pivot point of the lateral rigid component and is configured to apply a second force to the second pivot point,
wherein the first force and the second force are capable of applying a torque to the limb.

39. The wearable device of claim 38, further comprising at least one clutch coupled to the at least two cables, for regulating the separation between the respective first protrusion and second protrusion of each of the two rigid components.

40. The wearable device of claim 39, further comprising:
at least one memory; and
at least one processing unit configured to execute instructions stored in the memory, to cause the wearable device to:
compute a joint angle of the joint; and
to transmit the instructions to cause the at least one clutch to regulate the at least two cables based on the computed joint angle, for exerting the first force and the second force.

41. The wearable device of claim 40, further comprising at least one sensor configured to provide data indicative of the joint angle.

42. The wearable device of claim 40, further comprising at least one sensor configured to provide data indicative of gait for a wearer of the wearable device, wherein the joint angle is computed based on the data indicative of gait.

43. The wearable device of claim 42, wherein the data indicative of gait comprises data indicative of a gradient of descent of the wearer.

44. A method for regulating an amount of force translated to a limb including a joint, comprising:
positioning the wearable device of claim 38 along the limb, such that the central portion of each of the two rigid components is positioned proximate to an axis of rotation of the joint of the limb;
using at least one processing unit to compute an angle of bending of flexion or extension of the limb; and
using the at least one processing unit to transmit instructions to cause a clutch coupled to the at least two cables to regulate the separation between the respective two protrusions of each of the two rigid components, thereby regulating the amount of force translated to the limb.

45. The method of claim 44, further comprising using at least one sensor component to provide data indicative of at least one of an angle of bending of flexion or extension of the limb, a muscle activation condition, a pressure on a foot during a gait cycle, an instance in time that a foot strikes a surface during a gait cycle, or a tensile force in each cable.

46. The method of claim 44, further comprising using at least one actuator coupled to the at least two cables to apply a tensile force to the at least two cables.

* * * * *